US008263075B2

(12) United States Patent
Cohen et al.

(10) Patent No.: US 8,263,075 B2
(45) Date of Patent: Sep. 11, 2012

(54) ANTIBODY MOLECULE FOR HUMAN GM-CSF RECEPTOR ALPHA

(75) Inventors: Emma Suzanne Cohen, Cambridge (GB); Ralph Raymond Minter, Cambridge (GB); Paula Rosamund Harrison, Cambridge (GB); Matthew Alexander Sleeman, Cambridge (GB); Andrew Donald Nash, Kew (AU); Louis Jerry Fabri, Diamond Creek (AU)

(73) Assignee: MedImmune Limited, Cambridge (GB)

( * ) Notice: Subject to any disclaimer, the term of this patent is extended or adjusted under 35 U.S.C. 154(b) by 1470 days.

(21) Appl. No.: 11/692,008

(22) Filed: Mar. 27, 2007

(65) Prior Publication Data

US 2012/0141464 A1   Jun. 7, 2012

Related U.S. Application Data

(60) Provisional application No. 60/786,569, filed on Mar. 27, 2006.

(51) Int. Cl.
*A61K 39/00* (2006.01)
*A61K 39/395* (2006.01)
*C07K 16/00* (2006.01)

(52) U.S. Cl. ............... 424/133.1; 424/139.1; 424/143.1; 424/144.1; 530/387.9

(58) Field of Classification Search ........................ None
See application file for complete search history.

(56) References Cited

U.S. PATENT DOCUMENTS 5,932,704 A   8/1999   Jubinsky

FOREIGN PATENT DOCUMENTS

WO   WO 94/09149   4/1994
WO   WO 94/11404   5/1994

OTHER PUBLICATIONS

Supplemental Information Disclosure Statement as executed by Tanya M. Harding (attached).
Chen et al., "Enhancement and destruction of antibody function by somatic mutation: unequal occurrence is controlled by V gene combinatorial associations," *EMBO Journal*, 14(12):2784-2794, 1995.
Colman, "Effects of amino acid sequence changes on antibody-antigen interactions," *Research in Immunology* 145:33-36, 1994.
Kussie et al., "A Single Engineered Amino Acid Substitution Changes Antibody Fine Specificity," *J. Immunol.* 152:146-152, 1994.
Rudikoff et al., "Single amino acid substitution altering antigen-binding specificity," *Proc. Natl Acad Sci USA* 79:1979-1983, 1982.
Hamilton, "Colony-stimulating factors in inflammation and autoimmunity," *Nature Reviews Immunology*, 8:533-544, 2008.
Lobato et al., "Intracellular antibodies and challenges facing their uses threapeutic agents," *TRENDS in Molecular Medicine*, 9:390-396, 2003.

Extended European Search Report, issued Feb. 1, 2012, in EP 11167912.2 (8 pages).
Extended European Search Report, issued Feb. 1, 2012, in EP 11167923.9 (6 pages).
Anderson, Ian "The challenges of bilogic drug discovery and development," Presentation at 4th James Black Conference (2006).
Crosier et al. "A functional isoform of the human granulocyte/macrophage colony-stimulating factor receptor has an unusual cytoplasmic domain," *PNAS* 88:7744-7748 (1991).
Drinkwater, C. et al., "CAM-3001, a human anti-human GM-CSFRa antibody; a novel therapeutic for the treatment of rheumatoid arthritis," Presentation in Melbourne, Australia (CAT/Zenyth/CSL meeting) (2006).
Drinkwater, C. et al., "Efficacy of antibodies targeting mouse and human GM-CSFRa," Presentation in Melbourne, Australia (CAT/Zenyth/CSL meeting) (2006).
Gram et al., "In vitro selection and affinity maturation of antibodies from a naive combinatorial immunoglobulin library," *PNAS* 89(8):3576-3580 (1992).
Haman et al., "Molecular Determinants of the Granulocyte-Macrophage Colony-stimulating Factor Receptor Complex Assembly," *Journal of Biological Chemistry* 274(48):34155-34163 (1999).
Jubinsky et al., "Expression and Function of the Human Granulocyte-Macrophage Colony-Stimulating Factor Receptor α Subunit," *Blood* 84(12):4174-4185 (1994).
Kurata et al., "Differential expression of granulocyte macrophage colony-stimulating factor and IL-3 receptor subunits on human CD34+ cells and leukemic cell lines," *J Allergy Clin Immunol* 96:1083-1099 (1995).
Monfardini et al., "Rational design, analysis, and potential utility of GM-CSF antagonists," *Proc. Assoc Amer Physic.* 108(6):420-431 (1996).
Nicola et al., "Neutralizing and Nonneutralizing Monoclonal Antibodies to the Human Granulocyte-Macrophage Colony-Stimulating Factor Receptor α-Chain," *Blood* 82(6):1724-1731 (1993).
Pascalis et al., "In vitro affinity maturation of a specificity-determining region-grafted humanized anticarcinoma antibody: isolation and characterization of minimally immunogenic high-affinity variants," *Clin Cancer Res* 9(15):5521-5531 (2003).
Raines et al., "Identification and molecular cloning of a soluble human granulocyte-Macrophage colony-stimulating factor receptor," *PNAS* 88:8203-8207 (1991).
Rajotte et al., "Crucial Role of the Residue R820 at the F'-G' Loop of the Humam Granulocyte/Macrophage Colony-stimulating Factor Receptor α Chain for Ligand Recognition," *J. Exp. Med.* 185(11):1939-1950 (1997).
Wu et al., "Stepwise in vitro affinity maturation of Vitaxin, an alphav beta3-specific humanized mAb," *PNAS* 95(11):6037-6042 (1998).
Zenyth Therapeutics information sheet on GM-CSF Receptor Antibody (2005).
MAB1037 data sheet "Mouse Anti-Human GM-CSF Alpha Receptor (Neutralizing) Monoclonal Antibody".

(Continued)

*Primary Examiner* — Christine J Saoud
*Assistant Examiner* — Jegatheesan Seharaseyon
(74) *Attorney, Agent, or Firm* — Klarquist Sparkman, LLP

(57) ABSTRACT

Binding members are provided for alpha chain of receptor for granulocyte macrophage colony stimulating factor (GM-CSFRα), especially antibody molecules. Use of the binding members in treating inflammatory and autoimmune diseases, e.g. rheumatoid arthritis, asthma, allergic response, multiple sclerosis, myeloid leukaemia and atherosclerosis is also provided.

10 Claims, 10 Drawing Sheets

OTHER PUBLICATIONS

Report "The effect of antibodies on the drop in neutrophils and monocytes caused by the injection of GM-CSF," Presentation in Melbourne, Australia (CAT/Zenyth/CSL meeting) (2006).

Hamilton, "Molecular Engineering: Applications to the Clinical Laboratory," *Clinical Chemistry* 39(9):1988-1997, 1993.

Rajpal et al., "A general method for greatly improving the affinity of antibodies by using combinatorial libraries," *PNAS* 102(24):8466-8471, 2005.

Shi et al., "Granulocyte-macrophage colony-stimulating factor (GM-CSF) and T-cell responses: what we do and don't know," *Cell Research* 16(2):126-133, 2006.

Smith et al., "Demystified . . . recombinant antibodies," *J. Clin. Pathol.*, 57(9):912-917, 2004.

Russian Examination Report, issued Feb. 28, 2012, in Application No. 2008137763/10(048646) (5 pages) (*English Translation Only*).

US 8,263,075 B2

ANTIBODY MOLECULE FOR HUMAN GM-CSF RECEPTOR ALPHA

REFERENCE TO RELATED APPLICATIONS

Applicants claim the benefit of the earlier filing date of U.S. Provisional Application No. 60/786,569 filed on Mar. 27, 2006. The entire disclosures of the provisional application and co-filed International application PCT/GB2007/001108, filed Mar. 27, 2007, are considered to be part of the present disclosure, and are incorporated herein by reference.

The present invention relates to binding members for the alpha chain of Granulocyte/Macrophage Colony Stimulating Factor Receptor (GM-CSFRα), especially anti-GMCSFRα antibody molecules. It also relates to use of these binding members in treating inflammatory, respiratory and autoimmune diseases mediated through GMCSFRα, including rheumatoid arthritis, chronic obstructive pulmonary disease and multiple sclerosis.

GM-CSF is a type I proinflammatory cytokine which enhances survival, proliferation and/or differentiation of a broad range of haematopoietic cell types including neutrophils, eosinophils, macrophages and their progenitor cells. The GM-CSF receptor is a member of the haematopoietic receptor superfamily. It is heterodimeric, consisting of an alpha and a beta subunit. The alpha subunit is highly specific for GM-CSF whereas the beta subunit is shared with other cytokine receptors, including IL3 and IL5. This is reflected in a broader tissue distribution of the beta receptor subunit. The alpha subunit, GM-CSFRα, is primarily expressed on myeloid cells and non-haematopoietic cells, such as neutrophils, macrophages, eosinophils, dendritic cells, endothelial cells and respiratory epithelial cells. Full length GM-CSFRα is a 400 amino acid type I membrane glycoprotein that belongs to the type I cytokine receptor family, and consists of a 22 amino acid signal peptide (positions 1-22), a 298 amino acid extracellular domain (positions 23-320), a transmembrane domain from positions 321-345 and a short 55 amino acid intra-cellular domain. The signal peptide is cleaved to provide the mature form of GM-CSFRα as a 378 amino acid protein. cDNA clones of the human and murine GM-CSFRα are available and, at the protein level, the receptor subunits have 36% identity. GM-CSF is able to bind with relatively low affinity to the α subunit alone (Kd 1-5 nM) but not at all to the β subunit alone. However, the presence of both α and β subunits results in a high affinity ligand-receptor complex (Kd≈100 pM). GM-CSF signalling occurs through its initial binding to the GM-CSFR α chain and then cross-linking with a larger subunit the common β chain to generate the high affinity interaction, which phosphorylates the JAK-STAT pathway. GM-CSFR binding to GMCSF is reviewed in ref. [1]. This interaction is also capable of signalling through tyrosine phosphorylation and activation of the MAP kinase pathway.

Pathologically, GM-CSF has been shown to play a role in exacerbating inflammatory, respiratory and autoimmune diseases. Neutralisation of GM-CSF binding to GM-CSFRα is therefore a therapeutic approach to treating diseases and conditions mediated through GM-CSFR.

Nicola et al. [2] described a murine antibody against human GM-CSFRα, designated 2B7-17-A or "2B7", which was reported to have a relatively high affinity for human GM-CSFRα and to be a potent inhibitor of human GM-CSF biological action in several different bioassays. Antibody 2B7 is available commercially from Chemicon as MAB1037, and the Product Data Sheet for MAB1037 notes it is a potent inhibitor of GM-CSF biological action. 2B7 was also disclosed in WO94/09149.

By using a combination of selections on naïve scFv phage libraries, random mutagenesis and appropriately designed biochemical and biological assays (see the Experimental Part below), we have identified highly potent antibody molecules that bind to human GM-CSFRα and inhibit the action of human GM-CSF at its receptor. The results presented herein indicate that our antibodies bind a different region or epitope of GM-CSFRα compared with the known anti-GM-CSFRα antibody 2B7, and surprisingly are even more potent than 2B7 as demonstrated in a variety of biological assays.

Accordingly, this invention relates to binding members that bind human GM-CSFRα and inhibit binding of human GM-CSF to GM-CSFRα. Binding members of the invention may be antagonists of GM-CSFR. The binding members may be competitive reversible inhibitors of GM-CSF signalling through GM-CSFR.

Antibodies and other binding members of the invention are of particular value in binding and neutralising GM-CSFRα, and thus are of use in treatments for diseases mediated by GM-CSFRα, including inflammatory and autoimmune diseases, as indicated by the experimentation contained herein and further supporting technical literature. For example, we have demonstrated in cell-based assays that antibodies of the invention are able to inhibit release of cytokines (e.g. IL-6 and TNFα) induced by native GM-CSF binding to its receptor. As explained in more detail below, inhibiting GM-CSF activity by blocking binding to GM-CSFRα is a therapeutic approach to treating such diseases as rheumatoid arthritis (RA), asthma, smoke-induced airway inflammation, chronic obstructive pulmonary disease (COPD), allergic response, multiple sclerosis (MS), myeloid leukaemia and atherosclerosis.

Binding members according to the invention generally bind the extracellular domain of GM-CSFRα. Preferably, a binding member of the invention binds at least one residue of Tyr-Leu-Asp-Phe-Gln (YLDFQ), SEQ ID NO: 201, at positions 226 to 230 of mature human GM-CSFRα (SEQ ID NO: 206). The binding member may bind at least one residue in the YLDFQ sequence of human GM-CSFRα, e.g. it may bind one, two, three or four residues of the YLDFQ sequence. Thus, the binding member may recognise one or more residues within this sequence, and optionally it may also bind additional flanking residues or structurally neighbouring residues in the extra-cellular domain of GM-CSFRα.

Binding may be determined by any suitable method, for example a peptide-binding scan may be used, such as a PEPSCAN-based enzyme linked immuno assay (ELISA), as described in detail elsewhere herein. In a peptide-binding scan, such as the kind provided by PEPSCAN Systems, short overlapping peptides derived from the antigen are systematically screened for binding to a binding member. The peptides may be covalently coupled to a support surface to form an array of peptides. Briefly, a peptide binding scan (e.g. "PEPSCAN") involves identifying (e.g. using ELISA) a set of peptides to which the binding member binds, wherein the peptides have amino acid sequences corresponding to fragments of SEQ ID NO: 206 (e.g. peptides of about 15 contiguous residues of SEQ ID NO: 206), and aligning the peptides in order to determine a footprint of residues bound by the binding member, where the footprint comprises residues common to overlapping peptides. In accordance with the invention, the footprint identified by the peptide-binding scan or PEPSCAN may comprise at least one residue of YLDFQ corresponding to positions 226 to 230 of SEQ ID NO: 206.

The footprint may comprise one, two, three, four or all residues of YLDFQ. A binding member according to the invention may bind a peptide fragment (e.g. of 15 residues) of SEQ ID NO: 206 comprising one or more, preferably all, of residues YLDFQ corresponding to positions 226 to 230 of SEQ ID NO: 206, e.g. as determined by a peptide-binding scan or PEPSCAN method described herein. Thus, a binding member of the invention may bind a peptide having an amino acid sequence of 15 contiguous residues of SEQ ID NO: 206, wherein the 15 residue sequence comprises at least one residue of, or at least partially overlaps with, YLDFQ at positions 226 to 230 of SEQ ID NO: 206. Details of a suitable peptide-binding scan method for determining binding are set out in detail elsewhere herein. Other methods which are well known in the art and could be used to determine the residues bound by an antibody, and/or to confirm peptide-binding scan (e.g. PEPSCAN) results, include site directed mutagenesis, hydrogen deuterium exchange, mass spectrometry, NMR, and X-ray crystallography.

Accordingly, a binding member of the invention preferably neutralises GM-CSFRα. Neutralisation means reduction or inhibition of biological activity of GM-CSFRα, e.g. reduction or inhibition of GM-CSF binding to GM-CSFRα, or of signalling by GM-CSFRα e.g. as measured by GM-CSFRα-mediated responses. The reduction or inhibition in biological activity may be partial or total. The degree to which an antibody neutralises GM-CSFRα is referred to as its neutralising potency. Potency may be determined or measured using one or more assays known to the skilled person and/or as described or referred to herein. For example, the binding member may have neutralising activity in one or more of the following assays:

- Biochemical ligand binding assay
- TF-1 proliferation assay
- Human granulocyte shape change assay
- Cynomolgus non human primate granulocyte shape change assay
- Monocyte TNFα release assay
- Granulocyte survival assay
- Colony formation assay (inhibition of in vitro GM-CSF mediated differentiation of blood cell progenitors)
- Inhibition of GM-CSF bioactivity in vivo e.g. in chimaeric mice with transgenic bone marrow expressing human GM-CSFR
- Peripheral blood mononuclear cell cytokine release assay Potency is normally expressed as an IC50 value, in pM unless otherwise stated. In functional assays, IC50 is the concentration that reduces a biological response by 50% of its maximum. In ligand-binding studies, IC50 is the concentration that reduces receptor binding by 50% of maximal specific binding level. IC50 may be calculated by plotting % maximal biological response (represented e.g. by cell proliferation, which may be measured as 3H thymidine incorporation in cpm, in a proliferation assay, by shape change in a shape change assay, by TNFα release in a TNFα release assay, by survival in a survival assay, by number of colonies in a colony formation assay, or by increase in spleen weight or decrease in circulating monocytes in chimaeric mice with transgenic bone marrow expressing human GM-CSFR in a bioactivity test) or % specific receptor binding as a function of the log of the binding member concentration, and using a software program such as Prism (GraphPad) to fit a sigmoidal function to the data to generate IC50 values.

An IC50 value may represent the mean of a plurality of measurements. Thus, for example, IC50 values may be obtained from the results of triplicate experiments, and a mean IC50 value can then be calculated.

In the TF-1 proliferation assay, binding members of the invention normally have an IC50 of less than 1500 pM. For example, the IC50 may be <300, <60, <10, or <1.5 pM e.g. about 1.0 pM. Normally IC50 is at least 0.5 or 1.0 nM. The known murine antibody 2B7 had an IC50 of about 1600 pM in this assay. The TF-1 proliferation assay used herein was with a final concentration of 7 pM human GM-CSF. Thus, IC50 neutralising potency in the TF-1 proliferation assay represents ability of a binding member to inhibit proliferation of TF-1 cells induced by 7 pM human GM-CSF. For more details see the Assay Methods and Materials section.

A binding member of the invention may have a $pA_2$ more negative than −6, −7, −8, −9, −10, −10.5 or −11 in the TF-1 proliferation assay. For example, $pA_2$ may be about −10.5 or −11. Calculation and significance of $pA_2$ values is discussed in detail in the Experimental Part under Assay Methods and Materials.

In the human granulocyte shape change assay, binding members of the invention normally have an IC50 of less than 100 pM, e.g. less than 50 pM or less than 30, 25, 20, 15 or 10 pM. Normally IC50 is at least 5, 6 or 7 pM. The known murine antibody 2B7 in contrast is less potent with a measured IC50 of 477 pM in this assay. The human granulocyte shape change assay used herein was with a final concentration of 7 pM human GM-CSF. Thus, IC50 neutralising potency in the human granulocyte shape change assay represents ability of a binding member to inhibit shape change of human granulocytes induced by 7 pM human GM-CSF. For more details see the Assay Methods and Materials section.

In the cynomolgus granulocyte shape change assay, binding members of the invention normally have an IC50 of less than 20 pM, typically less than 10, 5 or 2.5 pM. IC50 may be at least 0.5, 1 or 1.5 pM. The known murine antibody 2B7 had an IC50 of 26 pM when tested in this assay. The cynomolgus granulocyte shape change assay used herein was with a final concentration of 7 pM human GM-CSF. Thus, IC50 neutralising potency in the cynomolgus granulocyte shape change assay represents ability of a binding member to inhibit shape change of cynomolgus granulocytes induced by 7 human pM GM-CSF. For more details see the Assay Methods and Materials section.

A binding member of the invention may have a $pA_2$ more negative than −6, −7, −8, −9, −10, −10.5 or −11 in the human and/or cynomolgus shape change assay. Preferably the $pA_2$ is about −10 or −11.

In the monocyte TNFα release assay, binding members of the invention normally have an IC50 of less than 150 pM, typically less than 110 pM e.g. less than 100 pM. IC50 may be at least 30 or 40 pM. The monocyte TNFα release assay used herein was with a final concentration of 1 nM human GM-CSF. Thus, IC50 neutralising potency in the monocyte TNFα release assay represents ability of a binding member to inhibit TNFα release from human monocytes stimulated with 1 nM human GM-CSF. For more details see the Assay Methods and Materials section.

In the granulocyte survival assay, binding members of the invention normally have an IC50 of less than 1000 pM, typically less than 850 pM. IC50 may be less than 500, 250, 150, 100, 50, 30, 20 or 10 pM. IC50 may be at least 5 pM. The known murine antibody 2B7 is inactive in this assay up to a concentration of 83 nM. The granulocyte survival assay used herein was with a final concentration of 7 pM human GM-CSF. Thus, IC50 neutralising potency in the granulocyte survival assay represents ability of a binding member to inhibit survival of human granulocytes induced by 7 pM human GM-CSF. For more details see the Assay Methods and Materials section.

In the colony formation assay, binding members of the invention may have an IC50 of less than 5, less than 2.5, less than 1 or less than 0.3 µg/ml. Preferably the IC50 is 0.25 µg/ml or less, e.g. less than 0.1 µg/ml. IC50 may be at least 0.05 µg/ml. The known murine antibody 2B7 has little if any activity in this assay up to a concentration of 10 µg/ml (67 nM). The colony formation assay used herein was with a final concentration of 10 ng/ml human GM-CSF. Thus, IC50 neutralising potency in the colony formation assay represents ability of a binding member to inhibit colony formation induced by 10 ng/ml human GM-CSF. For more details see the Assay Methods and Materials section.

A binding member of the invention may show a dose dependent ability to inhibit increase in spleen weight and/or to inhibit a GM-CSF induced decrease in circulating monocytes in chimaeric mice with transgenic bone marrow expressing human GM-CSFR, that are treated with human GM-CSF. IC50 for inhibition of increased spleen weight may be less than 5, less than 2.5, less than 2, less than 1 or less than 0.75 mg/kg. IC50 may be at least 0.5 mg/kg in some embodiments.

Additionally, binding kinetics and affinity of binding members for human GM-CSFRα may be determined, for example by surface plasmon resonance e.g. using BIACORE®. Binding members of the invention normally have a KD of less than 5 nM and more preferably less than 4, 3, 2 or 1 nM. Preferably, KD is less than 0.9, 0.8, 0.7, 0.6, 0.5, 0.4, 0.3, 0.2 or 0.15 nM.

Binding members of the invention normally bind non-human primate GM-CSFRα e.g. cynomolgus GM-CSFRα in addition to human GM-CSFRα. As there is a low homology between human and murine GM-CSF receptor (approximately 36%), binding members of the invention will generally not bind or cross-react with the murine receptor.

Normally a binding member of the invention comprises an antibody molecule, e.g. a whole antibody or antibody fragment, as discussed in more detail below. Preferably, an antibody molecule of the invention is a human antibody molecule.

A binding member of the invention normally comprises an antibody VH and/or VL domain. VH domains and VL domains of binding members are also provided as part of the invention. Within each of the VH and VL domains are complementarity determining regions ("CDRs"), and framework regions, ("FRs"). A VH domain comprises a set of HCDRs and a VL domain comprises a set of LCDRs. An antibody molecule typically comprises an antibody VH domain comprising a VH CDR1, CDR2 and CDR3 and a framework. It may alternatively or also comprise an antibody VL domain comprising a VL CDR1, CDR2 and CDR3 and a framework. A VH or VL domain framework comprises four framework regions, FR1, FR2, FR3 and FR4, interspersed with CDRs in the following structure:

FR1-CDR1-FR2-CDR2-FR3-CDR3-FR4.

Examples of antibody VH and VL domains, FRs and CDRs according to the present invention are as listed in the appended sequence listing that forms part of the present disclosure. All VH and VL sequences, CDR sequences, sets of CDRs and sets of HCDRs and sets of LCDRs disclosed herein represent aspects and embodiments of the invention. Thus, an aspect of the invention is a VH domain of a binding member according to the invention. A "set of CDRs" comprises CDR1, CDR2 and CDR3. Thus, a set of HCDRs means HCDR1, HCDR2 and HCDR3, and a set of LCDRs means LCDR1, LCDR2 and LCDR3. Unless otherwise stated, a "set of CDRs" includes HCDRs and LCDRs. Typically binding members of the invention are monoclonal antibodies (mAb).

As described in more detail in the Experimental Part, we identified a panel of antibody molecules that bind GM-CSFRα. We also identified certain residues within the complementarity determining regions (CDRs) of the VH and VL domains that are especially important for receptor binding and neutralisation potency. Since the CDRs are primarily responsible for determining binding and specificity of a binding member, one or more CDRs having the appropriate residues as defined herein may be used and incorporated into any suitable framework, for example an antibody VH and/or VL domain framework, or a non-antibody protein scaffold, as described in more detail elsewhere herein. For example, one or more CDRs or a set of CDRs of an antibody may be grafted into a framework (e.g. human framework) to provide an antibody molecule or different antibody molecules. For example, an antibody molecule may comprise CDRs as disclosed herein and framework regions of human germline gene segment sequences. An antibody may be provided with a set of CDRs within a framework which may be subject to germlining, where one or more residues within the framework are changed to match the residues at the equivalent position in the most similar human germline framework. Thus, antibody framework regions are preferably germline and/or human.

We carried out an investigation into which residues of a candidate antibody were important for antigen recognition, following the method set out in the experimental section, and then performed sequence analysis of 160 clones showing a potency at least 5-fold higher than the parent antibody clone in a biological assay. The results indicated the following positions as contributing to antigen binding: Kabat residues 27A, 27B, 27C, 32, 51, 52, 53, 90, 92 and 96 in the VL domain and Kabat residues 17, 34, 54, 57, 95, 97, 99 and 100B in the VH domain. In preferred embodiments of the invention, one or more of these Kabat residues is the Kabat residue present at that position for one or more of the antibody clones numbered 1, 2 and 4-20 whose sequences are disclosed in the appended sequence listing. In various embodiments the residue may be the same as, or may differ from, the residue present at that position in antibody 3.

Our analysis indicated 4 residue positions in the CDRs that have a particularly strong influence on receptor binding: H97, H100B, L90 and L92 (Kabat numbering). Preferably, H97 of VH CDR3 is S. The serine residue at this position was observed in all 160 clones and therefore represents an important residue for antigen recognition.

Preferably, a VH CDR3 comprises one or more of the following residues:

V, N, A or L at Kabat residue H95, most preferably V;

S, F, H, P, T or W at Kabat residue H99, most preferably S;

A, T, P, S, V or H at Kabat residue H100B, most preferably A or T.

Preferably, Kabat residue H34 in VH CDR1 is I. Preferably, VH CDR2 comprises E at Kabat residue H54 and/or I at Kabat residue H57.

Where the binding member comprises an antibody VH domain, Kabat residue H17 in the VH domain framework is preferably S. Kabat residue H94 is preferably I or a conservative substitution thereof (e.g. L, V, A or M). Normally H94 is I.

Preferably, a VL CDR3 comprises one or more of the following residues:

S, T or M at Kabat residue L90, most preferably S or T;

D, E, Q, S, M or T at Kabat residue L92, most preferably D or E;

A, P, S, T, I, L, M or V at Kabat residue L96, most preferably S, P I or V, especially S.

Kabat residue L95A in VL CDR3 is preferably S.

Preferably, a VL CDR1 comprises one or more of the following residues:
S at Kabat residue 27A;
N at Kabat residue 27B;
I at Kabat residue 27C;
D at Kabat residue 32.

Preferably, a VL CDR2 comprises one or more of the following residues:
N at Kabat residue 51;
N at Kabat residue 52;
K at Kabat residue 53.

In a preferred embodiment, a binding member of the invention comprises one or more CDRs selected from the VH and VL CDRs, i.e. a VH CDR1, 2 and/or 3 and/or a VL CDR 1, 2 and/or 3 of any of antibodies 1, 2 or 4 to 20 as shown in the sequence listing, or of the parent antibody 3. In a preferred embodiment a binding member of the invention comprises a VH CDR3 of any of the following antibody molecules: Antibody 1 (SEQ ID NO 5); Antibody 2 (SEQ ID NO 15); Antibody 3 (SEQ ID NO 25); Antibody 4 (SEQ ID NO 35); Antibody 5 (SEQ ID NO 45); Antibody 6 (SEQ ID NO 55); Antibody 7 (SEQ ID NO 65); Antibody 8 (SEQ ID NO 75); Antibody 9 (SEQ ID NO 85); Antibody 10 (SEQ ID NO 95); Antibody 11 (SEQ ID NO 105); Antibody 12 (SEQ ID NO 115); Antibody 13 (SEQ ID NO 125); Antibody 14 (SEQ ID NO 135); Antibody 15 (SEQ ID NO 145); Antibody 16 (SEQ ID NO 155); Antibody 17 (SEQ ID NO 165); Antibody 18 (SEQ ID NO 175); Antibody 19 (SEQ ID NO 185); Antibody 20 (SEQ ID NO 195). Preferably, the binding member additionally comprises a VH CDR1 of SEQ ID NO: 3 or SEQ ID NO: 173 and/or a VH CDR2 of SEQ ID NO: 4. Preferably, a binding member comprising VH CDR3 of SEQ ID NO: 175 comprises a VH CDR1 of SEQ ID NO: 173, but may alternatively comprise a VH CDR1 of SEQ ID NO: 3.

Preferably the binding member comprises a set of VH CDRs of one of the following antibodies: Antibody 1 (SEQ ID NOS: 3-5); Antibody 2 (SEQ ID NOS: 3, 4, 15); Antibody 3 (SEQ ID NOS: 3, 4, 25); Antibody 4 (SEQ ID NOS: 3, 4, 35); Antibody 5 (SEQ ID NOS: 3, 4, 45); Antibody 6 (SEQ ID NOS: 3, 4, 55); Antibody 7 (SEQ ID NOS: 3, 4, 65); Antibody 8 (SEQ ID NOS: 3, 4, 75); Antibody 9 (SEQ ID NOS: 3, 4, 85); Antibody 10 (SEQ ID NOS: 3, 4, 95); Antibody 11 (SEQ ID NOS: 3, 4, 105); Antibody 12 (SEQ ID NOS: 3, 4, 115); Antibody 13 (SEQ ID NOS: 3, 4, 125); Antibody 14 (SEQ ID NOS: 3, 4, 135); Antibody 15 (SEQ ID NOS: 3, 4, 145); Antibody 16 (SEQ ID NOS: 3, 4, 155); Antibody 17 (SEQ ID NOS: 3, 4, 165); Antibody 18 (SEQ ID NOS: 173, 4, 175); Antibody 19 (SEQ ID NOS: 3, 4, 185); Antibody 20 (SEQ ID NOS: 3, 4, 195). Optionally it may also comprise a set of VL CDRs of one of these antibodies, and the VL CDRs may be from the same or a different antibody as the VH CDRs. Generally, a VH domain is paired with a VL domain to provide an antibody antigen-binding site, although in some embodiments a VH or VL domain alone may be used to bind antigen. Light-chain promiscuity is well established in the art, and thus the VH and VL domain need not be from the same clone as disclosed herein.

A binding member may comprise a set of H and/or L CDRs of any of antibodies 1 to 20 with one or more substitutions, for example ten or fewer, e.g. one, two, three, four or five, substitutions within the disclosed set of H and/or L CDRs. Preferred substitutions are at Kabat residues other than Kabat residues 27A, 27B, 27C, 32, 51, 52, 53, 90, 92 and 96 in the VL domain and Kabat residues 34, 54, 57, 95, 97, 99 and 100B in the VH domain. Where substitutions are made at these positions, the substitution is preferably for a residue indicated herein as being a preferred residue at that position.

In a preferred embodiment, a binding member of the invention is an isolated human antibody molecule having a VH domain comprising a set of HCDRs in a human germline framework, e.g. human germline framework from the heavy chain VH1 or VH3 family. In a preferred embodiment, the isolated human antibody molecule has a VH domain comprising a set of HCDRs in a human germline framework VH1 DP5 or VH3 DP47. Thus, the VH domain framework regions may comprise framework regions of human germline gene segment VH1 DP5 or VH3 DP47. The amino acid sequence of VH FR1 may be SEQ ID NO: 251. The amino acid sequence of VH FR2 may be SEQ ID NO: 252. The amino acid sequence of VH FR3 may be SEQ ID NO: 253. The amino acid sequence of VH FR4 may be SEQ ID NO: 254.

Normally the binding member also has a VL domain comprising a set of LCDRs, preferably in a human germline framework e.g. a human germline framework from the light chain Vlambda 1 or Vlambda 6 family. In a preferred embodiment, the isolated human antibody molecule has a VL domain comprising a set of LCDRs in a human germline framework VLambda 1 DPL8 or VLambda 1 DPL3 or VLambda 6_6a. Thus, the VL domain framework may comprise framework regions of human germline gene segment VLambda 1 DPL8, VLambda 1 DPL3 or VLambda 6_6a. The VL domain FR4 may comprise a framework region of human germline gene segment JL2. The amino acid sequence of VL FR1 may be SEQ ID NO: 255. The amino acid sequence of VL FR2 may be SEQ ID NO: 256. The amino acid sequence of VL FR3 may be 257. The amino acid sequence of VL FR4 may be SEQ ID NO: 258.

A non-germlined antibody has the same CDRs, but different frameworks, compared with a germlined antibody.

A binding member of the invention may compete for binding to GM-CSFRα with any binding member disclosed herein e.g. antibody 3 or any of antibodies 1, 2 or 4-20. Thus a binding member may compete for binding to GM-CSFRα with an antibody molecule comprising the VH domain and VL domain of any of antibodies 1, 2 or 4-20. Competition between binding members may be assayed easily in vitro, for example by tagging a reporter molecule to one binding member which can be detected in the presence of one or more other untagged binding members, to enable identification of binding members which bind the same epitope or an overlapping epitope.

Competition may be determined for example using ELISA in which e.g. the extracellular domain of GM-CSFRα, or a peptide of the extracellular domain, is immobilised to a plate and a first tagged binding member along with one or more other untagged binding members is added to the plate. Presence of an untagged binding member that competes with the tagged binding member is observed by a decrease in the signal emitted by the tagged binding member. Similarly, a surface plasmon resonance assay may be used to determine competition between binding members.

In testing for competition a peptide fragment of the antigen may be employed, especially a peptide including or consisting essentially of an epitope or binding region of interest. A peptide having the epitope or target sequence plus one or more amino acids at either end may be used. Binding members according to the present invention may be such that their binding for antigen is inhibited by a peptide with or including the sequence given.

Binding members that bind a peptide may be isolated for example from a phage display library by panning with the peptide(s).

The present invention also provides the use of a binding member as above for measuring antigen levels in a competition assay, that is to say a method of measuring the level of antigen in a sample by employing a binding member as provided by the present invention in a competition assay. This may be where the physical separation of bound from unbound antigen is not required. Linking a reporter molecule to the binding member so that a physical or optical change occurs on binding is one possibility. The reporter molecule may directly or indirectly generate detectable, and preferably measurable, signals. The linkage of reporter molecules may be directly or indirectly, covalently, e.g. via a peptide bond or non-covalently. Linkage via a peptide bond may be as a result of recombinant expression of a gene fusion encoding antibody and reporter molecule.

The present invention also provides for measuring levels of antigen directly, by employing a binding member according to the invention for example in a biosensor system.

The present invention provides a method comprising causing or allowing binding of a binding member as provided herein to GM-CSFRα. Such binding may take place in vivo, e.g. following administration of a binding member, or nucleic acid encoding a binding member, or it may take place in vitro, for example in ELISA, Western blotting, immunocytochemistry, immuno-precipitation, affinity chromatography, or cell based assays such as a TF-1 assay.

The amount of binding of binding member to GM-CSFRα may be determined. Quantitation may be related to the amount of the antigen in a test sample, which may be of diagnostic or prognostic interest.

A kit comprising a binding member or antibody molecule according to any aspect or embodiment of the present invention is also provided as an aspect of the present invention. In a kit of the invention, the binding member or antibody molecule may be labelled to allow its reactivity in a sample to be determined, e.g. as described further below. Components of a kit are generally sterile and in sealed vials or other containers. Kits may be employed in diagnostic analysis or other methods for which antibody molecules are useful. A kit may contain instructions for use of the components in a method, e.g. a method in accordance with the present invention. Ancillary materials to assist in or to enable performing such a method may be included within a kit of the invention.

The reactivities of antibodies in a sample may be determined by any appropriate means. Radioimmunoassay (RIA) is one possibility. Radioactive labelled antigen is mixed with unlabelled antigen (the test sample) and allowed to bind to the antibody. Bound antigen is physically separated from unbound antigen and the amount of radioactive antigen bound to the antibody determined. The more antigen there is in the test sample the less radioactive antigen will bind to the antibody. A competitive binding assay may also be used with non-radioactive antigen, using antigen or an analogue linked to a reporter molecule. The reporter molecule may be a fluorochrome, phosphor or laser dye with spectrally isolated absorption or emission characteristics. Suitable fluorochromes include fluorescein, rhodamine, phycoerythrin and Texas Red. Suitable chromogenic dyes include diaminobenzidine. Other reporters include macromolecular colloidal particles or particulate material such as latex beads that are coloured, magnetic or paramagnetic, and biologically or chemically active agents that can directly or indirectly cause detectable signals to be visually observed, electronically detected or otherwise recorded. These molecules may be enzymes, which catalyse reactions that develop, or change colours or cause changes in electrical properties, for example. They may be molecularly excitable, such that electronic transitions between energy states result in characteristic spectral absorptions or emissions. They may include chemical entities used in conjunction with biosensors. Biotin/avidin or biotin/streptavidin and alkaline phosphatase detection systems may be employed.

The signals generated by individual antibody-reporter conjugates may be used to derive quantifiable absolute or relative data of the relevant antibody binding in samples (normal and test).

In further aspects, the invention provides an isolated nucleic acid which comprises a sequence encoding a binding member, VH domain and/or VL domain according to the present invention. Nucleic acid may include DNA and/or RNA, and may be wholly or partially synthetic. Reference to a nucleotide sequence as set out herein encompasses a DNA molecule with the specified sequence, and encompasses a RNA molecule with the specified sequence in which U is substituted for T, unless context requires otherwise. In a preferred aspect, the present invention provides a nucleic acid that codes for a CDR or set of CDRs or VH domain or VL domain or antibody antigen-binding site or antibody molecule, e.g. scFv or IgG1 or IgG4, of the invention as defined herein. The present invention also provides constructs in the form of plasmids, vectors, transcription or expression cassettes which comprise at least one polynucleotide as above.

A further aspect is a host cell transformed with or containing nucleic acid of the invention. Such a host cell may be in vitro and may be in culture. Such a host cell may be in vivo. In vivo presence of the host cell may allow intracellular expression of the binding members of the present invention as "intrabodies" or intracellular antibodies. Intrabodies may be used for gene therapy.

A still further aspect provides a method comprising introducing such nucleic acid into a host cell. The introduction may employ any available technique. For eukaryotic cells, suitable techniques may include calcium phosphate transfection, DEAE-Dextran, electroporation, liposome-mediated transfection and transduction using retrovirus or other virus, e.g. vaccinia or, for insect cells, baculovirus. Introducing nucleic acid in the host cell, in particular a eukaryotic cell may use a viral or a plasmid based system. The plasmid system may be maintained episomally or may be incorporated into the host cell or into an artificial chromosome. Incorporation may be either by random or targeted integration of one or more copies at single or multiple loci. For bacterial cells, suitable techniques may include calcium chloride transformation, electroporation and transfection using bacteriophage.

The introduction may be followed by causing or allowing expression from the nucleic acid, e.g. by culturing host cells under conditions for expression of the gene.

In one embodiment, the nucleic acid of the invention is integrated into the genome (e.g. chromosome) of the host cell. Integration may be promoted by inclusion of sequences that promote recombination with the genome, in accordance with standard techniques.

The present invention also provides a method that comprises using a construct as stated above in an expression system in order to express a binding member or polypeptide as above. Thus, methods of preparing a binding member, a VH domain and/or a VL domain of the invention, are further aspects of the invention. A method may comprise expressing said nucleic acid under conditions to bring about production of said binding member, VH domain and/or VL domain, and recovering it. Such a method may comprise culturing host cells under conditions for production of said binding member or antibody domain.

A method of production may comprise a step of isolation and/or purification of the product. A method of production may comprise formulating the product into a composition including at least one additional component, such as a pharmaceutically acceptable excipient.

Systems for cloning and expression of a polypeptide in a variety of different host cells are well known. Suitable host cells include bacteria, mammalian cells, plant cells, yeast and baculovirus systems and transgenic plants and animals. The expression of antibodies and antibody fragments in prokaryotic cells is well established in the art [3]. A common, preferred bacterial host is E. coli.

Expression in eukaryotic cells in culture is also available to those skilled in the art as an option for production of a binding member [4,5,6]. Mammalian cell lines available in the art for expression of a heterologous polypeptide include Chinese hamster ovary (CHO) cells, HeLa cells, baby hamster kidney cells, NS0 mouse melanoma cells, YB2/0 rat myeloma cells, human embryonic kidney cells, human embryonic retina cells and many others.

Suitable vectors can be chosen or constructed, containing appropriate regulatory sequences, including promoter sequences, terminator sequences, polyadenylation sequences, enhancer sequences, marker genes and other sequences as appropriate. Vectors may be plasmids e.g. phagemid, or viral e.g. 'phage, as appropriate [7]. Many known techniques and protocols for manipulation of nucleic acid, for example in preparation of nucleic acid constructs, mutagenesis, sequencing, introduction of DNA into cells and gene expression, and analysis of proteins, are described in detail in Ausubel et al. [8].

The present invention provides a method of obtaining one or more binding members able to bind the antigen, the method including bringing into contact a library of binding members according to the invention and said antigen, and selecting one or more binding members of the library able to bind said antigen.

The library may be displayed on particles or molecular complexes, e.g. replicable genetic packages such as yeast, bacterial or bacteriophage (e.g. T7) particles, or covalent, ribosomal or other in vitro display systems, each particle or molecular complex containing nucleic acid encoding the antibody VH variable domain displayed on it, and optionally also a displayed VL domain if present. Following selection of binding members able to bind the antigen and displayed on bacteriophage or other library particles or molecular complexes, nucleic acid may be taken from a bacteriophage or other particle or molecular complex displaying a said selected binding member. Such nucleic acid may be used in subsequent production of a binding member or an antibody VH or VL variable domain by expression from nucleic acid with the sequence of nucleic acid taken from a bacteriophage or other particle or molecular complex displaying a said selected binding member.

An antibody VH variable domain with the amino acid sequence of an antibody VH variable domain of a said selected binding member may be provided in isolated form, as may a binding member comprising such a VH domain.

An antibody VL variable domain with the amino acid sequence of an antibody VL variable domain of a said selected binding member may be provided in isolated form, as may a binding member comprising such a VL domain.

Ability to bind GM-CSFRα may be further tested, also ability to compete with any of antibodies 1 to 20 (e.g. in scFv format and/or IgG format, e.g. IgG1 or IgG4) for binding to GM-CSFRα. Ability to neutralise GM-CSFRα may be tested.

Variants of the VH and VL domains and CDRs of the present invention, including those for which amino acid sequences are set out herein can be obtained by means of methods of sequence alteration or mutation and screening, and can be employed in binding members for GM-CSFRα. Following the lead of computational chemistry in applying multivariate data analysis techniques to the structure/property-activity relationships [9] quantitative activity-property relationships of antibodies can be derived using well-known mathematical techniques such as statistical regression, pattern recognition and classification [10,11,12,13,14,15]. The properties of antibodies can be derived from empirical and theoretical models (for example, analysis of likely contact residues or calculated physicochemical property) of antibody sequence, functional and three-dimensional structures and these properties can be considered singly and in combination.

An antibody antigen-binding site composed of a VH domain and a VL domain is formed by six loops of polypeptide: three from the light chain variable domain (VL) and three from the heavy chain variable domain (VH). Analysis of antibodies of known atomic structure has elucidated relationships between the sequence and three-dimensional structure of antibody combining sites [16,17]. These relationships imply that, except for the third region (loop) in VH domains, binding site loops have one of a small number of main-chain conformations: canonical structures. The canonical structure formed in a particular loop has been shown to be determined by its size and the presence of certain residues at key sites in both the loop and in framework regions [16,17].

This study of sequence-structure relationship can be used for prediction of those residues in an antibody of known sequence, but of an unknown three-dimensional structure, which are important in maintaining the three-dimensional structure of its CDR loops and hence maintain binding. These predictions can be backed up by comparison of the predictions to the output from lead optimization experiments. In a structural approach, a model can be created of the antibody molecule [18] using any freely available or commercial package such as WAM [19]. A protein visualisation and analysis software package such as Insight II (Accelrys, Inc.) or Deep View [20] may then be used to evaluate possible substitutions at each position in the CDR. This information may then be used to make substitutions likely to have a minimal or beneficial effect on activity.

The techniques required to make substitutions within amino acid sequences of CDRs, antibody VH or VL domains and binding members generally are available in the art. Variant sequences may be made, with substitutions that may or may not be predicted to have a minimal or beneficial effect on activity, and tested for ability to bind and/or neutralise GM-CSFRα and/or for any other desired property.

Variable domain amino acid sequence variants of any of the VH and VL domains whose sequences are specifically disclosed herein may be employed in accordance with the present invention, as discussed. Particular variants may include one or more amino acid sequence alterations (addition, deletion, substitution and/or insertion of an amino acid residue), may be less than about 20 alterations, less than about 15 alterations, less than about 10 alterations or less than about 5 alterations, maybe 5, 4, 3, 2 or 1. Alterations may be made in one or more framework regions and/or one or more CDRs.

Preferably alterations do not result in loss of function, so a binding member comprising a thus-altered amino acid sequence preferably retains an ability to bind and/or neutralise GM-CSFRα. More preferably, it retains the same quantitative binding and/or neutralising ability as a binding member in which the alteration is not made, e.g. as measured in an assay described herein. Most preferably, the binding member comprising a thus-altered amino acid sequence has an improved ability to bind or neutralise GM-CSFRα compared with a binding member in which the alteration is not made, e.g. as measured in an assay described herein.

Alteration may comprise replacing one or more amino acid residue with a non-naturally occurring or non-standard amino acid, modifying one or more amino acid residue into a non-naturally occurring or non-standard form, or inserting one or more non-naturally occurring or non-standard amino acid into the sequence. Preferred numbers and locations of alterations in sequences of the invention are described elsewhere herein. Naturally occurring amino acids include the 20 "standard" L-amino acids identified as G, A, V, L, I, M, P, F, W, S, T, N, Q, Y, C, K, R, H, D, E by their standard single-letter codes. Non-standard amino acids include any other residue that may be incorporated into a polypeptide backbone or result from modification of an existing amino acid residue. Non-standard amino acids may be naturally occurring or non-naturally occurring. Several naturally occurring non-standard amino acids are known in the art, such as 4-hydroxyproline, 5-hydroxylysine, 3-methylhistidine, N-acetylserine, etc. [21]. Those amino acid residues that are derivatised at their N-alpha position will only be located at the N-terminus of an amino-acid sequence. Normally in the present invention an amino acid is an L-amino acid, but in some embodiments it may be a D-amino acid. Alteration may therefore comprise modifying an L-amino acid into, or replacing it with, a D-amino acid. Methylated, acetylated and/or phosphorylated forms of amino acids are also known, and amino acids in the present invention may be subject to such modification.

Amino acid sequences in antibody domains and binding members of the invention may comprise non-natural or non-standard amino acids described above. In some embodiments non-standard amino acids (e.g. D-amino acids) may be incorporated into an amino acid sequence during synthesis, while in other embodiments the non-standard amino acids may be introduced by modification or replacement of the "original" standard amino acids after synthesis of the amino acid sequence.

Use of non-standard and/or non-naturally occurring amino acids increases structural and functional diversity, and can thus increase the potential for achieving desired GM-CSFRα binding and neutralising properties in a binding member of the invention. Additionally, D-amino acids and analogues have been shown to have better pharmacokinetic profiles compared with standard L-amino acids, owing to in vivo degradation of polypeptides having L-amino acids after administration to an animal.

As noted above, a CDR amino acid sequence substantially as set out herein is preferably carried as a CDR in a human antibody variable domain or a substantial portion thereof. The HCDR3 sequences substantially as set out herein represent preferred embodiments of the present invention and it is preferred that each of these is carried as a HCDR3 in a human heavy chain variable domain or a substantial portion thereof.

Variable domains employed in the invention may be obtained or derived from any germline or rearranged human variable domain, or may be a synthetic variable domain based on consensus or actual sequences of known human variable domains. A CDR sequence of the invention (e.g. CDR3) may be introduced into a repertoire of variable domains lacking a CDR (e.g. CDR3), using recombinant DNA technology.

For example, Marks et al. (1992) [22] describe methods of producing repertoires of antibody variable domains in which consensus primers directed at or adjacent to the 5' end of the variable domain area are used in conjunction with consensus primers to the third framework region of human VH genes to provide a repertoire of VH variable domains lacking a CDR3. Marks et al. further describe how this repertoire may be combined with a CDR3 of a particular antibody. Using analogous techniques, the CDR3-derived sequences of the present invention may be shuffled with repertoires of VH or VL domains lacking a CDR3, and the shuffled complete VH or VL domains combined with a cognate VL or VH domain to provide binding members of the invention. The repertoire may then be displayed in a suitable host system such as the phage display system of WO92/01047 or any of a subsequent large body of literature, including ref. [23], so that suitable binding members may be selected. A repertoire may consist of from anything from $10^4$ individual members upwards, for example from $10^6$ to $10^8$ or $10^{10}$ members. Other suitable host systems include yeast display, bacterial display, T7 display, viral display, cell display, ribosome display and covalent display. Analogous shuffling or combinatorial techniques are also disclosed by Stemmer (1994) [24], who describes the technique in relation to a β-lactamase gene but observes that the approach may be used for the generation of antibodies.

A further alternative is to generate novel VH or VL regions carrying CDR-derived sequences of the invention using random mutagenesis of one or more selected VH and/or VL genes to generate mutations within the entire variable domain. Such a technique is described by Gram et al. (1992) [25], who used error-prone PCR. In preferred embodiments one or two amino acid substitutions are made within a set of HCDRs and/or LCDRs. Another method that may be used is to direct mutagenesis to CDR regions of VH or VL genes [26,27].

A further aspect of the invention provides a method for obtaining an antibody antigen-binding site for GM-CSFRα antigen, the method comprising providing by way of addition, deletion, substitution or insertion of one or more amino acids in the amino acid sequence of a VH domain set out herein a VH domain which is an amino acid sequence variant of the VH domain, optionally combining the VH domain thus provided with one or more VL domains, and testing the VH domain or VH/VL combination or combinations to identify a binding member or an antibody antigen-binding site for GM-CSFRα antigen and optionally with one or more preferred properties, preferably ability to neutralise GM-CSFRα activity. Said VL domain may have an amino acid sequence which is substantially as set out herein.

An analogous method may be employed in which one or more sequence variants of a VL domain disclosed herein are combined with one or more VH domains.

A further aspect of the invention provides a method of preparing a binding member for GM-CSFRα antigen, which method comprises:

(a) providing a starting repertoire of nucleic acids encoding a VH domain which either include a CDR3 to be replaced or lack a CDR3 encoding region;

(b) combining said repertoire with a donor nucleic acid encoding an amino acid sequence substantially as set out herein for a VH CDR3 such that said donor nucleic acid is inserted into the CDR3 region in the repertoire, so as to provide a product repertoire of nucleic acids encoding a VH domain;

(c) expressing the nucleic acids of said product repertoire;

(d) selecting a binding member for GM-CSFRα; and (e) recovering said binding member or nucleic acid encoding it.

Again, an analogous method may be employed in which a VL CDR3 of the invention is combined with a repertoire of nucleic acids encoding a VL domain that either include a CDR3 to be replaced or lack a CDR3 encoding region.

Similarly, one or more, or all three CDRs may be grafted into a repertoire of VH or VL domains that are then screened for a binding member or binding members for GM-CSFRα.

In a preferred embodiment, one or more HCDR1, HCDR2 and HCDR3, e.g. a set of HCDRs of Antibody 1 (SEQ ID NOS: 3-5); Antibody 2 (SEQ ID NOS: 3, 4, 15); Antibody 4 (SEQ ID NOS: 3, 4, 35); Antibody 5 (SEQ ID NOS: 3, 4, 45); Antibody 6 (SEQ ID NOS: 3, 4, 55); Antibody 7 (SEQ ID NOS: 3, 4, 65); Antibody 8 (SEQ ID NOS: 3, 4, 75); Antibody 9 (SEQ ID NOS: 3, 4, 85); Antibody 10 (SEQ ID NOS: 3, 4, 95); Antibody 11 (SEQ ID NOS: 3, 4, 105); Antibody 12 (SEQ ID NOS: 3, 4, 115); Antibody 13 (SEQ ID NOS: 3, 4, 125); Antibody 14 (SEQ ID NOS: 3, 4, 135); Antibody 15 (SEQ ID NOS: 3, 4, 145); Antibody 16 (SEQ ID NOS: 3, 4, 155); Antibody 17 (SEQ ID NOS: 3, 4, 165); Antibody 18 (SEQ ID NOS: 173, 4, 175); Antibody 19 (SEQ ID NOS: 3, 4, 185) or Antibody 20 (SEQ ID NOS: 3, 4, 195); or optionally Antibody 3 (SEQ ID NOS: 3, 4, 25), may be employed, and/or one or more LCDR1, LCDR2 and LCDR3 e.g. a set of LCDRs of Antibody 1 (SEQ ID NOS: 8-10); Antibody 2 (SEQ ID NOS: 8, 9, 20); Antibody 4 (SEQ ID NOS: 8, 9, 20); Antibody 5 (SEQ ID NOS: 8, 9, 20); Antibody 6 (SEQ ID NOS: 8, 9, 60); Antibody 7 (SEQ ID NOS: 8, 9, 20); Antibody 8 (SEQ ID NOS: 8, 9, 20); Antibody 9 (SEQ ID NOS: 8, 9, 20); Antibody 10 (SEQ ID NOS: 8, 9, 20); Antibody 11 (SEQ ID NOS: 8, 9, 20); Antibody 12 (SEQ ID NOS: 8, 9, 120); Antibody 13 (SEQ ID NOS: 8, 9, 130); Antibody 14 (SEQ ID NOS: 8, 9, 140); Antibody 15 (SEQ ID NOS: 8, 9, 150); Antibody 16 (SEQ ID NOS: 8, 9, 160); Antibody 17 (SEQ ID NOS: 8, 9, 170); Antibody 18 (SEQ ID NOS: 8, 9, 180); Antibody 19 (SEQ ID NOS: 8, 9, 190) or Antibody 20 (SEQ ID NOS: 8, 9, 200); or optionally Antibody 3 (SEQ ID NOS: 8, 9, 20), may be employed.

A substantial portion of an immunoglobulin variable domain will comprise at least the three CDR regions, together with their intervening framework regions. Preferably, the portion will also include at least about 50% of either or both of the first and fourth framework regions, the 50% being the C-terminal 50% of the first framework region and the N-terminal 500 of the fourth framework region. Additional residues at the N-terminal or C-terminal end of the substantial part of the variable domain may be those not normally associated with naturally occurring variable domain regions. For example, construction of binding members of the present invention made by recombinant DNA techniques may result in the introduction of N- or C-terminal residues encoded by linkers introduced to facilitate cloning or other manipulation steps. Other manipulation steps include the introduction of linkers to join variable domains of the invention to further protein sequences including antibody constant regions, other variable domains (for example in the production of diabodies) or detectable/functional labels as discussed in more detail elsewhere herein.

Although in a preferred aspect of the invention binding members comprising a pair of VH and VL domains are preferred, single binding domains based on either VH or VL domain sequences form further aspects of the invention. It is known that single immunoglobulin domains, especially VH domains, are capable of binding target antigens. For example, see the discussion of dAbs elsewhere herein.

In the case of either of the single binding domains, these domains may be used to screen for complementary domains capable of forming a two-domain binding member able to bind GM-CSFRα. This may be achieved by phage display screening methods using the so-called hierarchical dual combinatorial approach as disclosed in WO92/01047, in which an individual colony containing either an H or L chain clone is used to infect a complete library of clones encoding the other chain (L or H) and the resulting two-chain binding member is selected in accordance with phage display techniques such as those described in that reference and [22].

Further aspects of the present invention provide for compositions containing binding members of the invention and at least one additional component, e.g. a composition comprising a binding member and a pharmaceutically acceptable excipient. Such compositions may be used in methods of inhibiting or neutralising GM-CSFRα, including methods of treatment of the human or animal body by therapy.

The invention provides heterogeneous preparations comprising anti-GM-CSFRα antibody molecules. For example, such preparations may be mixtures of antibodies with full-length heavy chains and heavy chains lacking the C-terminal lysine, with various degrees of glycosylation and/or with derivatized amino acids, such as cyclization of an N-terminal glutamic acid to form a pyroglutamic acid residue.

Aspects of the invention include methods of treatment comprising administration of a binding member as provided, pharmaceutical compositions comprising such a binding member, and use of such a binding member in the manufacture of a medicament, for example in a method of making a medicament or pharmaceutical composition comprising formulating the binding member with a pharmaceutically acceptable excipient.

Anti-GM-CSFRα treatment may be given orally (for example nanobodies), by injection (for example, subcutaneously, intravenously, intra-arterially, intra-articularly, intraperitoneal or intramuscularly), by inhalation, by the intravesicular route (instillation into the urinary bladder), or topically (for example intraocular, intranasal, rectal, into wounds, on skin). The treatment may be administered by pulse infusion, particularly with declining doses of the binding member. The route of administration can be determined by the physicochemical characteristics of the treatment, by special considerations for the disease or by the requirement to optimise efficacy or to minimise side-effects. It is envisaged that anti-GM-CSFRα treatment will not be restricted to use in the clinic. Therefore, subcutaneous injection using a needle free device is also preferred.

A composition may be administered alone or in combination with other treatments, either simultaneously or sequentially dependent upon the condition to be treated. Combination treatments may be used to provide significant synergistic effects, particularly the combination of an anti-GM-CSFRα binding member with one or more other drugs. A binding member according to the present invention may be provided in combination or addition to one or more of the following: NSAIDs (e.g. cox inhibitors such as Celecoxib and other similar cox2 inhibitors), corticosteroids (e.g. prednisone) and disease-modifying antirheumatic drugs (DMARDs) e.g. HUMIRA® (adalimumab), methotrexate, ARAVA®, ENBREL® (Etanercept), REMICADE® (Infliximab), KINERET® (Anakinra), RITUXAN® (Rituximab), ORENCIA® (abatacept), gold salts, antimalarials, sulfasalazine, d-penicillamine, cyclosporin A, diclofenac, cyclophosphamide and azathioprine.

In accordance with the present invention, compositions provided may be administered to individuals. Administration is preferably in a "therapeutically effective amount", this being sufficient to show benefit to a patient. Such benefit may be at least amelioration of at least one symptom. The actual amount administered, and rate and time-course of administration, will depend on the nature and severity of what is being treated. Prescription of treatment, e.g. decisions on dosage etc, is within the responsibility of general practitioners and other medical doctors, and may depend on the severity of the symptoms and/or progression of a disease being treated. Appropriate doses of antibody are well known in the art [28,29]. Specific dosages indicated herein, or in the Physician's Desk Reference (2003) as appropriate for the type of medicament being administered, may be used. A therapeutically effective amount or suitable dose of a binding member of the invention can be determined by comparing its in vitro activity and in vivo activity in an animal model. Methods for extrapolation of effective dosages in mice and other test animals to humans are known. The precise dose will depend upon a number of factors, including whether the antibody is for diagnosis or for treatment, the size and location of the area to be treated, the precise nature of the antibody (e.g. whole antibody, fragment or diabody), and the nature of any detectable label or other molecule attached to the antibody. A typical antibody dose will be in the range 100 μg to 1 g for systemic applications, and 1 μg to 1 mg for topical applications. Typically, the antibody will be a whole antibody, preferably IgG1, IgG2 or more preferably IgG4. This is a dose for a single treatment of an adult patient, which may be proportionally adjusted for children and infants, and also adjusted for other antibody formats in proportion to molecular weight. Treatments may be repeated at daily, twice-weekly, weekly or monthly intervals, at the discretion of the physician. In preferred embodiments of the present invention, treatment is periodic, and the period between administrations is about two weeks or more, preferably about three weeks or more, more preferably about four weeks or more, or about once a month. In other preferred embodiments of the invention, treatment may be given before, and/or after surgery, and more preferably, may be administered or applied directly at the anatomical site of surgical treatment.

Binding members of the present invention will usually be administered in the form of a pharmaceutical composition, which may comprise at least one component in addition to the binding member. Thus pharmaceutical compositions according to the present invention, and for use in accordance with the present invention, may comprise, in addition to active ingredient, a pharmaceutically acceptable excipient, carrier, buffer, stabiliser or other materials well known to those skilled in the art. Such materials should be non-toxic and should not interfere with the efficacy of the active ingredient.

The precise nature of the carrier or other material will depend on the route of administration, which may be oral, or by injection, e.g. intravenous. Pharmaceutical compositions for oral administration may be in tablet, capsule, powder, liquid or semi-solid form. A tablet may comprise a solid carrier such as gelatin or an adjuvant. Liquid pharmaceutical compositions generally comprise a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included. For intravenous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilisers, buffers, antioxidants and/or other additives may be included, as required. Binding members of the present invention may be formulated in liquid, semi-solid or solid forms depending on the physicochemical properties of the molecule and the route of delivery. Formulations may include excipients, or combinations of excipients, for example: sugars, amino acids and surfactants. Liquid formulations may include a wide range of antibody concentrations and pH. Solid formulations may be produced by lyophilisation, spray drying, or drying by supercritical fluid technology, for example. Formulations of anti-GM-CSFRα will depend upon the intended route of delivery: for example, formulations for pulmonary delivery may consist of particles with physical properties that ensure penetration into the deep lung upon inhalation; topical formulations may include viscosity modifying agents, which prolong the time that the drug is resident at the site of action. In certain embodiments, the binding member may be prepared with a carrier that will protect the binding member against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are known to those skilled in the art. See, e.g., Robinson, 1978 [30].

Binding members according to the invention may be used in a method of treatment or diagnosis of the human or animal body, such as a method of treatment (which may include prophylactic treatment) of a disease or disorder in a human patient which comprises administering to said patient an effective amount of a binding member of the invention. Conditions treatable in accordance with the present invention include any in which GM-CSFRα plays a role. The published technical literature indicates a role for GM-CSF in several diseases and conditions, as summarised below. Since GM-CSF binds specifically to GM-CSFRα, pathological and/or symptomatic effects of GM-CSF can be countered by inhibiting binding of GM-CSF to GM-CSFRα. Thus, the published evidence, in addition to the pharmacological in vivo and in vitro data presented for the antibody molecules described herein in the Experimental Part, indicates that binding members of the invention can be used in treating autoimmune and/or inflammatory conditions, diseases and disorders, for example rheumatoid arthritis, asthma, allergic response, multiple sclerosis, myeloid leukaemia and atherosclerosis. Published evidence on these conditions is summarised below:

Asthma and Allergic Responses

Bronchial asthma is a common persistent inflammatory disorder of the lung characterised by airways hyper-responsiveness, mucus overproduction, fibrosis and raised IgE levels. Airways hyper-responsiveness (AHR) is the exaggerated constriction of the airways to non specific stimuli. Both AHR and mucus overproduction are thought to be responsible for the variable airway obstruction that leads to the shortness of breath characteristics of asthma attacks (exacerbations) and which is responsible for the mortality associated with this disease (around 2000 deaths/year in the United Kingdom).

Recent studies have demonstrated that GM-CSF and its receptor are upregulated at both the protein and mRNA level in asthma. Furthermore, expression levels correlate to disease severity. Increased production of GM-CSF has been measured in bronchoalveolar lavage (BAL) fluid, BAL cells, sputum, bronchiolar epithelial cells, and antigen stimulated peripheral blood mononuclear cells from asthma patients when compared to non-asthmatic subjects [31, 32]. Furthermore, the level of airway expression of GM-CSF following allergen challenge has been shown to correlate with the degree of tissue eosinophilia and the severity of the late phase asthmatic response [33]. Later studies linked upregulated GM-CSFR expression to intrinsic or non-atopic asthma, correlating levels of expression to lung function data [34]. In a mouse model of ovalbumin sensitisation and challenge, neutralisation of the activity of GM-CSF with a goat polyclonal antibody, by intranasal administration prior to ovalbumin challenge, prevented airways hyper-responsiveness and reduced both the infiltration of eosinophils and mucus secretion into the airways [35]. Similarly in a mouse model of allergic respiratory disease initiated by the intranasal administration of diesel exhaust particles, neutralisation of GM-CSF again by intranasal administration of a goat polyclonal antibody prevented airways hyperresponsiveness to methacholine, reduced BAL eosinophil counts and also diminished the expression of mucus producing goblet cells on the airways epithelium [36].

The role of GM-CSF in allergic responses has been further investigated in murine models of induced tolerance. Mice exposed to repeated daily doses of nebulised ovalbumin without prior sensitisation develop tolerance to ovalbumin and fail to elicit eosinophilic inflammation of the airways. Lung expression of GM-CSF via an adenoviral construct alters the responses of these animals and favours the influx of eosinophils into the BAL, the generation of phenotypically allergic histology and associated goblet cell hyperplasia. This generation of a typical Th2 response is further evidenced by increased serum and BAL concentrations of IL-5 and serum IL-4. Further work in this model, utilising an MHC II KO mouse indicates that GM-CSF modulates the interaction between antigen presenting cells and T cells in the airway thereby facilitating T cell-mediated responses to ovalbumin [37]. Significantly, the activity of GM-CSF as a potent activator of Th2 responses can also be demonstrated in mice lacking IL-13 and/or IL-4, indicating that neutralisation of the activity of GM-CSF presents an alternative therapeutic pathway distinct from the activity of these cytokines.

Similar observations have been made in another murine model in which repeated intranasal exposure to ragweed results in Th2-type sensitisation and mild airway inflammation on re-exposure to antigen [38]. The administration of anti-GM-CSF antibodies in conjunction with ragweed diminished Th2-associated cytokine production, presumably by inhibition of endogenous GM-CSF. In contrast, the delivery of ragweed to an airway microenvironment enriched with GM-CSF, either by multiple co-administrations of recombinant GM-CSF or a single delivery of an adenoviral vector carrying the GM-CSF transgene, resulted in considerably enhanced eosinophilic airway inflammation and ragweed-specific Th2 memory responses.

Rheumatoid Arthritis (RA)

RA is a chronic inflammatory and destructive joint disease that affects approximately 1% of the population in the industrialised world. RA is characterised by hyperplasia and inflammation of the synovial membrane, inflammation within the synovial fluid, and progressive destruction of the surrounding bone and cartilage that commonly leads to significant disability.

Whilst the cause of RA remains unknown, there is accumulating evidence for the role of GM-CSF in the progression of RA. RA is believed to be initiated and driven through a T-cell mediated, antigen-specific process. In brief, the presence of an unidentified antigen in a susceptible host is thought to initiate a T-cell response that leads to the production of T-cell cytokines with consequent recruitment of inflammatory cells, including neutrophils, macrophages and B-cells.

Many pro- and anti-inflammatory cytokines are produced in the rheumatoid joint. Moreover, disease progression, reactivation and silencing are mediated via dynamic changes in cytokine production within the joint. In particular, TNF-$\alpha$ and IL-1 are considered to exert pivotal roles in the pathogenesis of RA and many of the newer therapies developed, or in development, for the disease look to inhibit the activity of these two pro-inflammatory cytokines.

Recent studies in rodent models have suggested a central and non-redundant role for GM-CSF in the development and progression of RA. Administration of exogenous recombinant GM-CSF enhances pathology in two different mouse models of RA collagen-induced arthritis (CIA) [39] and a monoarticular arthritis model [40]. In addition to this is has been demonstrated that GM-CSF knockout (GM-CSF−/−) mice are resistant to the development of CIA and that the levels of IL-1 and tumor necrosis factor (TNF$\alpha$) found in synovial joint fluid was reduced compared to wildtype mice [41, 42]. Similarly, induction of monoarthritis using intra-articular injection of methylated bovine serum albumin and IL-1 in GM-CSF$^{-/-}$ mice results in reduced disease severity compared to wild-type mice [43].

Furthermore, administration of murine anti-GM-CSF mAb significantly ameliorates disease severity in CIA and monoarticular arthritis models. In the CIA model, mAb treatment was effective in treating progression of established disease, histopathology and significantly lowering joint IL-1 and TNF-$\alpha$ levels. In addition, mAb treatment prior to arthritis onset lessened CIA disease severity [44,43].

A number of studies have analysed the levels of cytokines and receptors present in arthritic synovial fluid and membrane biopsy samples from human tissue. Circulating mononuclear cells in 27 RA patients, 13 healthy volunteers and 14 patients with osteoporosis were assessed for GM-CSFR levels by using PE-labelled GM-CSF [45]. In this study it was demonstrated that twice as many receptor positive cells were detected in RA patients (53%), compared to healthy controls (20%) and patients undergoing investigation for osteoporosis (25%), thus suggesting that monocytes may be primed to respond to locally produced GM-CSF. Cytokine gene expression from RA patients [46] using in situ hybridization of SF cells demonstrated elevated levels of GM-CSF, IL-1, TNF-a and IL-6. Furthermore, isolated and cultured fibroblast-derived synoviocytes from normal volunteers demonstrated elevated protein levels of GM-CSF in response to IL-1$\alpha$, IL-1$\beta$, TNF-$\alpha$ and TNF-$\beta$ [47]. Quantification of serum levels of GM-CSF in RA patients [48] showed that levels of protein were increased in severe (366 pg/ml, n=26) and moderate (376 pg/ml, n=58) RA patients compared to the control group (174 pg/ml, n=43), furthermore it was also shown that GM-CSF was significantly elevated in the SF of patients with RA (1300 pg/ml).

Previously it has been observed that administration of recombinant GM-CSF in patients being treated for neutropenia could cause an exacerbation of RA [49]. Similar observations were made for a patient with Felty's syndrome following treatment with recombinant GM-CSF [50].

Chronic Obstructive Pulmonary Disease (COPD)

Chronic Obstructive Pulmonary Disease (COPD) is defined as a disease state characterised by airflow limitation that is not fully reversible. The chronic airflow limitation is usually both progressive and associated with an abnormal inflammatory response of the lungs to noxious particles or gases. This airflow limitation is caused by a mixture of small airway disease (obstructive bronchiolitis) and parenchymal destruction (emphysema), the relative contributions of which vary from person to person. The resulting characteristic symptoms of COPD are cough, sputum production, and dyspnoea upon exertion.

COPD is a major public health problem and is the fourth leading cause of chronic morbidity and mortality in the US. The disease is currently treated with drugs originally developed for asthma such as oral or inhaled corticosteroids with or without bronchodilators including β agonists. However, none of these drugs has been shown to slow the progression of COPD [51]. For example, corticosteroids which markedly suppress the eosinophilic inflammation in asthma do not appear to have any effect on the inflammation seen in COPD which is predominantly neutrophil mediated [52]. Therefore, there is a need to develop new treatments for COPD which specifically target the inflammatory processes underlying the pathophysiology of this disease.

GM-CSF, through its role in neutrophil and macrophage function, may play an important role in the pathogenesis of COPD.

In a study using quantitative PCR it was shown that in age matched COPD sputum versus non-obstructed smoker sputum GMCSF copy number was significantly elevated [53]. Furthermore, in a rodent model of cigarette smoke induced lung inflammation, animals treated intranasally with an antibody to GM-CSF 2 days, 4 hrs and 1 hr prior to smoke exposure demonstrated a significant reduction in neutrophils, macrophages and MMP-9 levels from the BAL when compared with the isotype control antibody 5 days after challenge [54]. These studies are also supported by our own observations investigating GM-CSF levels in induced sputum from patients with a range of COPD severities. In these studies we showed that GM-CSF was elevated in the sputum of approximately 40% of COPD patients tested irrespective of disease severity, with GMCSF levels approaching 500 pg/ml in some cases. GMCSF did not appear to be elevated in non-smoking and smoking matched control patients. These data suggest that GM-CSF may be one of the key mediators in smoke induced airway inflammation and COPD.

Multiple Sclerosis (MS)

GM-CSF has been implicated in the autoimmune disease multiple sclerosis. By administering myelin oligodendrocyte glycoprotein (MOG) antigen to rodents a model of human multiple sclerosis can be induced that demonstrates many of the phenotypes of MS such as central nervous system inflammation and demyelination that can result in an MS like paralysis. In GM-CSF null mice MOG was unable to induce the EAE phenotype [55]. Furthermore, it was shown that these mice had decreased T cell proliferation to MOG antigen and a decreased production of the Th1 cytokines IL-6 and IFN-γ. Administration of GM-CSF neutralising antibodies at the same time as antigen challenge prevented disease onset for 10 days after treatment with evidence of reduced lesions. If administered after disease onset mice recovered completely within 20 days of treatment [55].

Leukaemia

GM-CSF has also been implicated in the myeloid leukaemia, juvenile chronic myeloid leukaemia (JCML). This condition is a myeloproliferative disorder that primarily affects patients less than 4 years of age. In vitro JCML peripheral blood granulocyte-macrophage progenitors (CFU-GM) demonstrate spontaneous proliferation at low cell densities, an observation not previously described for other myeloproliferative disorders. Furthermore, depletion of monocytes from these cultures abolished this proliferation. Subsequently it has been demonstrated that this spontaneous proliferation is mediated via a hypersensitivity of the JCML progenitors to the monocyte derived cytokine GM-CSF [56,57,58,59,60,61]. Rather than an overproduction or elevated levels of GM-CSF in JCML patients, the hypersensitivity of the JCML progenitors appears to be through a deregulated GM-CSF induced Ras signal transduction pathway [62]. Recent studies with a GM-CSF analogue (E21R), that antagonises the action of GM-CSF in both binding studies and functional assays, has shown that by inhibiting the action of GM-CSF one can significantly reduce the JCML cell load in a severe combined immunodeficient/non obese diabetic (SCID/NOD) mouse xenograft model of JCML [63]. Prophylactic systemic dosing of E21R at the time of engraftment prevented JCML progenitors establishing in the bone marrow and dosing E21R 4 weeks post engraftment induced remission of JCML, with a reduction in cell load. Furthermore, administration of E21R to SCID/NOD mice co-engrafted with normal human bone marrow and JCML bone marrow caused a reduction in JCML load however normal bone marrow cells remained unaffected.

Atherosclerosis

Ischemic heart disease is the commonest cause of death worldwide. Over recent years the concept that inflammation plays a significant role in the pathogenesis of atherosclerosis has increased, with inflammatory cell accumulation occurring hand in hand with lipid accumulation in the artery walls.

Once resident in the arterial wall inflammatory cells, such as monocytes and macrophages, participate and perpetuate the local inflammatory response. These macrophages also express scavenger receptors for a range of lipoproteins and thus contribute to the cells differentiation into 'foamy cells'. It is the death of these 'foamy cells' that contribute to the development of the lipid core, a classic feature of these lesions. As the inflammation continues within these atherosclerotic plaques these activated inflammatory cells release fibrogenic mediators and growth factors that promote smooth muscle cell (SMC) proliferation and fibrosis of the plaque. In addition to promoting fibrosis these cells also release proteolytic enzymes, such as matrix metalloproteinase's (MMPs), that contribute to a weakening of the fibrotic plaque, thus rendering them prone to disruption. These plaques once ruptured release cell debri and coagulation factors, such as tissue factor, into the vessel stimulating the coagulation cascade and development of thrombi. The resulting arterial thrombosis can then lead to myocardial ischemia or infarction.

Recently GM-CSF has been implicated in many aspects of disease progression in atherosclerosis. In atherosclerotic lesions of cholesterol fed rabbits GM-CSF was found to be co-localised with macrophages and to a lesser degree endothelial cells and SMC [64]. Furthermore, it has also been shown that GM-CSF expression is augmented in human atherosclerotic vessels at the sites of macrophage accumulation and within medial SMCs and endothelial cells [65]. This increase in GM-CSF levels is, in part, attributed to the direct cell-cell contact of monocyte/macrophages and endothelial cells during the formation and pathogenesis of the atherosclerotic lesion [66]. Another key element in the atherotic lesion is the 'foamy cell', that is macrophages that have taken up oxidised low density lipoproteins (LDL) via scavenger receptors on the surface. In vitro this uptake of Ox-LDL can further stimulate macrophages to proliferate via a GM-CSF dependent mechanism [67].

As atherosclerosis is a chronic inflammatory process anti-inflammatory agents such as glucocorticoids have been investigated. Dexamethasone, an anti-inflammatory glucocorticoid, suppresses the development of atherosclerosis in various experimental animal models [68,69,70,71]. The efficacy of which has been attributed to inhibition of SMC migration [72] and proliferation [73], and reduction in the chemotaxis of circulating monocytes and leukocytes [74]. Recent studies shown that ox-LDL can induce GM-CSF release from mouse peritoneal macrophages [75]. Furthermore, following treatment with dexamethasone this GM-CSF release was dose dependently inhibited, suggesting that the anti-inflammatory affects of dexamethasone are mediated by inhibition of the ox-LDL induced GM-CSF production. As GM-CSF appears to have a central role in atherosclerosis, an alternative to glucocorticoids could be to inhibit the GM-CSF activity in this indication.

Terminology

"And/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

GM-CSFRα and GM-CSF

GM-CSFRα is the alpha chain of the receptor for granulocyte macrophage colony stimulating factor. The full length sequence of human GM-CSFRα is deposited under Accession number S06945 (gi:106355) [76] and is set out herein as SEQ ID NO: 202. The mature form of human GM-CSFRα, i.e. with the signal peptide cleaved, is set out herein as SEQ ID NO: 206. Unless otherwise indicated by context, references herein to GM-CSFRα refer to human or non-human primate (e.g. cynomolgus) GM-CSFRα, normally human. GM-CSFRα may be naturally occurring GM-CSFRα or recombinant GM-CSFRα.

The 298 amino acid extracellular domain of human GM-CSF receptor a has amino acid sequence SEQ ID NO: 205.

Unless otherwise indicated by context, references herein to GM-CSF refer to human or non-human primate (e.g. cynomolgus) GM-CSF, normally human.

GM-CSF normally binds to the extracellular domain (SEQ ID NO: 205) of the mature GM-CSF receptor alpha chain (SEQ ID NO: 206). As described elsewhere herein, this binding is inhibited by binding members of the invention.

Naturally occurring splice variants of GM-CSFRα have been identified—see for example refs. [77 and 78]. The extracellular domain is highly conserved in these splice variants. Binding members of the invention may or may not bind to one or more splice variants of GM-CSFRα, and may or may not inhibit GM-CSF binding to one or more splice variants of GM-CSFRα.

Binding Member

This describes a member of a pair of molecules that bind one another. The members of a binding pair may be naturally derived or wholly or partially synthetically produced. One member of the pair of molecules has on its surface, or a cavity, which binds to and is therefore complementary to a particular spatial and polar organisation of the other member of the pair of molecules. Examples of types of binding pairs are antigen-antibody, biotin-avidin, hormone-hormone receptor, receptor-ligand, enzyme-substrate. The present invention is concerned with antigen-antibody type reactions.

A binding member normally comprises a molecule having an antigen-binding site. For example, a binding member may be an antibody molecule or a non-antibody protein that comprises an antigen-binding site. An antigen binding site may be provided by means of arrangement of CDRs on non-antibody protein scaffolds such as fibronectin or cytochrome B etc. [80,81,82], or by randomising or mutating amino acid residues of a loop within a protein scaffold to confer binding to a desired target. Scaffolds for engineering novel binding sites in proteins have been reviewed in detail [82]. Protein scaffolds for antibody mimics are disclosed in WO/0034784 in which the inventors describe proteins (antibody mimics) that include a fibronectin type III domain having at least one randomised loop. A suitable scaffold into which to graft one or more CDRs, e.g. a set of HCDRs, may be provided by any domain member of the immunoglobulin gene superfamily. The scaffold may be a human or non-human protein.

An advantage of a non-antibody protein scaffold is that it may provide an antigen-binding site in a scaffold molecule that is smaller and/or easier to manufacture than at least some antibody molecules. Small size of a binding member may confer useful physiological properties such as an ability to enter cells, penetrate deep into tissues or reach targets within other structures, or to bind within protein cavities of the target antigen.

Use of antigen binding sites in non-antibody protein scaffolds is reviewed in ref. [79]. Typical are proteins having a stable backbone and one or more variable loops, in which the amino acid sequence of the loop or loops is specifically or randomly mutated to create an antigen-binding site having for binding the target antigen. Such proteins include the IgG-binding domains of protein A from S. aureus, transferrin, tetranectin, fibronectin (e.g. 10th fibronectin type III domain) and lipocalins. Other approaches include synthetic "Microbodies" (Selecore GmbH), which are based on cyclotides—small proteins having intra-molecular disulphide bonds.

In addition to antibody sequences and/or an antigen-binding site, a binding member according to the present invention may comprise other amino acids, e.g. forming a peptide or polypeptide, such as a folded domain, or to impart to the molecule another functional characteristic in addition to ability to bind antigen. Binding members of the invention may carry a detectable label, or may be conjugated to a toxin or a targeting moiety or enzyme (e.g. via a peptidyl bond or linker). For example, a binding member may comprise a catalytic site (e.g. in an enzyme domain) as well as an antigen binding site, wherein the antigen binding site binds to the antigen and thus targets the catalytic site to the antigen. The catalytic site may inhibit biological function of the antigen, e.g. by cleavage.

Although, as noted, CDRs can be carried by scaffolds such as fibronectin or cytochrome B [80, 81, 82], the structure for carrying a CDR or a set of CDRs of the invention will generally be of an antibody heavy or light chain sequence or substantial portion thereof in which the CDR or set of CDRs is located at a location corresponding to the CDR or set of CDRs of naturally occurring VH and VL antibody variable domains encoded by rearranged immunoglobulin genes. The structures and locations of immunoglobulin variable domains may be determined by reference to (Kabat, et al., 1987 [98], and updates thereof, now available on the Internet (http://immuno.bme.nwu.edu or find "Kabat" using any search engine).

Binding members of the present invention may comprise antibody constant regions or parts thereof, preferably human antibody constant regions or parts thereof. For example, a VL domain may be attached at its C-terminal end to antibody light chain constant domains including human Cκ or Cλ chains, preferably Cλ chains. Similarly, a binding member based on a VH domain may be attached at its C-terminal end to all or part (e.g. a CH1 domain) of an immunoglobulin heavy chain derived from any antibody isotype, e.g. IgG, IgA, IgE and IgM and any of the isotype sub-classes, particularly IgG1, IgG2 and IgG4. IgG1, IgG2 or IgG4 is preferred. IgG4 is preferred because it does not bind complement and does not create effector functions. Any synthetic or other constant region variant that has these properties and stabilizes variable regions is also preferred for use in embodiments of the present invention.

Binding members of the invention may be labelled with a detectable or functional label. Detectable labels include radiolabels such as $^{131}I$ or $^{99}Tc$, which may be attached to antibodies of the invention using conventional chemistry known in the art of antibody imaging. Labels also include enzyme labels such as horseradish peroxidase. Labels further include chemical moieties such as biotin that may be detected via binding to a specific cognate detectable moiety, e.g. labelled avidin. Thus, a binding member or antibody molecule of the present invention can be in the form of a conjugate comprising the binding member and a label, optionally joined via a linker such as a peptide. The binding member can be conjugated for example to enzymes (e.g. peroxidase, alkaline phosphatase) or a fluorescent label including, but not limited to, biotin, fluorochrome, green fluorescent protein. Further, the label may comprise a toxin moiety such as a toxin moiety selected from a group of *Pseudomonas* exotoxin (PE or a cytotoxic fragment or mutant thereof), Diptheria toxin (a cytotoxic fragment or mutant thereof), a botulinum toxin A through F, ricin or a cytotoxic fragment thereof, abrin or a cytotoxic fragment thereof, saporin or a cytotoxic fragment thereof, pokeweed antiviral toxin or a cytotoxic fragment thereof and bryodin 1 or a cytotoxic fragment thereof. Where the binding member comprises an antibody molecule, the labelled binding member may be referred to as an immunoconjugate.

Antibody Molecule

This describes an immunoglobulin whether natural or partly or wholly synthetically produced. The term also covers any polypeptide or protein comprising an antibody antigen-binding site. Antibody fragments that comprise an antibody antigen-binding site are molecules such as Fab, F(ab')$_2$, Fab', Fab'-SH, scFv, Fv, dAb, Fd; and diabodies.

It is possible to take monoclonal and other antibodies and use techniques of recombinant DNA technology to produce other antibodies or chimeric molecules that retain the specificity of the original antibody. Such techniques may involve introducing DNA encoding the immunoglobulin variable region, or the CDRs, of an antibody to the constant regions, or constant regions plus framework regions, of a different immunoglobulin. See, for instance, EP-A-184187, GB 2188638A or EP-A-239400, and a large body of subsequent literature. A hybridoma or other cell producing an antibody may be subject to genetic mutation or other changes, which may or may not alter the target binding of antibodies produced.

As antibodies can be modified in a number of ways, the term "antibody molecule" should be construed as covering any binding member or substance having an antibody antigen-binding site. Thus, this term covers antibody fragments and derivatives, including any polypeptide comprising an antibody antigen-binding site, whether natural or wholly or partially synthetic. Chimeric molecules comprising an antibody antigen-binding site, or equivalent, fused to another polypeptide are therefore included. Cloning and expression of chimeric antibodies are described in EP-A-0120694 and EP-A-0125023, and a large body of subsequent literature.

Further techniques available in the art of antibody engineering have made it possible to isolate human and humanised antibodies. Human and humanised antibodies are preferred embodiments of the invention, and may be produced using any suitable method. For example, human hybridomas can be made [83]. Phage display, another established technique for generating binding members has been described in detail in many publications such as ref. [83] and WO92/01047 (discussed further below). Transgenic mice in which the mouse antibody genes are inactivated and functionally replaced with human antibody genes while leaving intact other components of the mouse immune system, can be used for isolating human antibodies [84]. Humanised antibodies can be produced using techniques known in the art such as those disclosed in for example WO91/09967, U.S. Pat. No. 5,585,089, EP592106, U.S. Pat. No. 5,565,332 and WO93/17105. Further, WO2004/006955 describes methods for humanising antibodies, based on selecting variable region framework sequences from human antibody genes by comparing canonical CDR structure types for CDR sequences of the variable region of a non-human antibody to canonical CDR structure types for corresponding CDRs from a library of human antibody sequences, e.g. germline antibody gene segments. Human antibody variable regions having similar canonical CDR structure types to the non-human CDRs form a subset of member human antibody sequences from which to select human framework sequences. The subset members may be further ranked by amino acid similarity between the human and the non-human CDR sequences. In the method of WO2004/006955, top ranking human sequences are selected to provide the framework sequences for constructing a chimeric antibody that functionally replaces human CDR sequences with the non-human CDR counterparts using the selected subset member human frameworks, thereby providing a humanized antibody of high affinity and low immunogenicity without need for comparing framework sequences between the non-human and human antibodies. Chimeric antibodies made according to the method are also disclosed.

Synthetic antibody molecules may be created by expression from genes generated by means of oligonucleotides synthesized and assembled within suitable expression vectors [85, 86].

It has been shown that fragments of a whole antibody can perform the function of binding antigens. Examples of binding fragments are (i) the Fab fragment consisting of VL, VH, CL and CH1 domains; (ii) the Fd fragment consisting of the VH and CH1 domains; (iii) the Fv fragment consisting of the VL and VH domains of a single antibody; (iv) the dAb fragment [87, 88, 89] which consists of a VH or a VL domain; (v) isolated CDR regions; (vi) F(ab')2 fragments, a bivalent fragment comprising two linked Fab fragments (vii) single chain Fv molecules (scFv), wherein a VH domain and a VL domain are linked by a peptide linker which allows the two domains to associate to form an antigen binding site [90, 91]; (viii) bispecific single chain Fv dimers (PCT/US92/09965) and (ix) "diabodies", multivalent or multispecific fragments constructed by gene fusion (WO94/13804; [92]). Fv, scFv or diabody molecules may be stabilised by the incorporation of disulphide bridges linking the VH and VL domains [93]. Minibodies comprising a scFv joined to a CH3 domain may also be made [94].

A dAb (domain antibody) is a small monomeric antigen-binding fragment of an antibody, namely the variable region of an antibody heavy or light chain [89]. VH dAbs occur naturally in camelids (e.g. camel, llama) and may be produced by immunising a camelid with a target antigen, isolating antigen-specific B cells and directly cloning dAb genes from individual B cells. dAbs are also producible in cell culture. Their small size, good solubility and temperature stability makes them particularly physiologically useful and suitable for selection and affinity maturation. A binding member of the present invention may be a dAb comprising a VH or VL domain substantially as set out herein, or a VH or VL domain comprising a set of CDRs substantially as set out herein. By "substantially as set out" it is meant that the relevant CDR or VH or VL domain of the invention will be either identical or highly similar to the specified regions of which the sequence is set out herein. By "highly similar" it is contemplated that from 1 to 5, preferably from 1 to 4 such as 1 to 3 or 1 or 2, or 3 or 4, amino acid substitutions may be made in the CDR and/or VH or VL domain.

Where bispecific antibodies are to be used, these may be conventional bispecific antibodies, which can be manufactured in a variety of ways [95], e.g. prepared chemically or from hybrid hybridomas, or may be any of the bispecific antibody fragments mentioned above. Examples of bispecific antibodies include those of the BiTE™ technology in which the binding domains of two antibodies with different specificity can be used and directly linked via short flexible peptides. This combines two antibodies on a short single polypeptide chain. Diabodies and scFv can be constructed without an Fc region, using only variable domains, potentially reducing the effects of anti-idiotypic reaction.

Bispecific diabodies, as opposed to bispecific whole antibodies, may also be particularly useful because they can be readily constructed and expressed in *E. coli*. Diabodies (and many other polypeptides such as antibody fragments) of appropriate binding specificities can be readily selected using phage display (WO94/13804) from libraries. If one arm of the diabody is to be kept constant, for instance, directed against GM-CSFRα, then a library can be made where the other arm is varied and an antibody of appropriate target binding selected. Bispecific whole antibodies may be made by knobs-into-holes engineering [96].

Antigen-Binding Site

This describes the part of a molecule that binds to and is complementary to all or part of the target antigen. In an antibody molecule it is referred to as the antibody antigen-binding site, and comprises the part of the antibody that binds to and is complementary to all or part of the target antigen. Where an antigen is large, an antibody may only bind to a particular part of the antigen, which part is termed an epitope. An antibody antigen-binding site may be provided by one or more antibody variable domains. Preferably, an antibody antigen-binding site comprises an antibody light chain variable region (VL) and an antibody heavy chain variable region (VH).

Kabat Numbering

Residues of antibody sequences herein are generally referred to using Kabat numbering as defined in Kabat et al., 1971 [97]. See also refs. [98, 99].

Isolated

This refers to the state in which binding members of the invention, or nucleic acid encoding such binding members, will generally be in accordance with the present invention. Isolated members and isolated nucleic acid will be free or substantially free of material with which they are naturally associated such as other polypeptides or nucleic acids with which they are found in their natural environment, or the environment in which they are prepared (e.g. cell culture) when such preparation is by recombinant DNA technology practised in vitro or in vivo. Members and nucleic acid may be formulated with diluents or adjuvants and still for practical purposes be isolated—for example the members will normally be mixed with gelatin or other carriers if used to coat microtitre plates for use in immunoassays, or will be mixed with pharmaceutically acceptable carriers or diluents when used in diagnosis or therapy. Binding members may be glycosylated, either naturally or by systems of heterologous eukaryotic cells (e.g. CHO or NS0 (ECACC 85110503)) cells, or they may be (for example if produced by expression in a prokaryotic cell) unglycosylated.

EXPERIMENTAL PART

Background

Figure 1A:
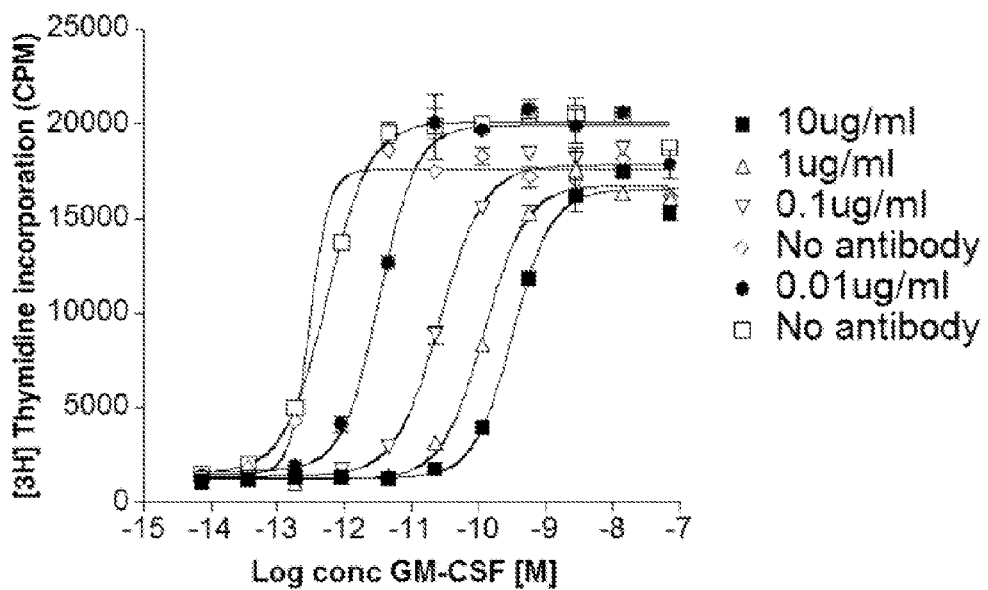
FIGS. 1A-1D. $pA_2$ analysis of two anti-GM-CSFRα antibodies in the TF-1 proliferation assay. Proliferation of TF-1 cells was induced with increasing concentrations of GM-CSF in the presence of increasing concentrations of two optimised IgG4, Antibody 6 (FIG. 1A) and Antibody 1 (FIG. 1B), respectively. For data shown in FIG. 1A and FIG. 1B the incorporation of tritiated thymidine was measured and the EC50 of GM-CSF at each concentration of antibody was calculated. For data shown in FIG. 1C and FIG. 1D dose ratios were then calculated and analysed by Schild regression in order to obtain $pA_2$ values.
Figure 1B:
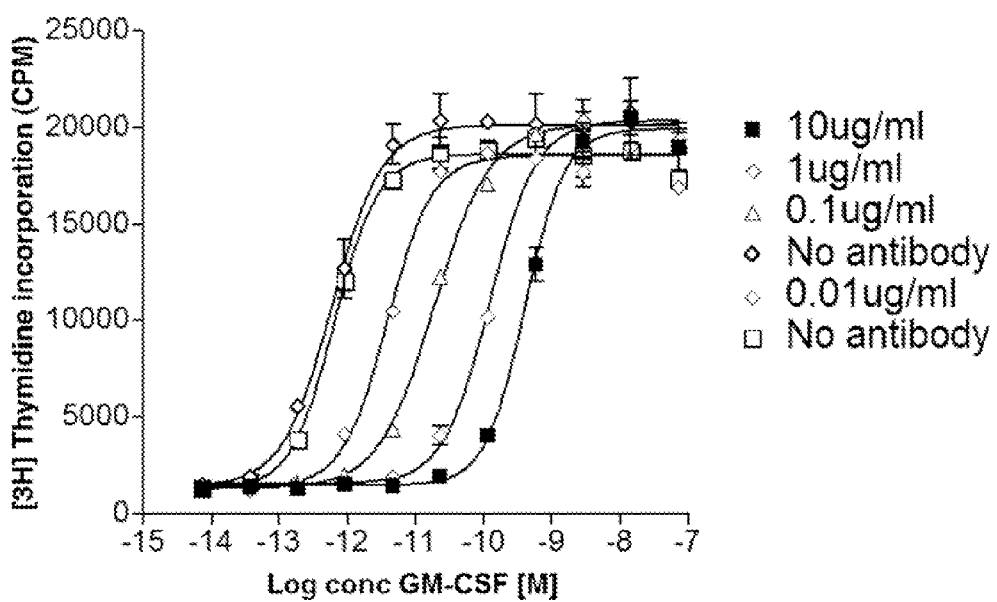
Figure 1C:
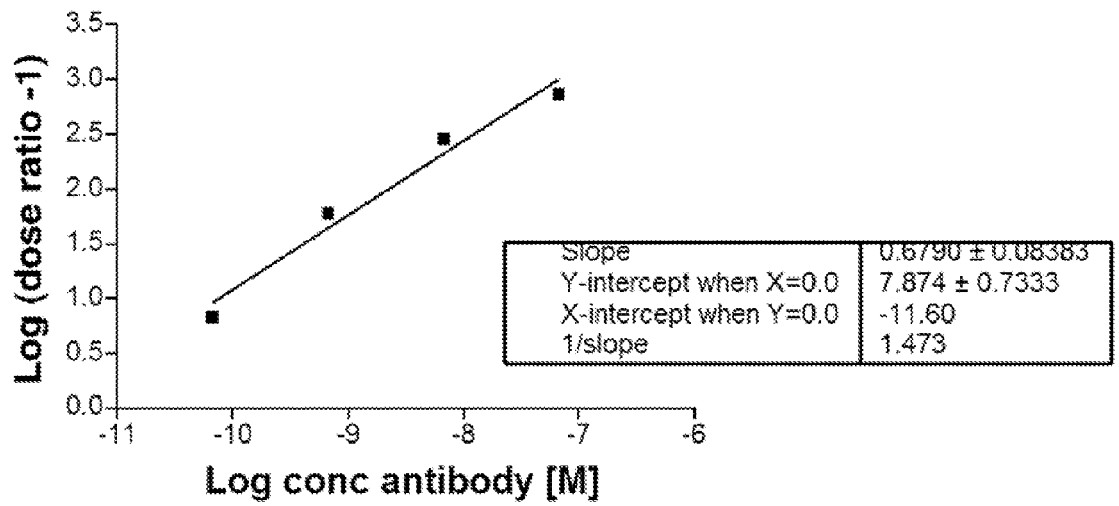
Figure 1D:
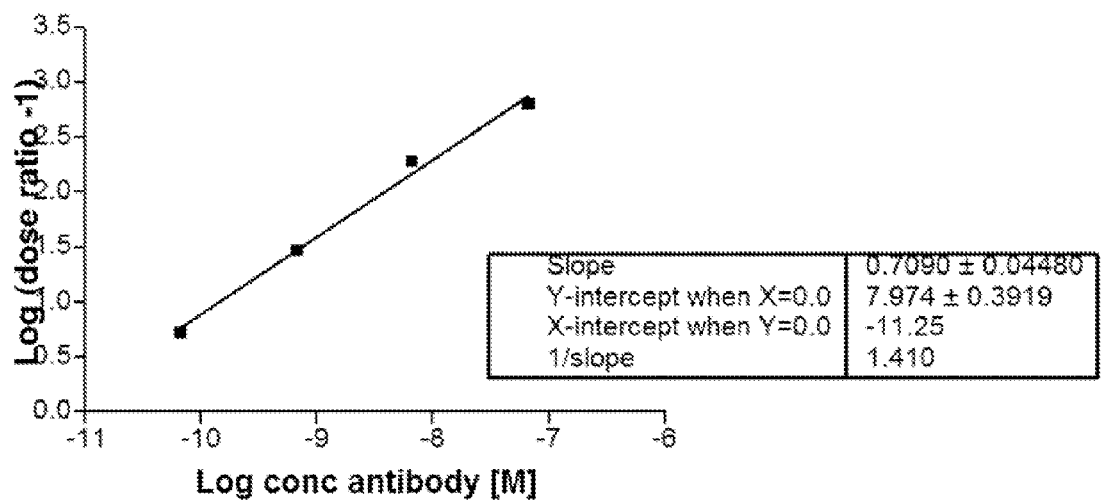
Figure 2A:
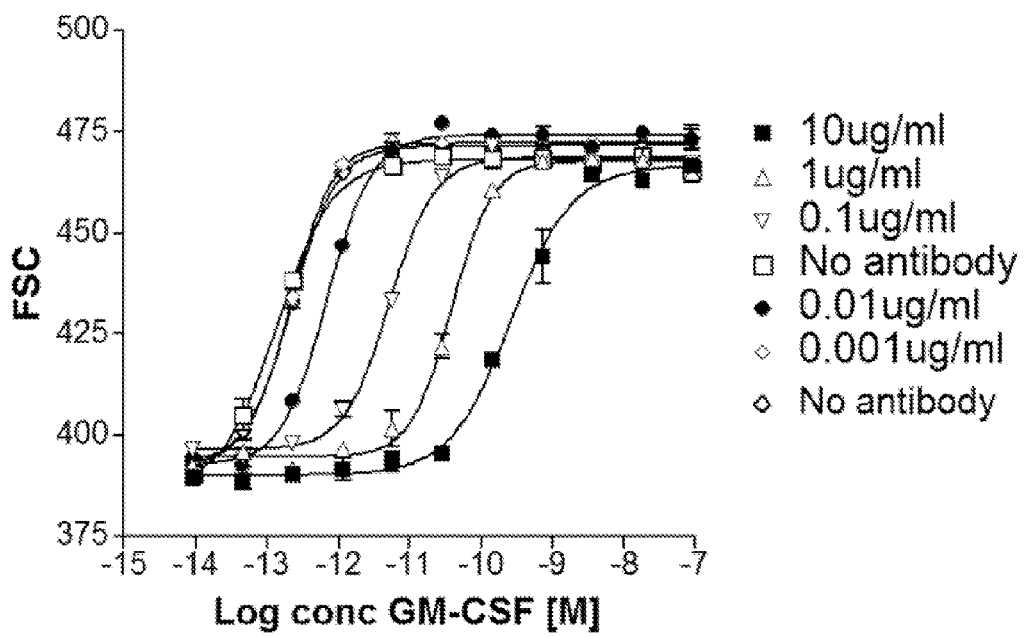
FIGS. 2A-2D. $pA_2$ analysis of an anti-GM-CSFRα antibody, Antibody 6, in the granulocyte shape change assays. Human (FIGS. 2A and 2C) or cynomolgus (FIGS. 2B and 2D) granulocytes were treated with increasing concentrations of GM-CSF in the presence of increasing concentrations of IgG4. The change in shape of the granulocytes was measured using flow cytometry and the EC50 of GM-CSF at each concentration of antibody was calculated (FIG. 2A and FIG. 2B). Dose ratios were then calculated and analysed by Schild regression in order to obtain $pA_2$ values (FIG. 2C and FIG. 2D).
Figure 2B:
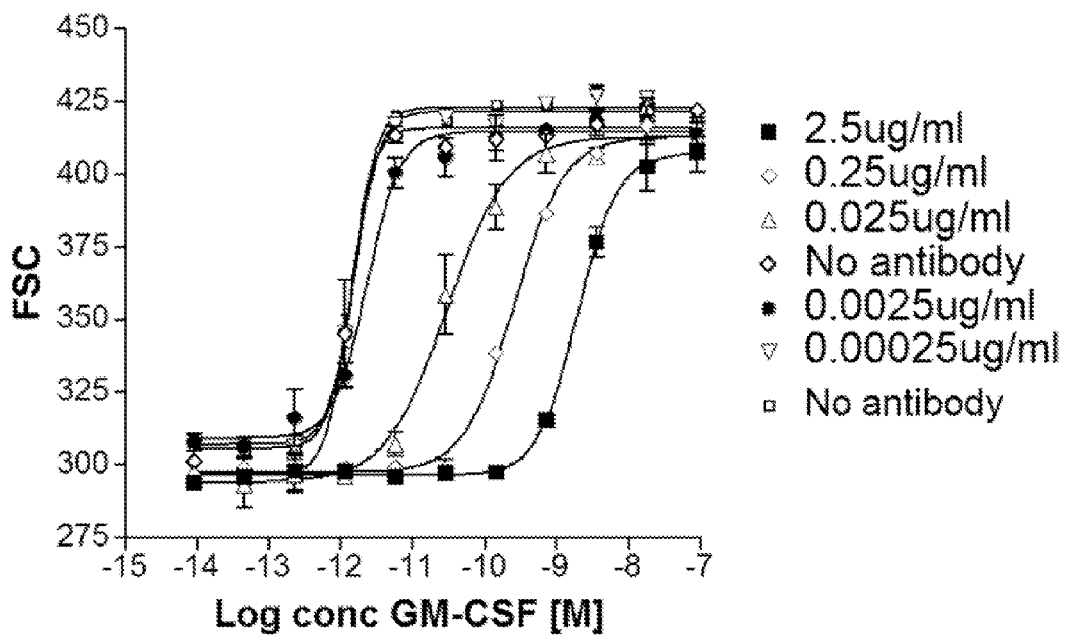
Figure 2C:
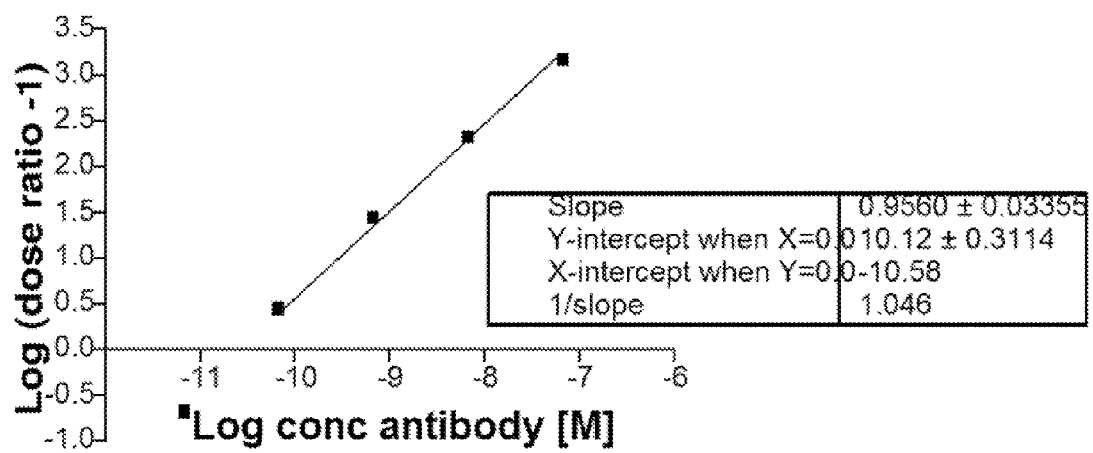
Figure 2D:
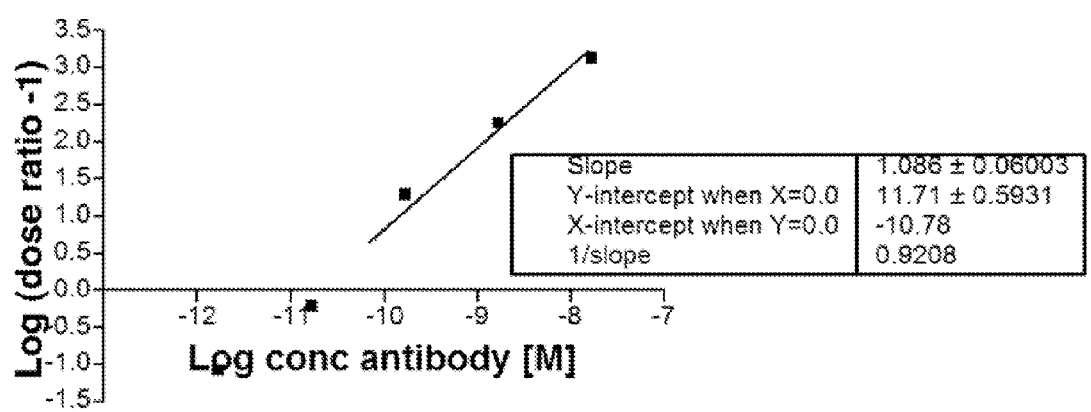
Figure 3:
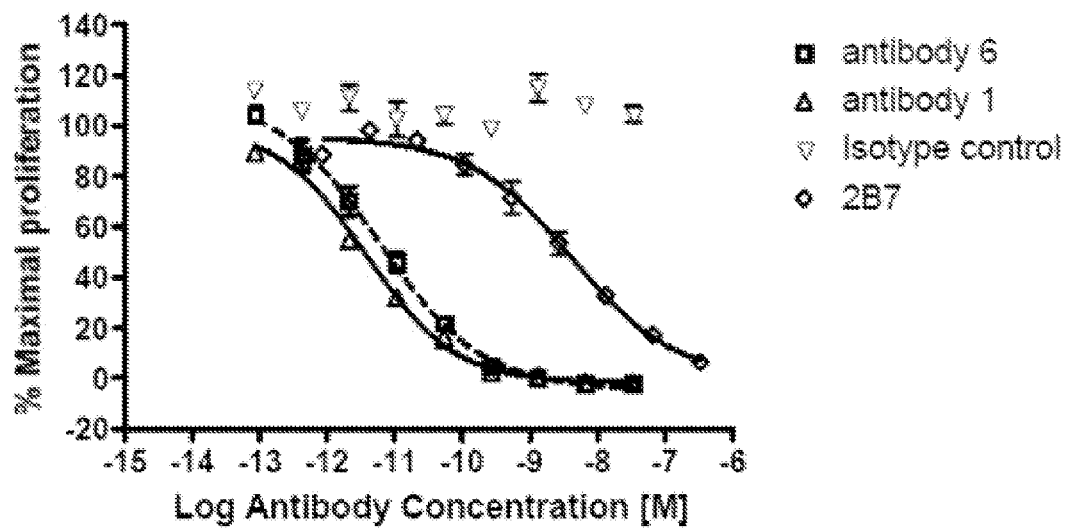
FIG. 3. Antagonist potency of two antibodies, Antibodies 1 and 6, respectively, as IgG4s in an assay measuring proliferation of TF-1 cells induced by 7 pM human GM-CSF. Also shown are data for positive control IgG4 2B7 and for an isotype control IgG4. Data represent the mean with standard deviation bars of triplicate determinations within the same experiment.
Figure 4:
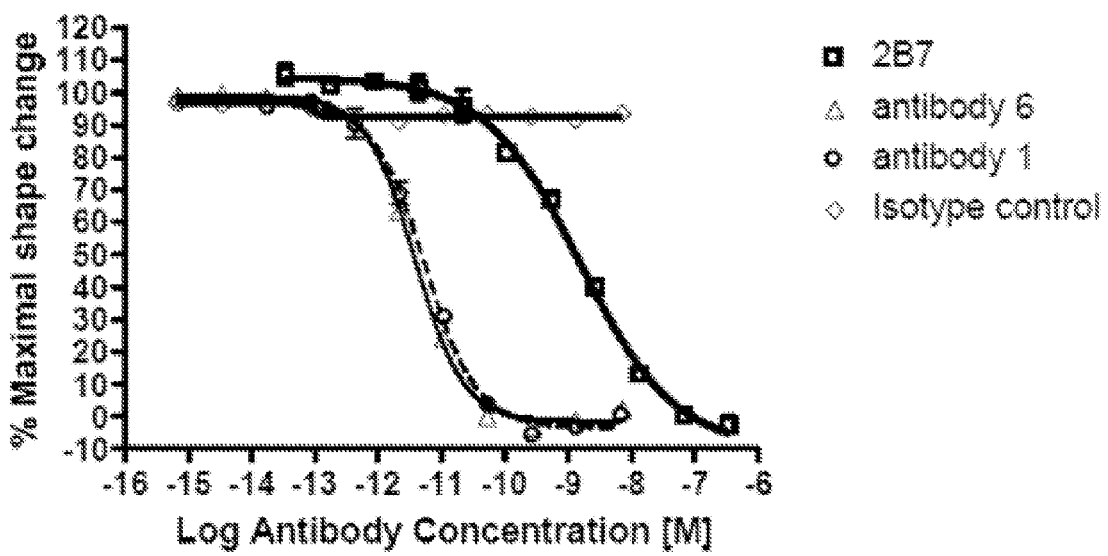
FIG. 4. Antagonist potency of two antibodies, Antibodies 1 and 6, respectively, as IgG4s in an assay measuring the shape change of human granulocytes induced by 7 pM human GM-CSF. Also shown are data for control IgG4 2B7 and for an isotype control IgG4. Data represent the mean with standard deviation bars of triplicate determinations within the same experiment.
Figure 5:
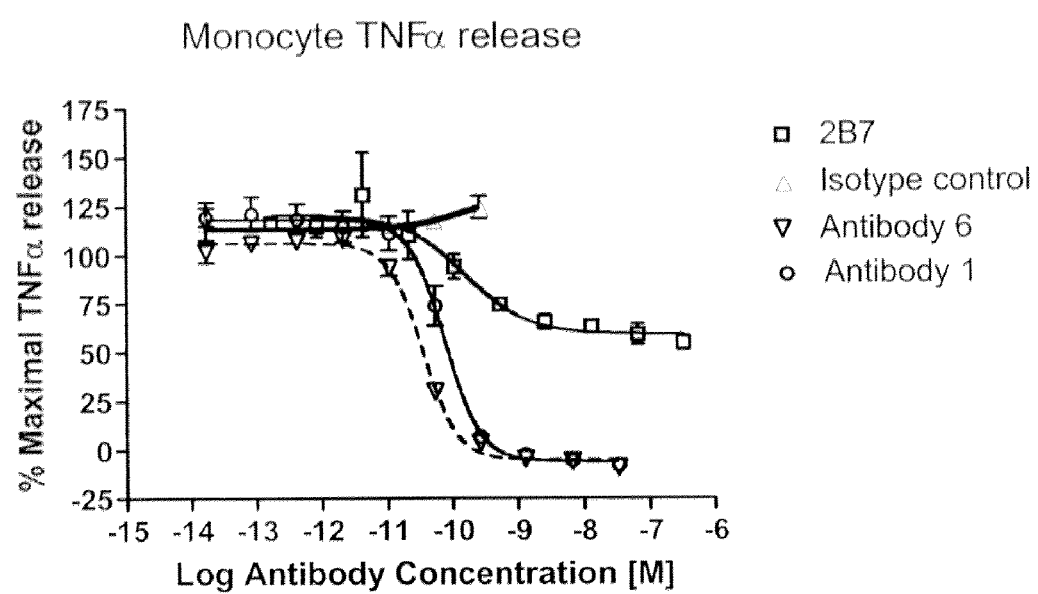
FIG. 5. Antagonist potency of two antibodies, Antibodies 1 and 6, respectively, as IgG4s in an assay measuring TNFα release from human monocytes stimulated with 1 nM human GM-CSF. Also shown are data for control antibody 2B7 and for an isotype control IgG4. Data represent the mean with standard deviation bars of triplicate determinations within the same experiment.
Figure 6:
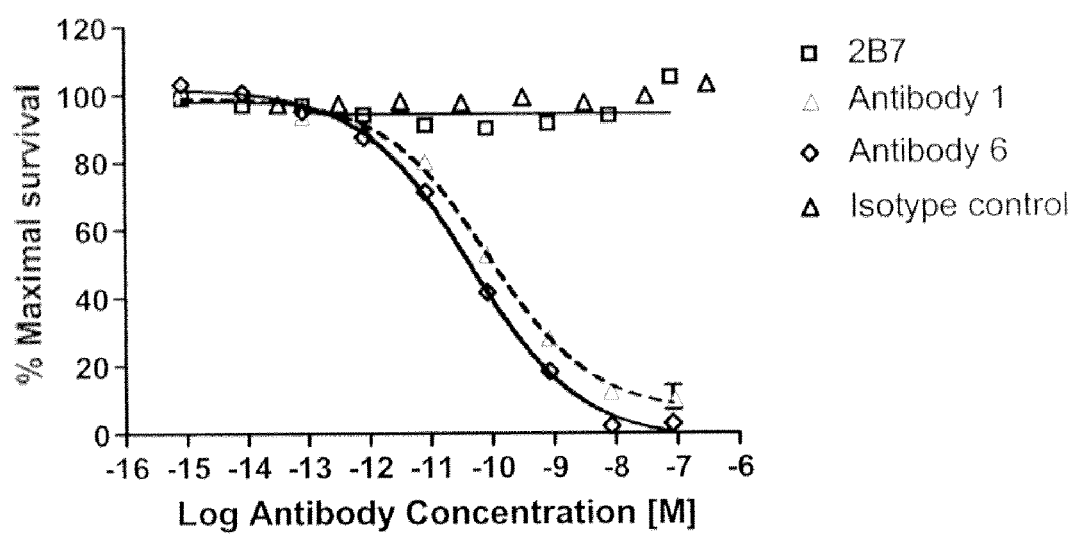
FIG. 6. Antagonist potency of two antibodies, Antibodies 1 and 6, respectively, as IgG4s in an assay measuring human granulocyte survival induced by 7 pM human GM-CSF. Also shown are data for the control antibody 2B7 and for an isotype control IgG4. Data represent the mean with standard deviation bars of triplicate determinations within the same experiment.

Human antibody fragments may be selected in vitro from repertoires displayed on the surface of filamentous bacteriophage. This process is known as phage display and provides a means of deriving human antibody fragments. The process can be used to isolate human anti-human specificities and may be tailored to derive antibodies of particular affinity characteristics.

Antibody fragments consisting only of the heavy chain variable (VH) and light chain variable (VL) domains joined together by a short peptide linker contain all the information that is necessary to determine antigen binding. Such fragments are known as single chain Fv (scFv). When displayed on the phage surface, scFv have been shown to both fold correctly and bind to antigen. Large repertoires of human scFv have been constructed in this way, and have provided a source from which individual clones may be isolated for development as drug candidates. Candidate scFv are then reformatted as whole IgG (typically human IgG) molecules for therapeutic applications.

SUMMARY

Selections were carried out on an scFv phage display library derived from human spleen lymphocytes in order to enrich for populations of phage that bound to human GM-CSFRα. We isolated scFv antibodies having selected characteristics and converted these scFv into $IgG_4$. Using a variety of assays, a panel of antibodies were isolated, optimised and germlined to produce IgG4 with appropriate specification for a therapeutic antibody.

19 antibody clones, whose sequences are shown as antibodies 1, 2 and 4-20 in the sequence listing, were derived from a parent antibody. The parent is shown as antibody 3 in the sequence listing, and is also referred to herein as 28G5. The 19 clones were selected as showing particularly good properties in a range of biological assays, as described in the Experimental Part, and were designated antibody numbers 1, 2 and 4 to 20.

The bioassays were designed to reflect the inflammatory nature of diseases such as rheumatoid arthritis. For example, the shape change of neutrophils necessary for their recruitment to the site of action, the release of proinflammatory factors by monocytes and the increased survival of inflammatory cell types in response to particular signals. The antibodies exhibit potent neutralisation activity in these assays.

Detailed protocols of the assay methods used are provided below in the section entitled "Assay Materials and Methods".

Antibody Lead Isolation

A large single chain FV (scFv) human antibody library was used for selections. This was derived from the spleen lymphocytes from 20 healthy donors and cloned into a phagemid vector. ScFv which recognised GM-CSFRα were isolated from the phage display library in a series of repeated selection cycles on purified GMCSF-Rα derived from overexpression of a purification-tagged, soluble, extracellular domain of the receptor in HEK293T cells. This was achieved essentially as described in Vaughan et al [102]. In brief, following exposure of the biotinylated receptor to the phage library, the protein with phage bound was captured on streptavidin coated magnetic beads. Unbound phage were washed away. Bound phage were then rescued as described by Vaughan et al and the selection process was repeated. Three rounds of selection were carried out at reducing antigen concentrations. A representative proportion of scFvs from the output of selection rounds were subjected to DNA sequencing.

Following these initial selections from the phage display library, a panel of unique scFv were identified in a ligand binding assay, which was designed to identify phage expressing scFv antibodies that were capable of inhibiting binding of GM-CSF to purified GM-CSFRα extracellular domain. Neutralising potency of these scFv in the ligand binding assay ranged from 0.65 to 3.3 nM.

Antibodies that were active in the biochemical ligand binding assay were assessed for biological activity in a TF-1 proliferation assay, which measured neutralisation potency by assaying ability of the antibodies to inhibit the proliferation of TF-1 cells stimulated with GM-CSF. TF-1 is a human premyeloid cell line established from a patient with erythroleukemia. This cell line is factor-dependent for survival and proliferation and is routinely maintained in human GM-CSF. Inhibition of GM-CSF dependent proliferation was determined by measuring the reduction in incorporation of tritiated thymidine into the newly synthesised DNA of dividing cells. All of the scFv had measurable potency in this assay, with IC50 values ranging from about 180 to 1200 nM.

The most potent scFv clones were reformatted as human IgG4 antibody molecules with a human gamma 4 heavy chain constant domain and a human lambda light chain constant domain. Vectors were constructed for the most potent scFv clones in order to allow expression of the antibodies as whole IgG4 antibody as described by Persic et al. with a few modifications. An oriP fragment was included in the vectors to facilitate use with the HEK-EBNA 293 cells and to allow episomal replication. The VH variable domain was cloned into the polylinker between the secretion leader sequence and the human gamma 4 constant domain of the expression vector pEU8.1 (+). The VL variable domain was cloned into the polylinker between the secretion leader sequence and the human lambda constant domain of the expression vector pEU4.1 (−). HEK-EBNA 293 cells were co-transfected with the constructs expressing heavy and light chain and whole antibody was purified from the conditioned media using protein A affinity chromatography. The purified antibody preparations were sterile filtered and stored at 4° C. in phosphate buffered saline (PBS) prior to evaluation. Protein concentration was determined measuring absorbance at 280 nm using the BCA method (Pierce).

The re-formatted IgG were compared to the known murine antibody 2B7 in the TF-1 proliferation assay. The IgG4s retained or gained activity in this assay, with IC50 values ranging from 6 to about 1600 nM.

In inflammatory disease, the shape change of neutrophils is necessary for their recruitment to the site of action. A human granulocyte shape change assay was designed to mimic this biological response using fluorescence activated cell sorting (FACS) to measure the change in shape of granulocytes isolated from blood following their exposure to GM-CSF. The ability of anti-GM-CSFRα IgG4 antibodies to inhibit the shape change response of neutrophils to GM-CSF was assessed, and IC50 values of selected clones ranged from about 15 to 350 nM. A representative antibody 28G5 neutralized cynomolgus GMCSF-R in the cynomolgus granulocyte shape change assay with an IC50 of about 5 nM. The known murine antibody 2B7 was also able to neutralise the biological response resulting from GM-CSF binding to the cynomolgus receptor.

Receptor binding affinity of the antibodies was then measured using BIACORE®, with calculated $K_D$ values ranging from 32 to 377 nM.

Optimisation

In an effort to improve the potency of 28G5 an optimisation programme was initiated. Libraries of antibodies were produced where random mutagenesis of the $V_H$ or $V_L$ CDR3s was carried out. Each CDR3 was randomised in two blocks of 6 amino acids in order to cover the entire CDR, producing libraries H1 (N terminal block of 6 aa VH CDR3), H2 (C terminal block of 6 aa in VH CDR3), L1 (N terminal block of 6 aa in VL CDR3) and L2 (C terminal block of 6 aa in VL CDR3). The resulting libraries were subjected to repeated selection cycles for binding to human GM-CSFRα. Clones isolated from this selection process were then used to construct a combined phage library which contained scFv with both mutated heavy chain CDR3s and mutated light chain CDR3s. These libraries were also subjected to same selection procedure.

At each stage of the optimisation process, scFv that were able to inhibit the binding of 28G5 IgG4 to the GM-CSF receptor were identified using an epitope competition assay with 28G5 and the receptor, and were then assessed in the TF-1 proliferation assay, as described below.

Following random mutagenesis of heavy chain CDR3 sequences of 28G5, a panel of scFv were identified with measurable neutralisation potency in the TF-1 assay. Most of the potency improvements were obtained when the 3' end of the VH CDR3 was randomised.

Following random mutagenesis of light chain CDR3 sequences of 28G5, a panel of scFv were identified with measurable neutralisation potency in the TF-1 assay. All of the potency improvements were obtained when the 3' end of the $V_L$ CDR3 was randomised.

Following combination of the heavy and light chain CDR3 random mutagenesis libraries, a panel of scFvs were identified with improved potency in the TF-1 proliferation assay over the parental scFv 28G5. ScFv with potency improvements of >60000 fold over parent 28G5 were isolated. All combinations of the libraries resulted in improved scFv, i.e. H1/L1, H1/L2, H2/L1, H2/L2. This is of particular interest because no improved scFvs were isolated from the L1 library.

A panel of 19 scFv identified during the optimisation of 28G5 were reformatted and expressed as IgG4s, using the methods described above. The panel was composed of antibody clones 1, 2 and 4 to 20. Some of the most potent clones in this panel were obtained from the combined H and L CDR3 mutagenised libraries. The IgG4 antibodies in this panel were assessed for their activity in the TF-1 proliferation assay and were compared to the known murine antibody 2B7. All of the optimised IgG4s were more potent than 2B7 in this assay. On this occasion 2B7 had a calculated IC50 of about 1.6 nM, whereas the clones had calculated IC50 values ranging from about 1 pm to about 1100 pM. Data are presented in Table 1 below and summarised as follows:

IC50<1500 pM Antibodies 1, 2 and 4 to 20

IC50<300 pM Antibodies 1, 2, 4-12 and 14-20

IC50<60 pM Antibodies 1, 2, 4-6, 8-11, 14 and 16-20

IC50<10 pM Antibodies 1, 5, 6, 11 and 20.

FIG. 3 illustrates antagonist potency of two representative antibodies of the invention, Antibody 1 and Antibody 6, in comparison with the known antibody 2B7 in the TF-1 proliferation assay.

The BIACORE® 2000 System (Pharmacia Biosensor) was used to assess the kinetic parameters of the interaction of some of the lead-optimised IgG4s with recombinant purification-tagged GM-CSF receptor extracellular domain. The affinity of the antibodies was much improved, with calculated $K_D$ values from 0.127 nM to about 5 nM. Data are shown in Table 2. Improvements were obtained in both on-rates and off rates. The correlation between the affinity of the IgG4s for the soluble extracellular domain of GM-CSFR α and their performance in the TF-1 assay was very good with a Pearson coefficient of 0.85 (p<0.0001). By way of comparison, KD of 2B7 was separately calculated and was shown to be about 7 nM.

IgG4 antibodies identified during the optimisation of 28G5 were assessed in the human granulocyte shape change assay and were compared to the known murine antibody 2B7. All of the antibodies that were assessed in this assay (antibodies 1, 2, 5, 6, 9-11, 16 and 20) were very potent with IC50s ranging from 7.8 to 90 pM. Of these, antibodies 1, 2, 5, 6, 9, 16 and 20 had IC50s less than 50 pM, and antibodies 1, 2, 6, 16 and 20 had IC50s less than 25 pM. Our antibodies were more potent than 2B7, which had an IC50 of 477 pM. Data are shown in Table 3. FIG. 4 illustrates antagonist potency of two representative antibodies of the invention, Antibody 1 and Antibody 6, in comparison with the known antibody 2B7 in the human granulocyte shape change assay.

IgG4 antibodies identified during the optimisation of 28G5 were assessed in the cynomolgus granulocyte shape change assay. All of the antibodies were able to neutralise the activity of GM-CSF at the cynomolgus receptor as well as at the human receptor and all of the antibodies were more potent than 2B7. 2B7 had an IC50 of 26 pM whereas representative antibodies (Antibody 6, Antibody 1 and Antibody 2) from the panel had IC50 values of 1.73, 2.03 and 3.2 pM, respectively.

A panel of the IgG4s identified during the optimisation of 28G5 were assessed for their neutralisation potency in the monocyte TNFα release assay. This assay tests for ability to inhibit release of the proinflammatory factor TNFα from human monocytes when they are treated with GM-CSF. Antibodies 1, 2, 5, 6, 9 and 10 were tested and all were active in this assay and were able to fully neutralise the action of GM-CSF at its receptor (IC50 ranging from about 43 to 139) whereas at a concentration of 333 nM 2B7 could only achieve 50% inhibition of GM-CSF induced TNFα release, indicating that this antibody is only a partial inhibitor in this assay. FIG. 5 illustrates antagonist potency of two representative antibodies of the invention in comparison with the known antibody 2B7 in the monocyte TNFα release assay. Data are shown in Table 4 and are summarised as follows:

<150 pM Antibody nos 1, 2, 5, 6, 9 & 10

<110 pM Antibody nos 1, 2, 5, 6 & 9

<100 pM Antibody nos 1, 5, 6 & 9

A hallmark of inflammatory disease is the enhanced survival of inflammatory cell types in response to particular signals. Granulocytes are able to survive for longer in the presence of GM-CSF and so the ability of the IgG4 antibodies isolated during the optimisation of 28G5 to inhibit this response was assessed in a granulocyte survival assay. All of the anti-GM-CSFRα IgG4s from lead optimisation were active in this assay, and representative neutralisation potencies (IC50) ranged from 7.0 to 843.7 pM. This is in contrast to the known murine antibody 2B7 which was completely inactive up to a concentration of 83 nM. FIG. 6 illustrates antagonist potency of two representative antibodies of the invention, Antibody 1 and Antibody 6, in comparison with the known antibody 2B7 in the granulocyte survival assay.

These data, as illustrated in FIGS. 3 to 6, indicate that our antibodies have significantly different properties compared with the known murine antibody 2B7. For example, representative antibodies of the invention inhibited granulocyte survival and TF-1 proliferation stimulated with 7 pM GM-CSF in the granulocyte survival and TF-1 proliferation assays respectively, whereas 2B7 did not inhibit granulocyte survival but did inhibit TF-1 proliferation (albeit to a lesser extent than our antibodies). The data indicate that binding members of the invention have higher affinity and improved ability to inhibit a variety of biological effects mediated through GM-CSF-R compared with known anti-GM-CSFRα antibodies.

The derived amino acid sequence of 28G5 and its derivatives were aligned to the known human germline sequences in the VBASE database and the closest germline identified by sequence similarity. The closest germline for the VH domain of 28G5 and its derivatives was identified as VH1 DP5. The 28G5 VH has 14 changes from the VH1-24 (DP5) germline within framework regions. The closest germline for the VL domain is Vlambda1 VL 1-e (DPL8), which has only 5 changes from the germline within the framework regions. Framework regions of 28G5 and its derivatives were returned to germline by site directed mutagenesis to identically match native human antibodies. All except one amino acid could be converted to germline with only modest changes in antibody potency. The amino acid isoleucine at position 94 of the heavy chain (using Kabat numbering, Kabat et al. 1971) could not be changed to the germline threonine without a complete loss of activity. This single change from germline was therefore maintained in the antibody framework region.

A full $pA_2$ analysis of two of the anti-GM-CSFRα antibodies, Antibody 6 and Antibody 1, was carried out in the TF-1 proliferation assay. The data confirms that these antibodies are highly potent antagonists in this system with calculated $pA_2$ values of −11.3±0.2 and −11.0±0.2 respectively (FIG. 1).

A full $pA_2$ analysis of one of the anti-GM-CSFRα antibodies, Antibody 6, was carried out in the human and cynomolgus granulocyte shape change assays. The data confirm that this antibody is a highly potent antagonist in these systems with calculated $pA_2$ values of −10.58 and −10.78 in the human and cynomolgus assays respectively (FIG. 2).

Figure 7:
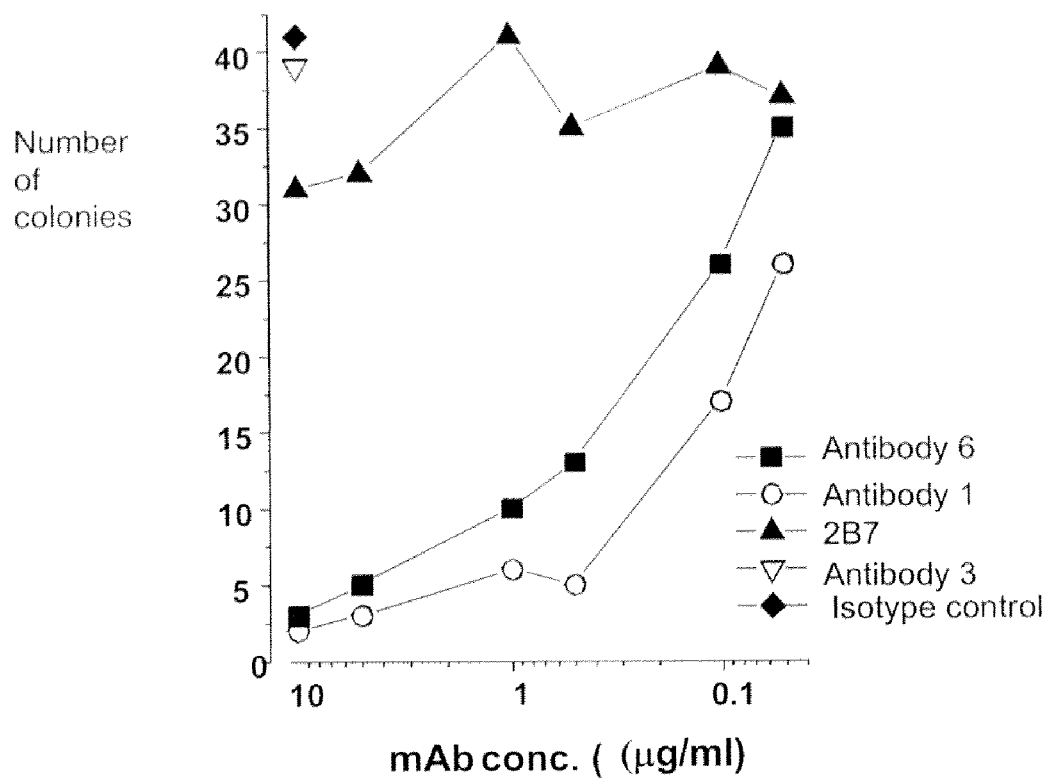
FIG. 7. Affinity matured human mAbs Antibody 1 and Antibody 6, but not the parent human mAb 28G5 (Antibody 3) or the known murine antibody 2B7, inhibit GM-CSF driven differentiation of human hemopoietic progenitors. $5 \times 10^4$ thawed mononuclear cells from an apheresis sample were cultured in semi-solid agar in the presence of 10 ng/ml GM-CSF and the indicated concentration of mAb. Colonies were counted at day 14. Graph shows number of colonies against mAb concentration in μg/ml.

GM-CSF drives the differentiation of haemopoietic progenitor cells into granulocyte and macrophage colonies in semi-solid agar assays. Affinity matured Antibody 6 and Antibody 1, the parent mAb Antibody 3 (28G5) and a negative control (CAT001) were therefore assessed for their ability to antagonise this GM-CSF specific activity using progenitor cells derived from peripheral blood, in a colony formation assay. Data presented in FIG. 7 demonstrates that both affinity matured representative mAbs were potent inhibitors of in vitro haemopoietic colony formation mediated by human GM-CSF.

Approximate $IC_{50}$ values were 0.08 μg/ml (Antibody 6) and 0.25 μg/ml (Antibody 1) for the affinity matured mAb. Interestingly the known murine antibody 2B7 appeared to have little if any inhibitory activity in this assay up to a concentration of 66 nM.

In control experiments the affinity matured mAb had no effect on colony formation mediated by the combination of SCF+IL-3+G-CSF as expected and, in the absence of cytokines, colony formation was negligible (<4 colonies/culture).

Figure 8:
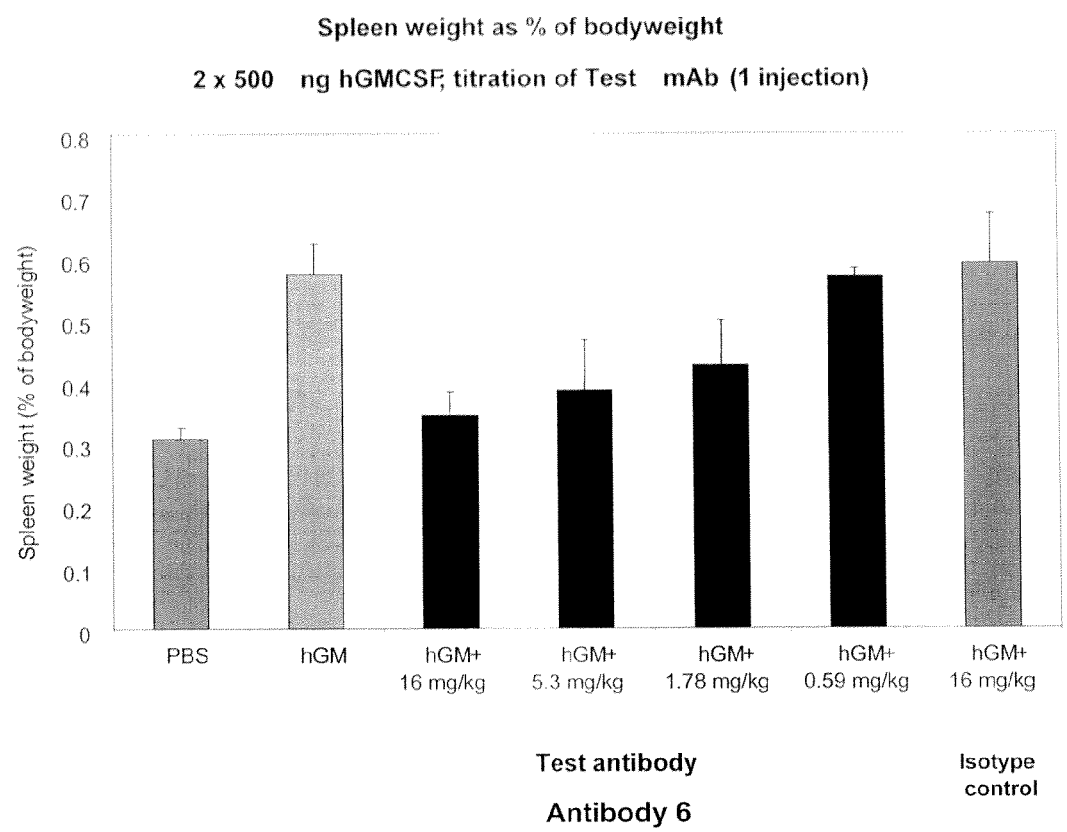
FIG. 8. Dose-response analysis of the efficacy of affinity matured mAb in huGM-CSFR Tg chimeric mice. Groups of 5 Tg chimeric mice were treated with 500 ng huGM-CSF (or PBS) s.c twice daily for 4 days (D.1-D.4) and either control (CAT001) or test mAb (Antibody 6) at the indicated concentrations on D.0, Spleen weights were assessed on D.5.

For in vivo analysis of huGM-CSFRα specific mAb antagonist activity, transplantation of bone marrow from transgenic (Tg) mice expressing both the α and the β chains of human GM-CSFR into wildtype mice can be used to generate chimeric animals such that transgenic huGM-CSFR expression is limited to bone marrow derived haemopoietic cells and thus more closely resembles the expression profile of the endogenous receptor. In these Tg chimeric mice the administration of huGM-CSF leads to an increase in spleen weight and the marginalisation of circulating blood monocytes. Affinity matured Antibody 6 and a negative control mAb, CAT001 were assessed for their ability to antagonise these GM-CSF mediated in vivo responses. For dose-response analysis 6 groups of 5 Tg chimeric mice were treated with 500 ng huGM-CSF s.c twice daily for 4 days (day 1-4) and a seventh control group of five animals received PBS only. Four of the 6 groups of huGM-CSF treated animals received test mAb (Antibody 6) at 16 mg/kg, 5.3 mg/kg, 1.78 mg/kg or 0.59 mg/kg at D.0 while a fifth group of the huGM-CSF treated animals received control CAT001 at 16 mg/kg at D.0. Results presented in FIG. 8 demonstrate that, compared with control PBS, treatment with huGM-CSF induced a significant increase in spleen weight and a decrease in circulating blood monocytes. As expected, treatment with 16 mg/kg control CAT001 had no effect on either the increase in spleen weight or the decrease in blood monocytes. In contrast there was a clear dose-response effect following treatment with the test mAb Antibody 6, as at 16 mg/kg this antibody abolished the increase in spleen weight and, while still apparent, the effect was greatly reduced at 0.59 mg/kg of mAb. The $IC_{50}$ would appear to be somewhere between 0.59 mg/kg and 1.78 mg/kg. A similar result was observed for the GM-CSF induced decrease in circulating monocytes-treatment with test mAb Antibody 6 at 16 mg/kg abolished the decrease, while mAb at 0.59 mg/kg had only a minor impact on this response. These data show that the anti-GM-CSFRα antibody is an antagonist of human GM-CSFRα in vivo.

To further investigate the anti-inflammatory properties of these anti-GM-CSFRα antibodies, Antibody 6 was evaluated in a peripheral blood mononuclear cell cytokine release assay. In this assay TNFα and IL-6 can be endogenously released depending on the donor. In this assay the GM-CSF is also endogenously produced by the cells, rather than exogenously added, and therefore results observed in this assay represent inhibition of the biological effects of native endogenous GM-CSF binding to its receptor.

Figure 9:
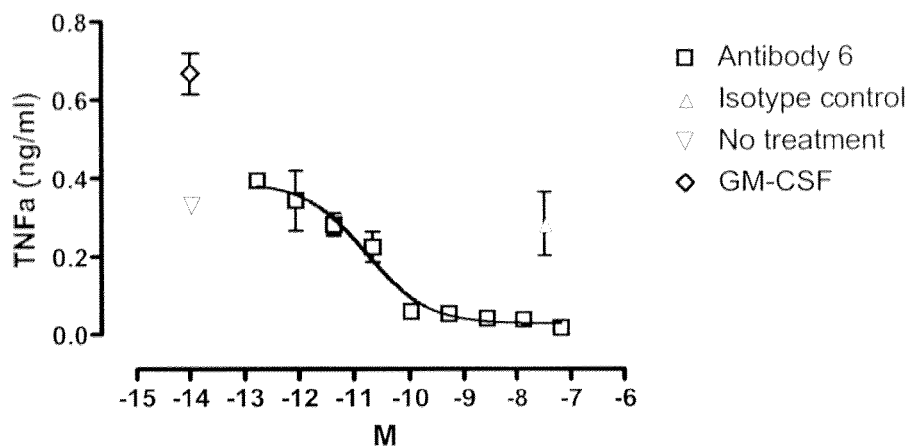
FIG. 9. Dose-response analysis of the efficacy of Antibody 6 in a human peripheral blood mononuclear cell endogenous cytokine release assay. $1 \times 10^6$ cells were cultured for 72 hrs in the presence and absence of antibody and an IL-6 and TNFα ELISA performed on the supernatants. Data represent the mean inhibition with standard deviation bars of duplicate determinations within the same experiment.
Figure 9:
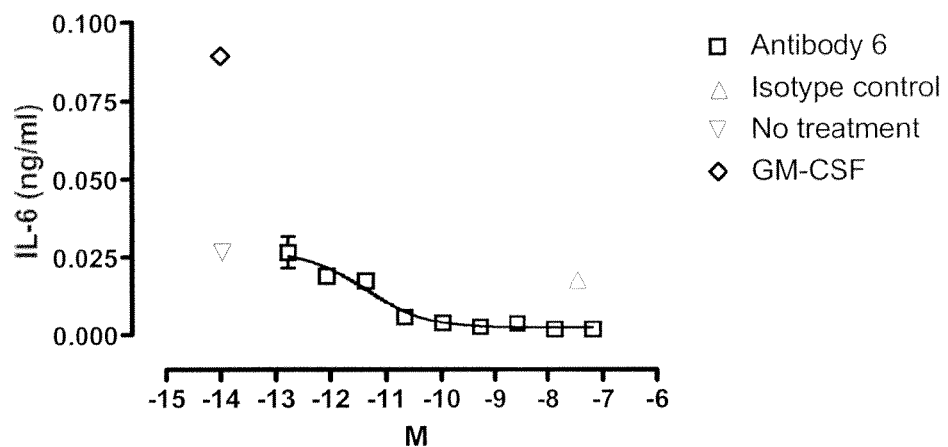

Following administration of antibody 6 both these cytokines were dose dependently inhibited as illustrated in FIG. 9. These data indicate that these antibodies can inhibit the activity of native GM-CSF and that by inhibiting GM-CSF signalling one can inhibit key pro-inflammatory cytokines, such as IL-6 and TNFa, both of which being implicated in a number of inflammatory indications such as rheumatoid arthritis.

Furthermore, based on this result with Antibody 6 it can be expected that each of antibodies 1 to 20 would also demonstrate inhibition in this assay, since all of antibodies 1 to 20 are believed to bind the same region of GM-CSFRa.

Mapping of Residues Important for Antigen Recognition, and Sequence Analysis

We determined the variability of residues at positions in the germlined Antibody 6 scFv sequence in order to identify which positions are normally conserved for ligand binding and which positions are variable in an antibody that still retains ligand binding activity.

Positions contributing to antigen binding appeared to be Kabat residues 27A, 27B, 27C, 32, 51, 52, 53, 90, 92 and 96 in the VL domain and Kabat residues 17, 34, 54, 57, 95, 97, 99 and 100B in the VH domain.

Seven positions that appeared to be important for antigen binding were identified: H95, H97, H99, H100B, L90, L92 and L96. We then analysed the residues at these positions in sequences of 160 variants isolated during the 28G5 antibody optimisation process, all of which showed a minimum 5-fold improvement in potency in the TF-1 proliferation assay.

Data in Table 5 below summarise the different amino acids (out of a possible 20) that were observed in each of these positions, and at L95A. Where positions are strongly conserved to the amino acids present in 28G5 and/or Antibody 6, this is good evidence that those amino acids are key to binding the antigen. For example, the residues at the following positions are strongly conserved: H97, H100B, L90, L92.

Method

The DNA sequence encoding the affinity matured and germlined Antibody 6 scFv was converted to ribosome display format, essentially as described in ref. [101]. Error prone PCR was performed on the Antibody 6 sequence, using the high mutation conditions (7.2 mutations per 1,000 bp) in the manufacturer's protocol (BD Bioscience), in order to create a library of variant 574D04 sequences containing random point mutations. This library was expressed on ribosomes and incubated with purification-tagged GM-CSFRα to allow binding to occur. Variants able to bind to tagged GM-CSFRα were captured and removed using paramagnetic beads coated with protein G (Dynal). The unbound variants remaining in the population were added to a pool of four biotinylated anti-idiotypic antibodies, which had previously been derived from the large human antibody phage display library described in ref. [102] and were known to bind to the Antibody 6 scFv. Variants bound by the biotinylated anti-idiotypic antibodies were captured with streptavidin beads whilst unbound variants were washed away. This process was repeated for two further rounds of ribosome display selection, following the general methodology of ref. [101].

A representative proportion of variants from the selection outputs was cloned into a phagemid vector and the scFv variants were expressed on phage for testing by ELISA, using the same method as described in Edwards B M et al (2003) Journal of Molecular Biology Vol 334:103. Those variants that did not display binding to purification-tagged GM-CSFRα were tested for binding to the pool of four anti-idiotypic antibodies which were used in the selection. Variants which, in the anti-idiotype binding assay, demonstrated binding which was equal to or greater than the Antibody 6 scFv were sequenced and the sequences were analysed to find positions at which there was a high frequency of mutation.

The average mutation rate of the population of variants was found to be 3.05 amino acids per $V_H$ or $V_L$ chain, using 486 sequences for the $V_H$ chains and 451 sequences for the $V_L$ chains. They were analysed for mutational hotspots, plotting frequency of mutation in relation to their position along the scFv. The analysis focussed on those clones with at least one CDR mutation per $V_H$ and $V_L$ and less than 4 mutations per $V_H$ and $V_L$. From this panel of 123 $V_H$ and 148 $V_L$ sequences, hotspots were defined as those that had a mutational frequency of 5% or more.

Seven positions within $V_H$CDR3 and $V_L$CDR3 of Antibody 6 were highlighted as putative positions important for antigen binding using the ribosome display negative selection method. An analysis was then performed on 160 sequence variants isolated during the 28G5 antibody optimisation process, in which the entire $V_H$CDR3 and $V_L$CDR3 sequences were randomised and selected for higher affinity. All sequences (including Antibody 6) are variants of 28G5 which showed a minimum 5-fold improvement in potency in the TF-1 proliferation assay.

Determination of Linear Epitope

We screened Antibody 6 and the known antibody 2B7 against 2442 peptides, each representing short regions of amino acid sequence from the extracellular portion of GM-CSFR-α, using a PEPSCAN method. Binding signals for each antibody against all the peptides were averaged to generate a mean background signal and for each peptide a signal/background ratio was calculated. For both Antibody 6 and 2B7 a signal/background ratio of four or greater was counted as a specific, positive signal. The sequences of peptides giving a specific, positive signal were analysed for conserved binding motifs and it was found that Antibody 6 bound preferentially to a YLDFQ motif, corresponding to residues 226 to 230 of mature human GM-CSFRα, and the 2B7 antibody bound preferentially to a DVRI motif, corresponding to residues 278 to 281 of mature human GM-CSFRα. Amino acid sequence numbering for the mature receptor is as set out in SEQ ID NO: 206.

PEPSCAN Method (Peptide-Binding Scan)

Overlapping mostly 15-mer synthetic peptides having sequences derived from GMCSF were synthesized and screened using credit-card format mini-PEPSCAN cards (455-well-plate with 3 μl wells) as described previously [103]. Binding of antibodies to each peptide was tested in a PEPSCAN-based enzyme-linked immuno assay (ELISA). 455-well credit card-format polypropylene cards containing the covalently linked peptides were incubated with sample (for example 10 μg/ml antibody or serum diluted 1/1000 in a PBS solution which contains 5% horse-serum (v/v) and 5% ovalbumin (w/v)) and 1% Tween80 or in case of mild blocking in a PBS solution with 4% horse-serum (v/v) and 1% Tween80 (4° C., overnight). After washing, the peptides were incubated with an anti-antibody peroxidase (dilution 1/1000, for example rabbit-anti-mouse peroxidase, Dako) (1 hr, 25° C.), and subsequently, after washing the peroxidase substrate 2,2'-azino-di-3-ethylbenzthiazoline sulfonate (ABTS) and 2 μl/ml 3% $H_2O_2$ were added. After 1 hr the colour development was measured. The colour development of the ELISA was quantified with a CCD-camera and an image processing system. The setup consists of a CCD-camera and a 55 mm lens (Sony CCD Video Camera XC-77RR, Nikon micro-nikkor 55 mm f/2.8 lens), a camera adaptor (Sony Camera adaptor DC-77RR) and the Image Processing Software package Optimas, version 6.5 (Media Cybernetics, Silver Spring, Md. 20910, U.S.A.). Optimas runs on a pentium computer system.

Assay Materials and Methods

Biochemical Ligand Binding Assay

Purified scFv preparations were prepared as described in Example 3 of WO01/66754 [104]. Protein concentrations of purified scFv preparations were determined using the BCA method [105]. Fluoronunc™ 96 well microtitre plates were coated overnight at 4° C. with 50 μl/well of anti-human IgG4 diluted to 2.5 μg/ml in PBS. Plates were washed 3 times with 300 μl/well of PBS/0.1% Tween-20 before blocking for 1 hour at room temperature with 300 μl/well of 30 BSA in PBS. Plates were washed again 3 times with 300 μl/well of PBS/0.1% Tween-20 and then 50 μl of human GM-CSFRα diluted to 62.5 ng/ml in 1% BSA/PBS was added to each well and the plates were incubated for 1 hour at room temperature. After washing 3 times as described above, 25 μl of sample material was added to each well followed by 25 μl of biotinylated GM-CSF diluted to 2 nM in 1% BSA/PBS. To define total binding, buffer only was used as the sample material. To define non-specific binding, unlabelled GM-CSF diluted to 100 nM in 1% BSA was used as the sample material. Plates were incubated for 1 hour at room temperature before washing 3 times as described above. 50 μl of europium labelled streptavidin (PerkinElmer) diluted to 100 ng/ml in DELFIA™ assay buffer was added to each well of the plate and was incubated for 30-60 minutes at room temperature before washing 7 times with DELFIA™ wash buffer. 50 μl/well of DELFIA™ enhancement solution was added to the plates and the samples were read at 615 nm on a platereader.

TF-1 Proliferation Assay

TF-1 cells, obtained from R&D Systems and routinely maintained in RPMI 1640, 10% FBS, 1 mM sodium pyruvate and 4 ng/ml GM-CSF, were starved by washing 3 times in assay medium (RPMI 1640, 5% FBS, 1 mM sodium pyruvate), resuspending in assay medium and incubating for 7-24 hours at 37° C. in 5% $CO_2$. Cells were then resuspended at $1\times10^5$/ml in assay medium and 100 µl was added to each well of a 96 well flat-bottomed tissue culture plate. Test samples were prepared by sterile filtering the stock sample prior to diluting in assay medium. 50 µl of test material was then added to each well of cells and these were incubated for 45-60 mins at 37° C. in 5% $CO_2$. 50 µl of GM-CSF diluted to the $EC_{80}$ value in assay medium (or 0.4 ng/ml for some batches of GM-CSF) was then added to each well and the plates were incubated for 16 hours at 37° C. in 5% $CO_2$ in a humidified chamber. This represents a final concentration of 7 pM GM-CSF. In order to measure the proliferation of the cells, 20 µl of $^3$H-thymidine diluted to 5.0 µCi/ml in assay medium was added to each well of the plate and the plates were incubated for 4 hours ±30 mins at 37° C. in 5% $CO_2$. Cells were then harvested onto 96 well GF/C UNIFILTER® plates using a plate harvester and washed. After adding 50 µl MicroScint 20™ to each well of the filter plate, the plates were sealed and counted on a TOPCOUNT® plate reader.

Human Granulocyte Shape Change Assay

Human buffy coats (human blood pack from the Blood Transfusion service) were mixed in an equal volume of 3% Dextran T-500 in 0.9% NaCl. The mixture was then incubated in an upright position until an interface had formed. The upper layer was harvested and layered on top of a HISTOPAQUE® 1.077 density gradient which was then centrifuged at 400 g for 40 minutes and allowed to stop without braking. The upper layers of this gradient were removed leaving the granulocyte pellet. Any remaining red blood cells in the pellet were lysed by resuspending the cells in 20 ml of ice cold water for 30s followed by the immediate addition of ice cold 1.8% sodium chloride. Cells were then repelleted at 1200 rpm and resuspended in assay medium (RPMI1640, 10% FBS, 100 u/ml Penicillin, 100 µg/ml streptomycin, 25 mM HEPES) at $1\times10^6$/ml. 100 µl of cells was then added to each well of a 96 well flat bottomed tissue culture plate. Test samples were prepared by sterile filtering the stock samples and diluting, as appropriate, in assay medium.

For lead isolation, 50 µl of test sample was then added to the cells and the plates were incubated for 45-60 mins at 37° C. in 5% $CO_2$. This represents a final concentration of 7 pM GM-CSF. This was followed by the addition of 50 µl of GM-CSF diluted to 0.4 ng/ml in assay medium to each well and a 4 hour incubation at 37° C. in 5% $CO_2$ in a humidified chamber.

For lead optimisation, filtered IgG4s diluted in assay medium were mixed with an equal volume of GM-CSF at 0.4 ng/ml in assay medium. This represents a final concentration of 7 pM GM-CSF. 100 µl of antibody/GM-CSF mix was then added to each well. This was followed by a 3 hour incubation at 37° C. in 5% $CO_2$ in a humidified chamber.

Cold formaldehyde was added to a final concentration of 1.25% and cells were fixed overnight at 4° C. 2000-5000 events per well were analysed by flow cytometry. The geometric mean of the forward scatter (FSC) for each sample was then derived using CellQuest. Cells were gated to exclude irrelevant populations (e.g. dead cells/debris) when calculating the geometric mean.

Cynomolgus Granulocyte Shape Change Assay

Antibodies were assessed in an assay measuring the shape change of cynomolgus granulocytes following stimulation with GM-CSF. Granulocytes were purified from whole cynomolgus blood and the assay was carried out essentially as described for the human granulocyte shape change assay.

Binding Affinity Data Using Biosensor Analysis

The BIACORE® 2000 System (Pharmacia Biosensor) was used to assess the kinetic parameters of the interaction between scFvs and IgG4s with the recombinant receptors. The Biosensor uses the optical effects of surface plasmon resonance to study changes in surface concentration resulting from the interaction of an analyte molecule with a ligand molecule that is covalently attached to a dextran matrix. Typically the analyte species in free solution is passed over the coupled ligand and any binding is detected as an increase in local SPR signal. This is followed by a period of washing, during which dissociation of the analyte species is seen as a decrease in SPR signal, after which any remaining analyte is stripped from the ligand and the procedure repeated at several different analyte concentrations. A series of controls are usually employed during an experiment to ensure that neither the absolute binding capacity nor kinetic profile of the coupled ligand change significantly. A proprietary HEPES buffer saline (HBS-EP) is typically used as the main diluent of analyte samples and dissociation phase solvent. The experimental data is recorded in resonance units (directly corresponding to the SPR signal) with respect to time. The resonance units are directly proportional to the size and quantity of analyte bound. The BIAevaluation software package can then be used assign rate constant to the dissociation phase (dissociation rate units $s^{-1}$) and association phase (association rate units $M^{-1} s^{-1}$). These figures then allow calculation of the Association and Dissociation Affinity Constants.

The affinity of IgG4 was estimated using a single assay in which the IgG4 was non-covalently captured by amine protein A surface. A series of dilutions of recombinant purification-tagged GM-CSF receptor extracellular domain, from 100 to 6.25 nM were then sequentially passed over the IgG4. The molarity of the receptor was calculated using the concentration (Bradford) and the predicted non post-translationally modified mature polypeptide mass (39.7 kDa). Each of the two separate sets of data were analysed in identical formats. Reference cell corrected data was subject to fitting using the 1:1 langmuir model set for simultaneous global calculation of the association and dissociation rates, with the Rmax value set to global. The level of IgG4 captured during each cycle was assessed to ensure that the quantity captured remained stable during the entire experiment. Additionally, the dissociation rate of the IgG4 was assessed to determine if a correction for baseline drift was required. However, both the protein A interactions proved to be sufficiently reproducible and stable. The validity of the data was constrained by the calculated chi2 and T value (parameter value/offset), which had to be <2 and >100 respectively.

Production of purification-tagged GM-CSFRα extracellular domain: A pEFBOS expression vector [106] incorporating a sequence encoding human GM-CSF receptor α extracellular domain (SEQ ID NO: 205, representing amino acids 1 to 298 of the mature GM-CSF R) with a murine IL-3 signal sequence and incorporating an N-terminal purification tag was used to produce recombinant N-terminal tagged GM-CSF receptor extracellular domain (ECD) polypeptide. The tagged ECD polypeptide was expressed in CHO cells using the pEFBOS vector using standard procedures. This polypeptide may also be referred to as purified GM-CSFRα extracellular domain, or as the soluble extracellular domain of GM-CSFRα.

Any suitable purification tag may be used e.g. Flag peptide (DYKDDDE—SEQ ID NO: 204), Fc, biotin or his tag. Purification can be conducted using any appropriate technique, e.g. a Flag-tagged ECD polypeptide (SEQ ID NO: 203) may be purified on an M2 affinity chromatography column and eluted with FLAG peptide.

Monocyte TNFα Release Assay
Purification of Monocytes (Monocyte Isolation Kit—Miltenyi Biotec—130-053-301):

Human buffy coats (human blood pack from the Blood Transfusion service) were layered on top of a HISTOPAQUE® 1.077 density gradient (Sigma, Cat No. 1077-1) and cells were centrifuged at 400×g for 40 minutes. No brake was applied when stopping the centrifuge. PBMC cells were then harvested from the interface. Cells were washed in PBS and pelleted at 300×g for 10 mins before the remaining red blood cells were lysed by resuspension in 20 ml of ice cold water for 15 s followed by the immediate addition of ice cold 1.8% NaCl. Cells were then pelleted at 1200 rpm for 5 mins and resuspended in 600 µl of MACS buffer (PBS, 2 mM EDTA). 200 µl of Fc blocking reagent provided with the kit was added to the cells and mixed before adding 200 µl of Hapten-antibody cocktail (also provided with the kit) and mixing. Cells were then incubated at 4° C. for 15 mins before washing twice in 50 ml of MACS buffer. The cell pellet was resuspended in 600 µl of MACS buffer before adding 200 µl of Fc blocking reagent and mixing followed by 200 µl of MACS anti-hapten microbeads and mixing. The cells were incubated for 45 mins at 4° C. before washing in 50 ml MACS buffer and resuspending in 500 µl of MACS buffer. A single column (Miltenyi Biotec 130-042-401) was prepared by washing through with 3 ml of MACS buffer before the cell suspension was applied to the column. The effluent was collected as the enriched monocyte fraction. The column was washed with 2×3 ml MACS buffer and the effluent was collected. Monocyte purity was checked by staining with anti-CD14-PE using standard flow cytometry methods. Cells were finally resuspended at $4 \times 10^6$/ml in assay medium (RPMI 1640, 10% FCS, 100 U/ml penicillin, 100 µg/ml streptomycin).

Stimulation of Monocytes:

50 µl of cells were added to each well of a COSTAR® 96 well flat-bottomed tissue culture plate. 25 µl of 150 µg/ml rhIFNγ (R&D Systems) was added to all wells. Filtered IgG4s diluted in assay medium were mixed with an equal volume of GM-CSF at 56 ng/ml (4 nM) in assay medium. This represents a final concentration of 1 nM GM-CSF. 75 µl of antibody/GM-CSF mix was then added to each well. Controls were wells with GM-CSF only or with no GM-CSF and no antibody. Plates were then incubated for 18 hours at 37° C. with 5% $CO_2$ in a humidified chamber. The supernatant was then harvested to test for TNF-α levels by ELISA.

TNFα ELISA (R&D Systems ELISA Development System DY210):

FLUORONUNC™ Immunosorb ELISA plates were coated overnight at room temperature with 100 µl of capture antibody at 4 µg/ml in PBS. Plates were then washed three times with PBS/0.1% Tween and blocked with 300 µl/well of 3% Marvel in PBS for 1 hour at room temperature. Plates were washed 3 times with PBS/0.1% Tween. 100 µl of the supernatant from the assay plates was transferred to the ELISA plate and a titration of TNF-α diluted in assay medium was added to the control wells. Plates were incubated at room temperature for 2 hours before washing 4-5 times with PBS/0.1% Tween. 100 µl of detection antibody diluted to 300 ng/ml in 1% Marvel/PBS was added to each well of the plate and the plates were incubated for a further 2 hours at room temperature before washing 4-5 times with PBS/0:1% Tween. Streptavidin-Europium (PerkinElmer 1244-360) was diluted 1:1000 in DELFIA® assay buffer (PerkinElmer 4002-0010) and added at 100 µl/well before incubating for 45 mins at room temperature. Plates were then washed 7 times in DELFIA® wash buffer before the addition of 100 µl/well of enhancement solution (PerkinElmer 4001-0010) and reading at 615 nm on a platereader.

Granulocyte Survival Assay

Cells were purified from human buffy coats as described for the neutrophil activation assay (shape change assay) washed in assay medium (RPMI-1640 GLUTAMAX™, 10% FBS, 100 U/ml Penicillin, 100 µg/ml streptomycin) and resuspended at $1 \times 10^6$/ml in assay medium. 100 µl of cells were added to each well of a COSTAR® 96 well flat-bottomed tissue culture plate. Filtered stocks of antibody were diluted in assay medium and mixed with an equal volume of GM-CSF at 0.4 ng/ml. This represents a final concentration of 7 pM GM-CSF. Control wells contained media alone or GM-CSF alone. 100 µl of the test sample/GM-CSF mix was then added to each well on the plate and the cells were incubated for 68 hours at 37° C./5% $CO_2$ in a humidified chamber. 20 µl of ALAMARBLUE® was added to each well and the plates were incubated for a further 24 hours at 37° C./5% $CO_2$ in a humidified chamber. Plates were then read at 560 nm and 590 nm on a platereader.

$pA_2$ Analysis of Anti-GM-CSFRα Antibodies in the TF-1 Proliferation Assay and in the Human and Cynomolgus Granulocyte Shape Change Assays The main pharmacological tool to quantify the affinity of a competitive antagonist is Schild analysis. Using this approach a system-independent means of estimating the antagonist affinity in a functional assay maybe determined. The method is based on the concept that the antagonist concentration and its affinity determines the antagonism of the agonist response. Because the antagonism can be quantified and the concentration of the antagonist is known, the affinity of the antagonist can be determined. This antagonism is quantified by measuring the ratio of equiactive concentrations of agonists, measured in the presence and absence of the antagonist, referred to as dose ratios (DR).

Dose ratios may be calculated by taking the ratio of the EC50 of agonist (typically GM-CSF) in the absence of the binding member to the EC50 of the agonist in the presence of a single concentration of binding member. The dose ratios, expressed as log(DR-1) may then be used in a linear regression on log [binding member] to produce a Schild regression. Thus, for every concentration of binding member there will be a corresponding DR value; these are plotted as the regression of log(DR-1) upon log [binding member]. If the antagonism is competitive, there will be a linear relationship between log(DR-1) and log [binding member] according to the Schild equation wherein the equation is as follows $$\text{Log}(DR-1) = \log[A] - \log K_A$$

Under these circumstances, a value of zero for the ordinate will give an intercept of the x-axis where log [a]=log $K_A$. Therefore the concentration of binding member that produces a log(DR-1)=0 will be equal to the log $K_A$, the equilibrium dissociation constant of the binding member-receptor complex. This is a system independent quantification of the binding member affinity that should be accurate for every cellular system containing the receptor.

Because the $K_A$ values are obtained from a logarithmic plot, they are log normally distributed. The negative logarithm of this particular concentration is referred to empirically as pA2, the concentration of antagonist that produces a twofold shift of the agonist dose response curve. The antagonist potency can be quantified by calculating pA2 from a single concentration of antagonist producing a single value for the dose ratio from the equation, wherein $$pA2 = \log(DR-1) - \log[a]$$

[a]=molar concentration of antagonist that makes it necessary to double the agonist concentration to elicit the original submaximal response.

DR=the dose ratio is quantified by measuring the ratio of equiactive concentrations of agonist measured in the presence and absence of the antagonist.

$pA_2$ may be calculated from dose-response assay data.

Inhibition of In Vitro GM-CSF Mediated Differentiation of Blood Cell Progenitors in Colony Formation Assay Peripheral blood mononuclear cells enriched for haemopoietic progenitor cells were obtained from donors who had undergone progenitor cell mobilisation and apheresis as part of their standard clinical management. Samples were de-identified and cells were not cryopreserved prior to use. $5 \times 10^4$ mononuclear cells were cultured in semi-solid agar [107] in the presence of human GM-CSF at a final concentration of 10 ng/ml. Test affinity matured human mAbs, and the known murine antibody 2B7, were added to agar cultures at a final concentration of 10, 5, 1, 0.5, 0.1 or 0.05 μg/ml. The parent human mAb 28G5 and an isotype matched negative control human mAb, CAT001, were assessed at a single concentration of 10 μg/ml. For control purposes mAbs were also assessed for their ability to block colony formation stimulated by a combination of SCF, IL-3 and G-CSF (Croker et al., 2004) and for their impact on colony formation in the absence of cytokines. Colony formation (aggregates of >40 cells) was assessed after 14 days incubation at 37° C. with 10% $CO_2$ in air. Colonies were fixed with glutaraldehyde and counted using a dissection microscope at a magnification of 35×.

Inhibition of GM-CSF Biological Activity In Vivo in Human GM-CSFRαβ Transgenic Mice Transgenic (Tg) mice expressing both the α and the β chains of the human GM-CSFR under the control of an MHC class I promoter have been generated and in vivo spleen and blood cell responses to administration of huGM-CSF have been described [108]. For in vivo analysis of huGM-CSFRα specific mAb antagonist activity, transplantation of bone marrow from the Tg mice into wildtype mice can be used to generate chimeric animals such that transgenic huGM-CSFRαβ expression is limited to bone marrow derived haemopoietic cells and thus more closely resembles the expression profile of the endogenous receptor. In these huGM-CSFRαβ Tg chimeric mice the administration of huGM-CSF leads to an increase in spleen weight and the marginalisation of circulating blood monocytes.

Generation of Tg Chimeric Mice:

Femurs and tibiae from donor Tg mice were removed and the bone marrow flushed out with sterile PBS plus 3% fetal calf serum (FCS).

The bone marrow plugs were then drawn up through a 23 G needle to obtain a single cell suspension, then cells washed once with cold PBS+3% FCS and passed through a stainless steel mesh. Red cells were then removed by lysis in 0.168 M ammonium chloride buffer, after which cells were washed twice more with phosphate buffered saline (PBS)+3% FCS before again being passed through a stainless steel mesh. To further remove dead cells and cell debris the suspension was centrifuged through an FCS cushion. Viable cells are recovered in the pellet, washed once with PBS and resuspended in PBS at $2.5 \times 10^7$/ml. 5 to 8 week old recipient C57/BL6 mice were lethally irradiated with 2 doses of 550 Rad, 3 hours apart. Recipient mice were injected intravenously (i.v) with 0.2 ml cell suspension (ie. $5 \times 10^6$ cells/mouse) and subsequently housed in hooded boxes with 0.02 M neomycin in their drinking water for 3 weeks. Reconstitution was assessed after 6 weeks by FACS analysis of peripheral blood using mAbs specific for the huGMCSFRα and β chains.

GM-CSF Treatment and Subsequent Analysis of Tg Chimeric Mice:

Tg chimeric mice were treated twice daily via the subcutaneous (s.c) route with 500 ng of huGM-CSF for 4 days. For analysis of antibody antagonist activity groups of 5 mice were administered selected doses of mAb (see below) via the intraperitoneal (i.p) route 1 day prior to initiation of GM-CSF treatment. At day 5, 0.2 ml of blood was sampled for analysis of circulating leukocyte populations, in particular blood monocytes, using an ADVIA™ Hematology System (Bayer Diagnostics). Animals were then sacrificed and spleens removed for weight measurement.

Inhibition of Endogenously Expressed Human TNFα and IL-6 from Human Peripheral Blood Mononuclear Cells Human buffy coats (human blood pack from the Blood Transfusion service) were layered on top of a HISTOPAQUE® 1.077 density gradient (Sigma, Cat No. 1077-1) and cells were centrifuged at 400×g for 40 minutes. No brake was applied when stopping the centrifuge. PBMC cells were then harvested from the interface. Cells were washed in PBS and pelleted at 300×g for 10 mins before the remaining red blood cells were lysed by resuspension in 20 ml of ice cold water for 15 s followed by the immediate addition of ice cold 1.6% NaCl. Cells were then pelleted at 1200 rpm for 5 mins and resuspended in 10 ml of 10% FBS/RPMI and 1% penicillin streptomycin. Cells were then diluted to $5 \times 10^6$/ml. 110 μl of cells were dispensed per well ($5.5 \times 10^5$/well) and cells allowed to settle for 1 hr at 37° C., 5% $CO_2$. The following reagents were added as single final concentration controls; PHA (5 μg/ml), LPS (25 μg/ml), GM-CSF (10 ng/ml) and isotype control (50 μg/ml). Antibody 6 was added to a final starting concentration of 50 μg/ml with a fivefold dilution series. Plates were then incubated for 72 hrs at 37° C., 5% $CO_2$. Supernatants were harvested after 72 hrs and the levels of TNFa and IL-6 were calculated using the following R&D ELISA kits (hTNF-a R&D Duoset ELISA development system DY210 and hIL-6 R&D Duoset ELISA development system DY206). ELISA were performed according to suppliers recommendations.

TABLE 1

Inhibition of GM-CSF induced proliferation of TF-1 cells by IgG4 non-germlined antibodies isolated from optimisation of 28G5.

| IgG4 | IC50 ± SEM (pM) |
|---|---|
| 2B7 | 1575 ± 490.5 |
| antibody 1 | 5.3 ± 0.33 |
| antibody 2 | 15.0 ± 4.71 |
| antibody 4 | 48.0 ± 8.33 |
| antibody 5 | 9.3 ± 5.39 |
| antibody 6 | 0.97 ± 0.033 |
| antibody 7 | 93.8 ± 24.6 |
| antibody 8 | 34.5 ± 2.63 |
| antibody 9 | 40.8 ± 7.15 |
| antibody 10 | 55.3 ± 3.73 |

TABLE 1-continued

Inhibition of GM-CSF induced proliferation of TF-1 cells by IgG4 non-germlined antibodies isolated from optimisation of 28G5.

| IgG4 | IC50 ± SEM (pM) |
|---|---|
| antibody 11 | 9.0 ± 1.0 |
| antibody 12 | 246.3 ± 19.8 |
| antibody 13 | 1106.0 ± 174.9 |
| antibody 14 | 16.3 ± 4.9 |
| antibody 15 | 163.8 ± 7.3 |
| antibody 16 | 12.8 ± 3.3 |
| antibody 17 | 14.3 ± 2.8 |
| antibody 18 | 13.3 ± 3.4 |
| antibody 19 | 23.8 ± 4.3 |
| antibody 20 | 9.8 ± 2.8 |

Proliferation of TF-1 cells was induced with a single concentration of GM-CSF in the presence of increasing concentrations of IgG4 antibodies. The incorporation of tritiated thymidine was measured and IC50 values for the antibodies were calculated. Data are representative of n ≧ 3. SEM (standard error of the mean) is shown.

TABLE 2

Kinetic analysis of anti-GM-CSFRα IgG4 non-germlined antibodies isolated during optimisation of 28G5.

| IgG4 | KD (nM) |
|---|---|
| antibody 1 | 0.264 |
| antibody 2 | 0.376 |
| antibody 4 | 4.07 |
| antibody 5 | 0.847 |
| antibody 6 | 0.139 |
| antibody 7 | 3.93 |
| antibody 8 | 0.552 |
| antibody 10 | 1.50 |
| antibody 12 | 3.02 |
| antibody 14 | 0.502 |
| antibody 15 | 1.03 |
| antibody 16 | 1.14 |
| antibody 17 | 0.193 |
| antibody 19 | 0.388 |
| antibody 20 | 0.127 |

IgG4 antibodies were immobilised to the surface of a protein-A coated chip and a series of purification-tagged GM-CSF Rα ECD dilutions were passed over the IgG4. Data was subject to fitting using the Langmuir 1:1 simultaneous $k_a$ $k_d$ with allowance for mass transport. Data for antibodies 9 and 11 were biphasic.

TABLE 3

Inhibition of GM-CSF induced shape change of human granulocytes by IgG4 non-germlined antibodies isolated during optimisation of 28G5. Human granulocytes were treated with a single concentration of GM-CSF in the presence of increasing concentrations of IgG4 antibody. The change in shape of the granulocytes was measured using flow cytometry and IC50 values for the antibodies were calculated.

| IgG4 | IC50 ± SD (pM) |
|---|---|
| 2B7 | 477 ± 491 |
| antibody 1 | 12.6 ± 8.0 |
| antibody 2 | 20.7 ± 11.0 |
| antibody 5 | 30.0 |
| antibody 6 | 13.3 ± 11.8 |
| antibody 9 | 44.0 |
| antibody 10 | 62.0 |
| antibody 11 | 90.0 |
| antibody 16 | 16.0 |
| antibody 20 | 7.8 |

TABLE 4

Inhibition of GM-CSF induced release of TNFα from monocytes. Human monocytes were treated with a single concentration of GM-CSF in the presence of increasing concentrations of IgG4 non-germlined antibody. The release of TNFα was measured by ELISA and the IC50 values for the antibodies were calculated.

| IgG4 | IC50 ± SD (pM) |
|---|---|
| antibody 1 | 78.8 ± 54.6 |
| antibody 2 | 103.3 ± 63.1 |
| antibody 5 | 67.0 |
| antibody 6 | 43.0 ± 19.7 |
| antibody 9 | 74.0 |
| antibody 10 | 139.0 |

TABLE 5

| KABAT RESIDUE | 28G5 | LEAD | Percentage occurrence of residue | | | | | | | |
|---|---|---|---|---|---|---|---|---|---|---|
| H95 | V | V | A | V | L | V | | | | |
| | | | 1.250 | 26.875 | 1.250 | 70.625 | | | | |
| H97 | S | S | S | | | | | | | |
| | | | 100.00 | | | | | | | |
| H99 | S | S | P | S | T | H | F | W | | |
| | | | 1.250 | 70.625 | 0.625 | 0.625 | 26.250 | 0.625 | | |
| H100B | A | T | A | P | S | T | H | V | | |
| | | | 63.125 | 2.500 | 2.500 | 28.75 | 0.625 | 2.500 | | |
| L90 | S | T | S | T | M | | | | | |
| | | | 90.000 | 9.375 | 0.625 | | | | | |
| L92 | D | E | S | T | D | Q | E | M | | |
| | | | 2.500 | 0.625 | 91.875 | 1.875 | 2.500 | 0.625 | | |
| L95A | S | S | G | P | S | T | N | D | Q | E |
| | | | 9.375 | 1.250 | 45.000 | 3.125 | 6.250 | 6.875 | 5.625 | 4.375 |
| L96 | S | S | A | P | S | T | I | L | M | V |
| | | | 1.250 | 26.250 | 43.750 | 1.250 | 17.500 | 0.625 | 1.250 | 8.125 |

| KABAT RESIDUE | Percentage occurrence of residue |
|---|---|
| H95 | |
| H97 | |
| H99 | |
| H100B | |

TABLE 5-continued

| | | | | | | | | | |
|---|---|---|---|---|---|---|---|---|---|
| L90 | | | | | | | | | |
| L92 | | | | | | | | | |
| L95A | R | H | K | I | L | M | V | F | Y |
| | 3.125 | 4.375 | 2.500 | 1.250 | 1.875 | 0.625 | 0.625 | 0.625 | 3.125 |
| L96 | | | | | | | | | |

KEY TO SEQUENCE LISTING

The Sequence Listing is submitted as an ASCII text file (entitled "Sequences") created on Dec. 28, 2011, ~100 KB, which is incorporated by reference herein. In the appended sequence listing, nucleic acid and amino acid ("PRT") sequences are listed for 20 antibody clones, comprising the parent clone and the 19 clones from the optimised panel. Antibodies are numbered Ab1 to Ab20. The parent clone is antibody 3, represented by SEQ ID NOS: 21, 22, 3, 4, 25, 26, 17, 8, 9, and 20 and SEQ ID NOS: 209-211.

The following list identifies by number the SEQ ID NOS in which sequences of the indicated molecules are shown: (nt=nucleotide sequence; aa=amino acid sequence

| | |
|---|---|
| 1 | Antibody 01 VH nt |
| 2 | Antibody 01 VH aa |
| 3 | Antibody 01 VH CDR1 aa |
| 4 | Antibody 01 VH CDR2 aa |
| 5 | Antibody 01 VH CDR3 aa |
| 6 | Antibody 01 VL nt |
| 7 | Antibody 01 VL aa |
| 8 | Antibody 01 VL CDR1 aa |
| 9 | Antibody 01 VL CDR2 aa |
| 10 | Antibody 01 VL CDR3 aa |
| 11 | Antibody 02 VH nt |
| 12 | Antibody 02 VH aa |
| 3 | Antibody 02 VH CDR1 aa |
| 4 | Antibody 02 VH CDR2 aa |
| 15 | Antibody 02 VH CDR3 aa |
| 16 | Antibody 02 VL nt |
| 17 | Antibody 02 VL aa |
| 8 | Antibody 02 VL CDR1 aa |
| 9 | Antibody 02 VL CDR2 aa |
| 20 | Antibody 02 VL CDR3 aa |
| 21 | Antibody 03 VH nt |
| 22 | Antibody 03 VH aa |
| 4 | Antibody 03 VH CDR1 aa |
| 24 | Antibody 03 VH CDR2 aa |
| 25 | Antibody 03 VH CDR3 aa |
| 26 | Antibody 03 VL nt |
| 17 | Antibody 03 VL aa |
| 8 | Antibody 03 VL CDR1 aa |
| 9 | Antibody 03 VL CDR2 aa |
| 20 | Antibody 03 VL CDR3 aa |
| 31 | Antibody 04 VH nt |
| 32 | Antibody 04 VH aa |
| 3 | Antibody 04 VH CDR1 aa |
| 4 | Antibody 04 VH CDR2 aa |
| 35 | Antibody 04 VH CDR3 aa |
| 36 | Antibody 04 VL nt |
| 17 | Antibody 04 VL aa |
| 8 | Antibody 04 VL CDR1 aa |
| 9 | Antibody 04 VL CDR2 aa |
| 20 | Antibody 04 VL CDR3 aa |
| 41 | Antibody 05 VH nt |
| 42 | Antibody 05 VH aa |
| 3 | Antibody 05 VH CDR1 aa |
| 4 | Antibody 05 VH CDR2 aa |
| 45 | Antibody 05 VH CDR3 aa |
| 36 | Antibody 05 VL nt |
| 17 | Antibody 05 VL aa |
| 8 | Antibody 05 VL CDR1 aa |
| 9 | Antibody 05 VL CDR2 aa |
| 20 | Antibody 05 VL CDR3 aa |
| 51 | Antibody 06 VH nt |
| 52 | Antibody 06 VH aa |
| 3 | Antibody 06 VH CDR1 aa |
| 4 | Antibody 06 VH CDR2 aa |
| 55 | Antibody 06 VH CDR3 aa |
| 56 | Antibody 06 VL nt |
| 57 | Antibody 06 VL aa |
| 8 | Antibody 06 VL CDR1 aa |
| 9 | Antibody 06 VL CDR2 aa |
| 60 | Antibody 06 VL CDR3 aa |
| 61 | Antibody 07 VH nt |
| 62 | Antibody 07 VH aa |
| 3 | Antibody 07 VH CDR1 aa |
| 4 | Antibody 07 VH CDR2 aa |
| 65 | Antibody 07 VH CDR3 aa |
| 36 | Antibody 07 VL nt |
| 17 | Antibody 07 VL aa |
| 8 | Antibody 07 VL CDR1 aa |
| 9 | Antibody 07 VL CDR2 aa |
| 20 | Antibody 07 VL CDR3 aa |
| 71 | Antibody 08 VH nt |
| 72 | Antibody 08 VH aa |
| 3 | Antibody 08 VH CDR1 aa |
| 4 | Antibody 08 VH CDR2 aa |
| 75 | Antibody 08 VH CDR3 aa |
| 36 | Antibody 08 VL nt |
| 17 | Antibody 08 VL aa |
| 8 | Antibody 08 VL CDR1 aa |
| 9 | Antibody 08 VL CDR2 aa |
| 20 | Antibody 08 VL CDR3 aa |
| 81 | Antibody 09 VH nt |
| 82 | Antibody 09 VH aa |
| 3 | Antibody 09 VH CDR1 aa |
| 4 | Antibody 09 VH CDR2 aa |
| 85 | Antibody 09 VH CDR3 aa |
| 36 | Antibody 09 VL nt |
| 17 | Antibody 09 VL aa |
| 8 | Antibody 09 VL CDR1 aa |
| 2 | Antibody 09 VL CDR2 aa |
| 20 | Antibody 09 VL CDR3 aa |
| 91 | Antibody 10 VH nt |
| 92 | Antibody 10 VH aa |
| 3 | Antibody 10 VH CDR1 aa |
| 4 | Antibody 10 VH CDR2 aa |
| 95 | Antibody 10 VH CDR3 aa |
| 36 | Antibody 10 VL nt |
| 17 | Antibody 10 VL aa |
| 8 | Antibody 10 VL CDR1 aa |
| 9 | Antibody 10 VL CDR2 aa |
| 20 | Antibody 10 VL CDR3 aa |
| 101 | Antibody 11 VH nt |
| 102 | Antibody 11 VH aa |
| 3 | Antibody 11 VH CDR1 aa |
| 4 | Antibody 11 VH CDR2 aa |
| 105 | Antibody 11 VH CDR3 aa |
| 106 | Antibody 11 VL nt |
| 107 | Antibody 11 VL aa |
| 8 | Antibody 11 VL CDR1 aa |
| 9 | Antibody 11 VL CDR2 aa |
| 20 | Antibody 11 VL CDR3 aa |
| 21 | Antibody 12 VH nt |
| 22 | Antibody 12 VH aa |
| 3 | Antibody 12 VH CDR1 aa |
| 4 | Antibody 12 VH CDR2 aa |
| 115 | Antibody 12 VH CDR3 aa |
| 116 | Antibody 12 VL nt |
| 117 | Antibody 12 VL aa |
| 8 | Antibody 12 VL CDR1 aa |
| 9 | Antibody 12 VL CDR2 aa |
| 120 | Antibody 12 VL CDR3 aa |

| | |
|---|---|
| 21 | Antibody 13 VH nt |
| 22 | Antibody 13 VH aa |
| 3 | Antibody 13 VH CDR1 aa |
| 4 | Antibody 13 VH CDR2 aa |
| 125 | Antibody 13 VH CDR3 aa |
| 126 | Antibody 13 VL nt |
| 127 | Antibody 13 VL aa |
| 8 | Antibody 13 VL CDR1 aa |
| 9 | Antibody 13 VL CDR2 aa |
| 130 | Antibody 13 VL CDR3 aa |
| 131 | Antibody 14 VH nt |
| 132 | Antibody 14 VH aa |
| 3 | Antibody 14 VH CDR1 aa |
| 4 | Antibody 14 VH CDR2 aa |
| 135 | Antibody 14 VH CDR3 aa |
| 136 | Antibody 14 VL nt |
| 137 | Antibody 14 VL aa |
| 8 | Antibody 14 VL CDR1 aa |
| 9 | Antibody 14 VL CDR2 aa |
| 140 | Antibody 14 VL CDR3 aa |
| 141 | Antibody 15 VH nt |
| 142 | Antibody 15 VH aa |
| 3 | Antibody 15 VH CDR1 aa |
| 4 | Antibody 15 VH CDR2 aa |
| 145 | Antibody 15 VH CDR3 aa |
| 146 | Antibody 15 VL nt |
| 147 | Antibody 15 VL aa |
| 8 | Antibody 15 VL CDR1 aa |
| 9 | Antibody 15 VL CDR2 aa |
| 150 | Antibody 15 VL CDR3 aa |
| 151 | Antibody 16 VH nt |
| 152 | Antibody 16 VH aa |
| 3 | Antibody 16 VH CDR1 aa |
| 4 | Antibody 16 VH CDR2 aa |
| 155 | Antibody 16 VH CDR3 aa |
| 156 | Antibody 16 VL nt |
| 157 | Antibody 16 VL aa |
| 8 | Antibody 16 VL CDR1 aa |
| 9 | Antibody 16 VL CDR2 aa |
| 160 | Antibody 16 VL CDR3 aa |
| 161 | Antibody 17 VH nt |
| 152 | Antibody 17 VH aa |
| 3 | Antibody 17 VH CDR1 aa |
| 4 | Antibody 17 VH CDR2 aa |
| 165 | Antibody 17 VH CDR3 aa |
| 166 | Antibody 17 VL nt |
| 167 | Antibody 17 VL aa |
| 8 | Antibody 17 VL CDR1 aa |
| 9 | Antibody 17 VL CDR2 aa |
| 170 | Antibody 17 VL CDR3 aa |
| 171 | Antibody 18 VH nt |
| 172 | Antibody 18 VH aa |
| 173 | Antibody 18 VH CDR1 aa |
| 4 | Antibody 18 VH CDR2 aa |
| 175 | Antibody 18 VH CDR3 aa |
| 176 | Antibody 18 VL nt |
| 177 | Antibody 18 VL aa |
| 8 | Antibody 18 VL CDR1 aa |
| 9 | Antibody 18 VL CDR2 aa |
| 180 | Antibody 18 VL CDR3 aa |
| 181 | Antibody 19 VH nt |
| 182 | Antibody 19 VH aa |
| 3 | Antibody 19 VH CDR1 aa |
| 4 | Antibody 19 VH CDR2 aa |
| 185 | Antibody 19 VH CDR3 aa |
| 186 | Antibody 19 VL nt |
| 187 | Antibody 19 VL aa |
| 8 | Antibody 19 VL CDR1 aa |
| 9 | Antibody 19 VL CDR2 aa |
| 190 | Antibody 19 VL CDR3 aa |
| 191 | Antibody 20 VH nt |
| 192 | Antibody 20 VH aa |
| 3 | Antibody 20 VH CDR1 aa |
| 4 | Antibody 20 VH CDR2 aa |
| 195 | Antibody 20 VH CDR3 aa |
| 196 | Antibody 20 VL nt |
| 197 | Antibody 20 VL aa |
| 8 | Antibody 20 VL CDR1 aa |
| 9 | Antibody 20 VL CDR2 aa |
| 200 | Antibody 20 VL CDR3 aa |
| 201 | GM-CSFRα linear residue sequence |
| 202 | Full length amino acid sequence of human GM-CSFRα |
| 203 | FLAG-tagged human GM-CSFRα extracellular domain |
| 204 | FLAG peptide |
| 205 | Amino acid sequence of human GM-CSFRα extracellular domain |
| 206 | Mature GM-CSFRα |
| 207 | Antibody 1 VL nt |
| 208 | Antibody 1 VL aa |
| 209 | Antibody 2 VL nt |
| 210 | Antibody 2 VL aa |
| 211 | Antibody 3 VL nt |
| 210 | Antibody 3 VL aa |
| 209 | Antibody 4 VL nt |
| 210 | Antibody 4 VL aa |
| 209 | Antibody 5 VL nt |
| 210 | Antibody 5 VL aa |
| 217 | Antibody 6 VL nt |
| 218 | Antibody 6 VL aa |
| 209 | Antibody 7 VL nt |
| 210 | Antibody 7 VL aa |
| 209 | Antibody 8 VL nt |
| 210 | Antibody 8 VL aa |
| 209 | Antibody 9 VL nt |
| 210 | Antibody 9 VL aa |
| 209 | Antibody 10 VL nt |
| 210 | Antibody 10 VL aa |
| 227 | Antibody 11 VL nt |
| 228 | Antibody 11 VL aa |
| 229 | Antibody 12 VL nt |
| 230 | Antibody 12 VL aa |
| 231 | Antibody 13 VL nt |
| 232 | Antibody 13 VL aa |
| 233 | Antibody 14 VL nt |
| 234 | Antibody 14 VL aa |
| 235 | Antibody 15 VL nt |
| 236 | Antibody 15 VL aa |
| 237 | Antibody 16 VL nt |
| 238 | Antibody 16 VL aa |
| 239 | Antibody 17 VL nt |
| 240 | Antibody 17 VL aa |
| 241 | Antibody 18 VL nt |
| 242 | Antibody 18 VL aa |
| 243 | Antibody 19 VL nt |
| 244 | Antibody 19 VL aa |
| 245 | Antibody 20 VL nt |
| 246 | Antibody 20 VL aa |
| 247 | Antibody 6 VH nt |
| 248 | Antibody 6 VH aa |
| 249 | Antibody 6 VL nt |
| 250 | Antibody 6 VL aa |
| 251 | VH FR1 aa |
| 252 | VH FR2 aa |
| 253 | VH FR3 aa |
| 254 | VH FR4 aa |
| 255 | VL FR1 aa |
| 256 | VL FR2 aa |
| 257 | VL FR3 aa |
| 258 | VL FR4 aa |

The VL domain nucleotide sequences of antibodies 1 to 20 do not include the gcg codon shown at the 3' end in SEQ ID NOS: 6, 16, 26, 36, 56, 106, 116, 126, 136, 146, 156, 166, 176, 186 and 196. Correspondingly, the VL domain amino acid sequences do not include the C-terminal Ala residue (residue 113) in SEQ ID NOS: 7, 17, 57, 107, 117, 127, 137, 147, 157, 167, 177, 187 and 197. The Ala113 residue and corresponding gcg codon were not expressed in Antibodies 1 to 20. A comparison of the written sequences with germline gene segments, especially JL2, indicates that the Ala residue and corresponding gcg codon do not form part of the VL domain.

The Gly residue at position 112 was present in the expressed scFv and IgG sequences. However, this residue is not present in human germline j segment sequences that form the framework 4 region of the VL domain, e.g. JL2. The Gly residue is not considered a part of the VL domain.

To express the light chain of the IgG, a nucleotide sequence encoding the antibody light chain was provided, comprising a first exon encoding the VL domain, a second exon encoding the CL domain, and an intron separating the first exon and the second exon. Under normal circumstances, the intron is spliced out by cellular mRNA processing machinery, joining the 3' end of the first exon to the 5' end of the second exon. Thus, when DNA having the said nucleotide sequence was expressed as RNA, the first and second exons were spliced together. Translation of the spliced RNA produces a polypeptide comprising the VL and the CL domain. After splicing, the Gly at position 112 is encoded by the last base (g) of the VL domain framework 4 sequence and the first two bases (gt) of the CL domain.

The VL domain sequences of Antibodies 1 to 20 are SEQ ID NOS: 186 to 246 as indicated above. The VL domain nucleotide sequences end with cta as the final codon, and Leu is the final amino acid residue in the corresponding VL domain amino acid sequences.

Non-germlined VH and VL domain sequences of Antibody 6 are shown in SEQ ID NOS: 247-250, in addition to the germlined VH and VL domain sequences shown in SEQ ID NOS: 51, 52, 56, 57, 216 and 217.

REFERENCES

All documents mentioned anywhere in this disclosure are incorporated herein by reference.
1 Haman et al., *Journal of Biological Chemistry* 274(48): 34155-34163 1999
2 Nicola N A; Wycherley A; Boyd A W; Layton J E; Cary D; Metcalf D Blood, 82(6) p 1724-31 (1993)
3 Plückthun, A. Bio/Technology 9: 545-551 (1991)
4 Chadd H E and Chamow S M (2001) Current Opinion in Biotechnology 12: 188-194
5 Andersen D C and Krummen L (2002) Current Opinion in Biotechnology 13: 117
6 Larrick J W and Thomas D W (2001) Current Opinion in Biotechnology 12:411-418
7 Sambrook and Russell, Molecular Cloning: a Laboratory Manual: 3rd edition, 2001, Cold Spring Harbor Laboratory Press
8 Ausubel et al. eds., *Short Protocols in Molecular Biology: A Compendium of Methods from Current Protocols in Molecular Biology*, John Wiley & Sons, 4$^{th}$ edition 1999
9 Wold, et al. Multivariate data analysis in chemistry. Chemometrics-Mathematics and Statistics in Chemistry (Ed.: B. Kowalski), D. Reidel Publishing Company, Dordrecht, Holland, 1984 (ISBN 90-277-1846-6)
10 Norman et al. Applied Regression Analysis. Wiley-Interscience; 3$^{rd}$ edition (April 1998) ISBN: 0471170828
11 Kandel, Abraham & Backer, Eric. Computer-Assisted Reasoning in Cluster Analysis. Prentice Hall PTR, (May 11, 1995), ISBN:
12 Krzanowski, Wojtek. Principles of Multivariate Analysis: A User's Perspective (Oxford Statistical Science Series, No 22 (Paper)). Oxford University Press; (December 2000), ISBN: 0198507089
13 Witten, Ian H. & Frank, Eibe. Data Mining: Practical Machine Learning Tools and Techniques with Java Implementations. Morgan Kaufmann; (Oct. 11, 1999), ISBN: 1558605525
14 Denison David G. T. (Editor), Christopher C. Holmes, Bani K.
15 Ghose, Arup K. & Viswanadhan, Vellarkad N. Combinatorial Library Design and Evaluation Principles, Software, Tools, and Applications in Drug Discovery. ISBN: 0-8247-0487-8
16 Chothia C. et al. Journal Molecular Biology (1992) 227, 799-817
17 Al-Lazikani, et al. Journal Molecular Biology (1997) 273 (4), 927-948
18 Chothia, et al. Science, 223, 755-758 (1986)
19 Whitelegg, N. R. u. and Rees, A. R (2000). Prot. Eng., 12, 815-824
20 Guex, N. and Peitsch, M. C. Electrophoresis (1997) 18, 2714-2723
21 Voet & Voet, Biochemistry, 2nd Edition, (Wiley) 1995.
22 Marks et al *Bio/Technology*, 1992, 10:779-783
23 Kay, B. K., Winter, J., and McCafferty, J. (1996) Phage Display of Peptides and Proteins: A Laboratory Manual, San Diego: Academic Press.
24 Stemmer, Nature, 1994, 370:389-391
25 Gram et al., 1992, *Proc. Natl. Acad. Sci., USA,* 89:3576-3580
26 Barbas et al., 1994, *Proc. Natl. Acad. Sci., USA,* 91:3809-3813
27 Schier et al., 1996, J. Mol. Biol. 263:551-567
28 Ledermann J. A. et al. (1991) Int. J. Cancer 47: 659-664
29 Bagshawe K. D. et al. (1991) Antibody, Immunoconjugates and Radiopharmaceuticals 4: 915-922
30 Robinson, J. R. ed., Sustained and Controlled Release Drug Delivery Systems, Marcel Dekker, Inc., New York, 1978
31 Ritz, S. A., M. J. Cundall, et al. (2002). Am J Respir Cell Mol Biol 27(4): 428-35.
32 Ritz, S. A., M. R. Stampfli, et al. (2002). Trends Immunol 23(8): 396-402.
33 WOOLLEY, K. L., et al. (1995). *Am J Respir Crit. Care Med,* 151, 1915-24.
34 Kotsimbos, A. T., M. Humbert, et al. (1997). J Allergy Clin Immunol 99(5): 666-72.
35 Yamashita N. et al., Cell. Immunol 2002 oct; 219(2); 92-97
36 Ohta K., et al. J Allergy Clin Immunol. 1999 November; 104(5): 1024-30
37 Stampfli, M. R., R. E. Wiley, et al. (1998). J Clin Invest 102(9): 1704-14.
38 Cates, E. C., B. U. Gajewska, et al. (2003). J Allergy Clin Immunol 111(5): 1076-86.
39 CAMPBELL, I. K., et al. (1997) *Annal Res Dis,* 56, 364-368.
40 BISCHOF, R. J., D. ZAFIROPOULOS, J. A. HAMILTON AND I. K. CAMPBELL (2000) *Clin Exp Immunol,* 119, 361-367.
41 Campbell, I. K., M. J. Rich, et al. (1998). J Immunol 161(7): 3639-44.
42 Hamilton, J. A. (2002). Trends Immunol 23(8): 403-8.
43 YANG, Y. H. AND J. A. HAMILTON (2001) *Arthritis Rheumatol,* 44, 111-119
44 Cook, A. D., E. L. Braine, et al. (2001). Arthritis Res 3(5): 293-8.
45 Field, M. and L. Clinton (1993). The Lancet 342: 1244.
46 Firestein G S, Alvaro-Gracia J M, Maki R. 1990 J. Immunol. may 1; 144(9): 3347-53
47 Leizer T, et al. 1990 Blood 1990 Nov. 15; 76(10): 1989-96
48 Fiehn C, et al., Z Rheumatol 1992 May-June; 51 (3): 1221-126
49 de Vries, E. G., et al. (1991) *Lancet,* 338, 517-518.
50 Hazenberg B P, et al. Blood 1989 December; 74(8): 2769-70
51 Barnes and Hansel (2004). Lancet, 364:985-96.
52 Barnes, P. J. (2000). Chest, 117:10 S-14S 53 McManus, T. E., et al (2005) American Thoracic Society Meeting, May 2005.
54 Vlahos, R., et al. (2005). "GM-CSF is a key pathogenic mediator in experimental COPD." European Respiratory Society Meeting, September 2005
55 McQualter J L, et al. (2001) J Exp Med. 194: 873-82
56 Bagby G C Jr, et al. 1988 J Clin Invest. 4: 1430-6.
57 Estrov Z, et al. (1986) Cancer Res. 46: 6456-61.
58 Barak Y, et al. 1981 Am J. Hematol. 10: 269-75.
59 Gualtieri R J, et al. 1988 Exp Hematol. 16:613-9.
60 Suda T, et al. 1982 Leuk Res. 6: 43-53.
61 Gualtieri R J, et al. 1989 Blood. 74: 2360-7
62 Largaespada D A, et al. (1996) *Nat. Genet.* 12: 137-43
63 Iversen, P. O., et al. (1997). Blood 90(12): 4910-7.
64 Wang et al., 1994 Exp mol Pathol
65 Plenz et al., Art. Thrombosis and Vascular biology 1997
66 Takashi et al., 1996 Circulation 93, 1185-1193
67 Biwa T et al., JBC 1998 273: 28305-28313
68 Makheja et al., Atherosclerosis 1989, 76 155-661
69 Naito et al., 1992 J Nutri sci Vitamin 38: 255-264
70 Hayashi et al., Atherosclerosis 1991 91: 107-116
71 Villa et al 1994 J Clin Invest 93: 1243
72 Van Put D J et al., 1995 Eur J Pharmacol 294: 753-761
73 Voisard et al., 1994 Int J Cardiol 43: 257-267
74 Yamada et al., 1993: Artery 20: 253-267
75 Sakai et al., 1999 Arterioscler Thromb vasc biol 19: 1726-1733
76 Gearing, et al. EMBO J. 8 (12): 3667-3676 (1989)
77 Crosier, K. et al. *PNAS* 88:7744-7748 1991
78 Raines, M. et al. *PNAS* 88:8203-8207 1991
79 Wess, L. In: BioCentury, The Bernstein Report on Bio-Business, 12(42), A1-A7, 2004
80 Haan & Maggos (2004) BioCentury, 12(5): A1-A6
81 Koide et al. (1998) Journal of Molecular Biology, 284: 1141-1151.
82 Nygren et al. (1997) Current Opinion in Structural Biology, 7: 463-469
83 Kontermann, R & Dubel, S, *Antibody Engineering*, Springer-Verlag New York, LLC; 2001, ISBN: 3540413545
84 Mendez, M. et al. (1997) Nature Genet, 15(2): 146-156
85 Knappik et al. J. Mol. Biol. (2000) 296, 57-86
86 Krebs et al. Journal of Immunological Methods 254 2001 67-84
87 Ward, E. S. et al., Nature 341, 544-546 (1989)
88 McCafferty et al (1990) Nature, 348, 552-554
89 Holt et al (2003) Trends in Biotechnology 21, 484-490
90 Bird et al, Science, 242, 423-426, 1988;
91 Huston et al, PNAS USA, 85, 5879-5883, 1988
91 Holliger, P. et al, Proc. Natl. Acad. Sci. USA 90 6444-6448, 1993
93 Reiter, Y. et al, Nature Biotech, 14, 1239-1245, 1996
94 Hu, S. et al, Cancer Res., 56, 3055-3061, 1996.
95 Holliger, P. and Winter G. Current Opinion Biotechnol 4, 446-449 1993
96 Ridgeway, J. B. B. et al, Protein Eng., 9, 616-621, 1996
97 Ann N Y Acad. Sci. 1971 Dec. 31; 190:382-93.
98 Kabat, E. A. et al, Sequences of Proteins of Immunological Interest. 4th Edition. US Department of Health and Human Services. 1987
99 Kabat, E. A. et al. (1991) Sequences of Proteins of Immunological Interest, 5th Edition. US Department of Health and Human Services, Public Service, NIH, Washington.
100 Persic et al 1997 Gene 187; 9-18
101 Hanes J et al (2000) Methods in Enzymology, Vol 328:24.
102 Vaughan T J et al (1996) Nature Biotechnology Vol 14:309
103 Slootstra-J W; Puijk-W C; Ligtvoet-G J; Langeveld-J P; Meloen-R H (1996). *Mol-Divers.* 1: 87-96
104 WO01/66754 Cambridge Antibody Technology Limited; Vaughan; Wilton; Smith; Main
105 P. K. Smith, et al., *Anal. Biochem.* 150 (1985), pp. 76-85
106 S. Mizushima and S, Nagata *Nucleic Acids Research*, Vol 18; No 17 1990 pp 5322
107 Clin Haematol. 1979 June; 8(2):263-85. Metcalf D.
108 Nishijima, I., T. Nakahata, et al. (1997). Blood 90(3): 1031-8.

The invention claimed is:

1. An isolated antibody molecule for human GM-CSFRα, which inhibits binding of GM-CSF to GM-CSFRα, and which comprises a VH domain with the VH domain amino acid sequence shown in SEQ ID NO: 52 and a VL domain with the VL domain amino acid sequence shown in SEQ ID NO: 218.

2. The isolated antibody molecule according to claim 1, wherein the antibody molecule is an IgG4.

3. An isolated antibody molecule, wherein the antibody molecule comprises an antibody VH domain and an antibody VL domain, the antibody VH domain comprising heavy chain complementarity determining regions (CDRs) HCDR1, HCDR2 and HCDR3 and the VL domain comprising light chain CDRs LCDR1, LCDR2 and LCDR3, wherein the amino acid sequences of the CDRs are:
HCDR1 SEQ ID NO: 3
HCDR2 SEQ ID NO: 4
HCDR3 SEQ ID NO: 55
LCDR1 SEQ ID NO: 8
LCDR2 SEQ ID NO: 9, and
LCDR3 SEQ ID NO: 60.

4. An antibody molecule according to claim 3, which is a human or humanised antibody molecule.

5. An antibody molecule according to claim 3, comprising antibody VH domain amino acid sequence SEQ ID NO: 52.

6. An antibody molecule according to claim 3, comprising antibody VL domain amino acid sequence SEQ ID NO: 218.

7. An antibody molecule according to claim 3, which is an IgG4.

8. An antibody molecule according to claim 7, wherein the antibody molecule is a human IgG4 antibody molecule comprising VH domain amino acid sequence SEQ ID NO: 52 and VL domain amino acid sequence SEQ ID NO: 218.

9. An isolated antibody molecule for human GM-CSFRα, which inhibits binding of GM-CSF to GM-CSFRα, and which comprises:
a VH domain with the VH domain amino acid sequence shown in SEQ ID NO: 52, or comprises that VH domain with one or two conservative amino acid substitutions, and
a VL domain with the VL domain amino acid sequence shown in SEQ ID NO: 218, or comprises that VL domain with one or two conservative amino acid substitutions.

10. A composition comprising an antibody molecule according to any of claim 1, 2, 3 or 4-9 and a pharmaceutically acceptable excipient.

* * * * *

UNITED STATES PATENT AND TRADEMARK OFFICE
CERTIFICATE OF CORRECTION

PATENT NO. : 8,263,075 B2  
APPLICATION NO. : 11/692008  
DATED : September 11, 2012  
INVENTOR(S) : Emma Suzanne Cohen et al.

Page 1 of 1

It is certified that error appears in the above-identified patent and that said Letters Patent is hereby corrected as shown below:

<u>On the title page, item;</u>

(73) Assignee: should *also* include --Zenyth Operations Pty. Ltd., Parkville (AU)--.

<u>In the Specification:</u>

Column 22, line 34, "debri" should read --debris--.

Column 22, line 64, "shown that" should read --show that--.

Column 23, line 25, "receptor a has" should read --receptor α has--.

Column 31, line 15, "to same" should read --to the same--.

Column 41, lines 39-40, "huGM-CS-FRαβ" should read --huGM-CSFRαβ--.

Column 45, line 43, "4     Antibody 03     VH CDR1 aa" should read

--3     Antibody 03     VH CDR1 aa --.

Column 45, line 44, "24     Antibody 03     VH CDR2 aa" should read

--4     Antibody 03     VH CDR2 aa--.

Signed and Sealed this
Twenty-sixth Day of November, 2013

Margaret A. Focarino
*Commissioner for Patents of the United States Patent and Trademark Office*

SEQUENCE LISTING

```
<160> NUMBER OF SEQ ID NOS: 258

<210> SEQ ID NO 1
<211> LENGTH: 360
<212> TYPE: DNA
<213> ORGANISM: Homo sapiens
<220> FEATURE:
<223> OTHER INFORMATION: Ab1

<400> SEQUENCE: 1
caggtgcagc tggtgcaatc tggggctgag gtgaagaagc ctggggcctc agtgaaggtc      60
tcatgtaaag tttccggata caccctcact gaactgtcca tccactgggt gcgacaggct     120
cccggaaaag gacttgagtg gatgggagga tttgatcctg aagagaatga aatagtctac     180
gcacagaggt tccagggcag agtcaccatg accgaggaca catctacaga cacggcctac     240
atggaactga gcagcctgag atccgaggac acggccgttt attattgtgc aatagtgggg     300
tctttcagtg gcatcgccta tcgcccctgg ggccaaggga caatggtcac cgtctcctca     360

<210> SEQ ID NO 2
<211> LENGTH: 120
<212> TYPE: PRT
<213> ORGANISM: Homo sapiens
```

```
<220> FEATURE:
<223> OTHER INFORMATION: Ab1

<400> SEQUENCE: 2

Gln Val Gln Leu Val Gln Ser Gly Ala Glu Val Lys Lys Pro Gly Ala
                 5                  10                  15

Ser Val Lys Val Ser Cys Lys Val Ser Gly Tyr Thr Leu Thr Glu Leu
             20                  25                  30

Ser Ile His Trp Val Arg Gln Ala Pro Gly Lys Gly Leu Glu Trp Met
         35                  40                  45

Gly Gly Phe Asp Pro Glu Glu Asn Glu Ile Val Tyr Ala Gln Arg Phe
     50                  55                  60

Gln Gly Arg Val Thr Met Thr Glu Asp Thr Ser Thr Asp Thr Ala Tyr
 65                  70                  75                  80

Met Glu Leu Ser Ser Leu Arg Ser Glu Asp Thr Ala Val Tyr Tyr Cys
                 85                  90                  95

Ala Ile Val Gly Ser Phe Ser Gly Ile Ala Tyr Arg Pro Trp Gly Gln
            100                 105                 110

Gly Thr Met Val Thr Val Ser Ser
        115                 120

<210> SEQ ID NO 3
<211> LENGTH: 5
<212> TYPE: PRT
<213> ORGANISM: Homo sapiens
<220> FEATURE:
<223> OTHER INFORMATION: Ab1

<400> SEQUENCE: 3

Glu Leu Ser Ile His
                 5

<210> SEQ ID NO 4
<211> LENGTH: 17
<212> TYPE: PRT
<213> ORGANISM: Homo sapiens
<220> FEATURE:
<223> OTHER INFORMATION: Ab1

<400> SEQUENCE: 4

Gly Phe Asp Pro Glu Glu Asn Glu Ile Val Tyr Ala Gln Arg Phe Gln
                 5                  10                  15

Gly

<210> SEQ ID NO 5
<211> LENGTH: 11
<212> TYPE: PRT
<213> ORGANISM: Homo sapiens
<220> FEATURE:
<223> OTHER INFORMATION: Ab1

<400> SEQUENCE: 5

Val Gly Ser Phe Ser Gly Ile Ala Tyr Arg Pro
                 5                  10

<210> SEQ ID NO 6
<211> LENGTH: 339
<212> TYPE: DNA
<213> ORGANISM: Homo sapiens
<220> FEATURE:
<223> OTHER INFORMATION: Ab1

<400> SEQUENCE: 6
```

```
cagtctgtgc tgactcagcc gccctcagtg tctggggccc cagggcagag ggtcaccatc    60
tcctgtactg ggagcggctc caacatcggg gcaccttatg atgtaagctg gtaccagcag   120
cttccaggaa cagcccccaa actcctcatc tatcataaca acaagcggcc ctcaggggtc   180
cctgaccgat tctctggctc caagtctggc acctcagcct ccctggccat cactgggctc   240
caggctgagg atgaggctga ttattactgc cagtcctatg acagcagctc gatcagcacg   300
attttcggcg gagggaccaa gctcaccgtc ctaggtgcg                          339
```

```
<210> SEQ ID NO 7
<211> LENGTH: 113
<212> TYPE: PRT
<213> ORGANISM: Homo sapiens
<220> FEATURE:
<223> OTHER INFORMATION: Ab1

<400> SEQUENCE: 7

Gln Ser Val Leu Thr Gln Pro Pro Ser Val Ser Gly Ala Pro Gly Gln
 1               5                  10                  15

Arg Val Thr Ile Ser Cys Thr Gly Ser Gly Ser Asn Ile Gly Ala Pro
            20                  25                  30

Tyr Asp Val Ser Trp Tyr Gln Gln Leu Pro Gly Thr Ala Pro Lys Leu
        35                  40                  45

Leu Ile Tyr His Asn Asn Lys Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95

Ser Ile Ser Thr Ile Phe Gly Gly Gly Thr Lys Leu Thr Val Leu Gly
            100                 105                 110

Ala
```

```
<210> SEQ ID NO 8
<211> LENGTH: 14
<212> TYPE: PRT
<213> ORGANISM: Homo sapiens
<220> FEATURE:
<223> OTHER INFORMATION: Ab1

<400> SEQUENCE: 8

Thr Gly Ser Gly Ser Asn Ile Gly Ala Pro Tyr Asp Val Ser
 1               5                  10
```

```
<210> SEQ ID NO 9
<211> LENGTH: 7
<212> TYPE: PRT
<213> ORGANISM: Homo sapiens
<220> FEATURE:
<223> OTHER INFORMATION: Ab1

<400> SEQUENCE: 9

His Asn Asn Lys Arg Pro Ser
 1               5
```

```
<210> SEQ ID NO 10
<211> LENGTH: 11
<212> TYPE: PRT
<213> ORGANISM: Homo sapiens
<220> FEATURE:
<223> OTHER INFORMATION: Ab1

<400> SEQUENCE: 10
```

Gln Ser Tyr Asp Ser Ser Ser Ile Ser Thr Ile
            5                   10

<210> SEQ ID NO 11
<211> LENGTH: 360
<212> TYPE: DNA
<213> ORGANISM: Homo sapiens
<220> FEATURE:
<223> OTHER INFORMATION: Ab2

<400> SEQUENCE: 11
caggtgcagc tggtgcaatc tggggctgag gtgaagaagc ctggggcctc agtgaaggtc      60
tcatgtaaaa tttccggaca cagcctcagt gaactgtcca tccactgggt gcgacagact     120
cccacaaaag gatttgagtg gatgggagga tttgatcctg aagagaatga aatagtctac     180
gcacagaggt tccagggcag agtcaccatg accgaggaca catctataga cacggcctac     240
ctgaccctga gcagcctgag atccgacgac acggccgttt attattgttc aatagtgggg     300
tctttcagtg gccccgccct gcgcccctgg ggcaaaggga caatggtcac cgtctcgagt     360

<210> SEQ ID NO 12
<211> LENGTH: 120
<212> TYPE: PRT
<213> ORGANISM: Homo sapiens
<220> FEATURE:
<223> OTHER INFORMATION: Ab2

<400> SEQUENCE: 12

Gln Val Gln Leu Val Gln Ser Gly Ala Glu Val Lys Lys Pro Gly Ala
                5                   10                  15

Ser Val Lys Val Ser Cys Lys Ile Ser Gly His Ser Leu Ser Glu Leu
            20                  25                  30

Ser Ile His Trp Val Arg Gln Thr Pro Thr Lys Gly Phe Glu Trp Met
        35                  40                  45

Gly Gly Phe Asp Pro Glu Glu Asn Glu Ile Val Tyr Ala Gln Arg Phe
    50                  55                  60

Gln Gly Arg Val Thr Met Thr Glu Asp Thr Ser Ile Asp Thr Ala Tyr
65                  70                  75                  80

Leu Thr Leu Ser Ser Leu Arg Ser Asp Asp Thr Ala Val Tyr Tyr Cys
                85                  90                  95

Ser Ile Val Gly Ser Phe Ser Gly Pro Ala Leu Arg Pro Trp Gly Lys
            100                 105                 110

Gly Thr Met Val Thr Val Ser Ser
        115                 120

<210> SEQ ID NO 13

<400> SEQUENCE: 13

000

<210> SEQ ID NO 14

<400> SEQUENCE: 14

000

<210> SEQ ID NO 15
<211> LENGTH: 11
<212> TYPE: PRT
<213> ORGANISM: Homo sapiens
<220> FEATURE:

<223> OTHER INFORMATION: Ab2

<400> SEQUENCE: 15

Val Gly Ser Phe Ser Gly Pro Ala Leu Arg Pro
                5                   10

<210> SEQ ID NO 16
<211> LENGTH: 339
<212> TYPE: DNA
<213> ORGANISM: Homo sapiens
<220> FEATURE:
<223> OTHER INFORMATION: Ab2

<400> SEQUENCE: 16
caggctgtgc tgactcagcc gtcctcagtg tctggggccc cagggcagag ggtcaccatc      60
tcctgtactg ggagcggctc caacatcggg gcaccttatg atgtaagctg gtaccagcag     120
cttccaggaa cagcccccaa actcctcatc tatcataaca acaagcggcc ctcaggggtc     180
cctgaccgat tctctgcctc caagtctggc acctcagcct ccctggccat cactgggctc     240
caggctgacg atgaggctga ttattactgc cagtcctatg acagcagcct gagtggttcg     300
gttttcggcg agggaccaa ggtcaccgtc ctaggtgcc                             339

<210> SEQ ID NO 17
<211> LENGTH: 113
<212> TYPE: PRT
<213> ORGANISM: Homo sapiens
<220> FEATURE:
<223> OTHER INFORMATION: Ab2

<400> SEQUENCE: 17

Gln Ala Val Leu Thr Gln Pro Ser Ser Val Ser Gly Ala Pro Gly Gln
                5                   10                  15

Arg Val Thr Ile Ser Cys Thr Gly Ser Gly Ser Asn Ile Gly Ala Pro
            20                  25                  30

Tyr Asp Val Ser Trp Tyr Gln Gln Leu Pro Gly Thr Ala Pro Lys Leu
        35                  40                  45

Leu Ile Tyr His Asn Asn Lys Arg Pro Ser Gly Val Pro Asp Arg Phe
    50                  55                  60

Ser Ala Ser Lys Ser Gly Thr Ser Ala Ser Leu Ala Ile Thr Gly Leu
65                  70                  75                  80

Gln Ala Asp Asp Glu Ala Asp Tyr Tyr Cys Gln Ser Tyr Asp Ser Ser
                85                  90                  95

Leu Ser Gly Ser Val Phe Gly Gly Gly Thr Lys Val Thr Val Leu Gly
            100                 105                 110

Ala

<210> SEQ ID NO 18

<400> SEQUENCE: 18

000

<210> SEQ ID NO 19

<400> SEQUENCE: 19

000

<210> SEQ ID NO 20
<211> LENGTH: 11
<212> TYPE: PRT

<213> ORGANISM: Homo sapiens
<220> FEATURE:
<223> OTHER INFORMATION: Ab2

<400> SEQUENCE: 20

Gln Ser Tyr Asp Ser Ser Leu Ser Gly Ser Val
                5                   10

<210> SEQ ID NO 21
<211> LENGTH: 360
<212> TYPE: DNA
<213> ORGANISM: Homo sapiens
<220> FEATURE:
<223> OTHER INFORMATION: Ab3

<400> SEQUENCE: 21
caggtgcagc tggtgcaatc tgggctgag gtgaagaagc ctggggcctc agtgaaggtc      60
tcatgtaaaa tttccggaca cagcctcagt gaactgtcca tccactgggt gcgacagact     120
cccacaaaag gatttgagtg gatgggagga tttgatcctg aagagaatga aatagtctac     180
gcacagaggt tccagggcag agtcaccatg accgaggaca tcctataga cacggcctac      240 ctgaccctga gcagcctgag atccgacgac acggccgttt attattgttc aatagtgggg     300
tctttcagtg gctgggcctt tgactactgg ggcaaaggga caatggtcac cgtctcgagt     360

<210> SEQ ID NO 22
<211> LENGTH: 120
<212> TYPE: PRT
<213> ORGANISM: Homo sapiens
<220> FEATURE:
<223> OTHER INFORMATION: Ab3

<400> SEQUENCE: 22

Gln Val Gln Leu Val Gln Ser Gly Ala Glu Val Lys Lys Pro Gly Ala
                5                   10                  15

Ser Val Lys Val Ser Cys Lys Ile Ser Gly His Ser Leu Ser Glu Leu
            20                  25                  30

Ser Ile His Trp Val Arg Gln Thr Pro Thr Lys Gly Phe Glu Trp Met
        35                  40                  45

Gly Gly Phe Asp Pro Glu Glu Asn Glu Ile Val Tyr Ala Gln Arg Phe
    50                  55                  60

Gln Gly Arg Val Thr Met Thr Glu Asp Thr Ser Ile Asp Thr Ala Tyr
65                  70                  75                  80

Leu Thr Leu Ser Ser Leu Arg Ser Asp Asp Thr Ala Val Tyr Tyr Cys
                85                  90                  95

Ser Ile Val Gly Ser Phe Ser Gly Trp Ala Phe Asp Tyr Trp Gly Lys
            100                 105                 110

Gly Thr Met Val Thr Val Ser Ser
        115                 120

<210> SEQ ID NO 23

<400> SEQUENCE: 23

000

<210> SEQ ID NO 24

<400> SEQUENCE: 24

000

```
<210> SEQ ID NO 25
<211> LENGTH: 11
<212> TYPE: PRT
<213> ORGANISM: Homo sapiens
<220> FEATURE:
<223> OTHER INFORMATION: Ab3

<400> SEQUENCE: 25

Val Gly Ser Phe Ser Gly Trp Ala Phe Asp Tyr
            5                   10

<210> SEQ ID NO 26
<211> LENGTH: 339
<212> TYPE: DNA
<213> ORGANISM: Homo sapiens
<220> FEATURE:
<223> OTHER INFORMATION: Ab3

<400> SEQUENCE: 26
caggctgtgc tgactcagcc gtcctcagtg tctggggccc cagggcagag ggtcaccatc      60
tcctgtactg ggagcggctc aaacatcggg gcaccttatg atgtaagctg gtaccagcag     120
cttccaggaa cagcccccaa actcctcatc tatcataaca acaagcggcc ctcaggggtc     180
cctgaccgat tctctgcctc caagtctggc acctcagcct ccctggccat cactgggctc     240
caggctgacg atgaggctga ttattactgc cagtcctatg acagcagcct gagtggttcg     300
gttttcgggg gagggaccaa ggtcaccgtc ctaggtgcg                            339

<210> SEQ ID NO 27

<400> SEQUENCE: 27

000

<210> SEQ ID NO 28

<400> SEQUENCE: 28

000

<210> SEQ ID NO 29

<400> SEQUENCE: 29

000

<210> SEQ ID NO 30

<400> SEQUENCE: 30

000

<210> SEQ ID NO 31
<211> LENGTH: 360
<212> TYPE: DNA
<213> ORGANISM: Homo sapiens
<220> FEATURE:
<223> OTHER INFORMATION: Ab4

<400> SEQUENCE: 31
caggtgcagc tggtgcaatc tggggctgag gtgaagaagc ctggggcctc agtgaaggtc      60
tcatgtaaaa tttccggaca cagcctcagt gaactgtcca tccactgggt gcgacagact     120
cccacaaaag gatttgagtg gatgggagga tttgatcctg aagagaatga aatagtctac     180
gcacagaggt tccagggcag agtcaccatg accgaggaca catctataga cacggcctac     240
```

```
ctgaccctga gcagcctgag atccgacgac acggccgttt attattgtgc aatagtgggg      300
tctttcagtc ccccgaccta cgggtactgg ggcaaaggga caatggtcac cgtctcgagt      360
```

<210> SEQ ID NO 32
<211> LENGTH: 120
<212> TYPE: PRT
<213> ORGANISM: Homo sapiens
<220> FEATURE:
<223> OTHER INFORMATION: Ab4

<400> SEQUENCE: 32

Gln Val Gln Leu Val Gln Ser Gly Ala Glu Val Lys Lys Pro Gly Ala
1               5                   10                  15
Ser Val Lys Val Ser Cys Lys Ile Ser Gly His Ser Leu Ser Glu Leu
            20                  25                  30
Ser Ile His Trp Val Arg Gln Thr Pro Thr Lys Gly Phe Glu Trp Met
        35                  40                  45
Gly Gly Phe Asp Pro Glu Glu Asn Glu Ile Val Tyr Ala Gln Arg Phe
    50                  55                  60
Gln Gly Arg Val Thr Met Thr Glu Asp Thr Ser Ile Asp Thr Ala Tyr
65                  70                  75                  80
Leu Thr Leu Ser Ser Leu Arg Ser Asp Asp Thr Ala Val Tyr Tyr Cys
                85                  90                  95
Ala Ile Val Gly Ser Phe Ser Pro Pro Thr Tyr Gly Tyr Trp Gly Lys
            100                 105                 110
Gly Thr Met Val Thr Val Ser Ser
        115                 120

<210> SEQ ID NO 33

<400> SEQUENCE: 33

000

<210> SEQ ID NO 34

<400> SEQUENCE: 34

000

<210> SEQ ID NO 35
<211> LENGTH: 11
<212> TYPE: PRT
<213> ORGANISM: Homo sapiens
<220> FEATURE:
<223> OTHER INFORMATION: Ab4

<400> SEQUENCE: 35

Val Gly Ser Phe Ser Pro Pro Thr Tyr Gly Tyr
1               5                   10

<210> SEQ ID NO 36
<211> LENGTH: 339
<212> TYPE: DNA
<213> ORGANISM: Homo sapiens
<220> FEATURE:
<223> OTHER INFORMATION: Ab4

<400> SEQUENCE: 36

```
caggctgtgc tgactcagcc gtcctcagtg tctggggccc cagggcagag ggtcaccatc       60
tcctgtactg ggagcggctc caacatcggg gcacccttatg atgtaagctg gtaccagcag     120
cttccaggaa cagcccccaa actcctcatc tatcataaca acaagcggcc ctcagggggtc     180
```
cctgaccgat tctctgcctc caagtctggc acctcagcct ccctggccat cactgggctc    240
caggctgacg atgaggctga ttattactgc cagtcctatg acagcagcct gagtggttcg    300
gttttcggcg agggaccaa ggtcaccgtc ctaggtgcg                            339

<210> SEQ ID NO 37
<400> SEQUENCE: 37

000

<210> SEQ ID NO 38
<400> SEQUENCE: 38

000

<210> SEQ ID NO 39
<400> SEQUENCE: 39

000

<210> SEQ ID NO 40
<400> SEQUENCE: 40

000

<210> SEQ ID NO 41
<211> LENGTH: 360
<212> TYPE: DNA
<213> ORGANISM: Homo sapiens
<220> FEATURE:
<223> OTHER INFORMATION: Ab5

<400> SEQUENCE: 41
caggtgcagc tggtgcaatc tggggctgag gtgaagaagc ctggggcctc agtgaaggtc    60
tcatgtaaaa tttccggaca cagcctcagt gaactgtcca tccactgggt gcgacagact    120
cccacaaaag gatttgagtg gatgggagga tttgatcctg aagagaatga aatagtctac    180
gcacagaggt tccagggcag agtcaccatg accgaggaca catctataga cacggcctac    240
ctgaccctga gcagcctgag atccgacgac acggccgttt attattgtgc aatagtgggg    300
tctttcagtg gctacccttta ccgcccgtgg ggccaaggga caatggtcac cgtctcgagt    360

<210> SEQ ID NO 42
<211> LENGTH: 120
<212> TYPE: PRT
<213> ORGANISM: Homo sapiens
<220> FEATURE:
<223> OTHER INFORMATION: Ab5

<400> SEQUENCE: 42

Gln Val Gln Leu Val Gln Ser Gly Ala Glu Val Lys Lys Pro Gly Ala
              5                  10                  15

Ser Val Lys Val Ser Cys Lys Ile Ser Gly His Ser Leu Ser Glu Leu
         20                  25                  30

Ser Ile His Trp Val Arg Gln Thr Pro Thr Lys Gly Phe Glu Trp Met
     35                  40                  45

Gly Gly Phe Asp Pro Glu Glu Asn Glu Ile Val Tyr Ala Gln Arg Phe
 50                  55                  60

Gln Gly Arg Val Thr Met Thr Glu Asp Thr Ser Ile Asp Thr Ala Tyr

```
                65                  70                  75                  80
Leu Thr Leu Ser Ser Leu Arg Ser Asp Asp Thr Ala Val Tyr Tyr Cys
                    85                  90                  95

Ala Ile Val Gly Ser Phe Ser Gly Tyr Pro Tyr Arg Pro Trp Gly Gln
            100                 105                 110

Gly Thr Met Val Thr Val Ser Ser
        115                 120
```

<210> SEQ ID NO 43

<400> SEQUENCE: 43

000

<210> SEQ ID NO 44

<400> SEQUENCE: 44

000

<210> SEQ ID NO 45
<211> LENGTH: 11
<212> TYPE: PRT
<213> ORGANISM: Homo sapiens
<220> FEATURE:
<223> OTHER INFORMATION: Ab5

<400> SEQUENCE: 45

```
Val Gly Ser Phe Ser Gly Tyr Pro Tyr Arg Pro
                5                  10
```

<210> SEQ ID NO 46

<400> SEQUENCE: 46

000

<210> SEQ ID NO 47

<400> SEQUENCE: 47

000

<210> SEQ ID NO 48

<400> SEQUENCE: 48

000

<210> SEQ ID NO 49

<400> SEQUENCE: 49

000

<210> SEQ ID NO 50

<400> SEQUENCE: 50

000

<210> SEQ ID NO 51
<211> LENGTH: 360
<212> TYPE: DNA
<213> ORGANISM: Homo sapiens
<220> FEATURE:
<223> OTHER INFORMATION: Ab6

<400> SEQUENCE: 51

```
caggtccagc tggtgcaatc tgggggctgag gtgaagaagc ctggggcctc agtgaaggtc    60
tcatgtaaag tttccggata caccctcact gaactgtcca tccactgggt gcgacaggct   120
cccggaaaag gacttgagtg gatgggagga tttgatcctg aagagaatga aatagtctac   180
gcacagaggt tccagggcag agtcaccatg accgaggaca catctacaga cacggcctac   240
atggaactga gcagcctgag atccgaggac acggccgttt attattgtgc aatagtgggg   300
tctttcagtc ccttgacctt gggcctctgg ggccaaggga caatggtcac cgtctcctca   360
```

<210> SEQ ID NO 52
<211> LENGTH: 120
<212> TYPE: PRT
<213> ORGANISM: Homo sapiens
<220> FEATURE:
<223> OTHER INFORMATION: Ab6

<400> SEQUENCE: 52

Gln Val Gln Leu Val Gln Ser Gly Ala Glu Val Lys Lys Pro Gly Ala
                  5                  10                  15

Ser Val Lys Val Ser Cys Lys Val Ser Gly Tyr Thr Leu Thr Glu Leu
              20                  25                  30

Ser Ile His Trp Val Arg Gln Ala Pro Gly Lys Gly Leu Glu Trp Met
          35                  40                  45

Gly Gly Phe Asp Pro Glu Glu Asn Glu Ile Val Tyr Ala Gln Arg Phe
      50                  55                  60

Gln Gly Arg Val Thr Met Thr Glu Asp Thr Ser Thr Asp Thr Ala Tyr
65                  70                  75                  80

Met Glu Leu Ser Ser Leu Arg Ser Glu Asp Thr Ala Val Tyr Tyr Cys
                  85                  90                  95

Ala Ile Val Gly Ser Phe Ser Pro Leu Thr Leu Gly Leu Trp Gly Gln
              100                 105                 110

Gly Thr Met Val Thr Val Ser Ser
          115                 120

<210> SEQ ID NO 53

<400> SEQUENCE: 53

000

<210> SEQ ID NO 54

<400> SEQUENCE: 54

000

<210> SEQ ID NO 55
<211> LENGTH: 11
<212> TYPE: PRT
<213> ORGANISM: Homo sapiens
<220> FEATURE:
<223> OTHER INFORMATION: Ab6

<400> SEQUENCE: 55

Val Gly Ser Phe Ser Pro Leu Thr Leu Gly Leu
              5                  10

<210> SEQ ID NO 56
<211> LENGTH: 339
<212> TYPE: DNA

```
<213> ORGANISM: Homo sapiens
<220> FEATURE:
<223> OTHER INFORMATION: Ab6

<400> SEQUENCE: 56
cagtctgtgc tgactcagcc gccctcagtg tctggggccc cagggcagag ggtcaccatc    60
tcctgtactg ggagcggctc caacatcggg gcaccttatg atgtaagctg gtaccagcag   120
cttccaggaa cagcccccaa actcctcatc tatcataaca acaagcggcc ctcaggggtc   180
cctgaccgat tctctggctc caagtctggc acctcagcct ccctggccat cactgggctc   240
caggctgagg atgaggctga ttattactgc gcgaccgttg aggccggcct gagtggttcg   300
gttttcggcg gagggaccaa gctgaccgtc ctaggtgcg                          339

<210> SEQ ID NO 57
<211> LENGTH: 113
<212> TYPE: PRT
<213> ORGANISM: Homo sapiens
<220> FEATURE:
<223> OTHER INFORMATION: Ab6

<400> SEQUENCE: 57

Gln Ser Val Leu Thr Gln Pro Pro Ser Val Ser Gly Ala Pro Gly Gln
                 5                  10                  15

Arg Val Thr Ile Ser Cys Thr Gly Ser Gly Ser Asn Ile Gly Ala Pro
             20                  25                  30

Tyr Asp Val Ser Trp Tyr Gln Gln Leu Pro Gly Thr Ala Pro Lys Leu
         35                  40                  45

Leu Ile Tyr His Asn Asn Lys Arg Pro Ser Gly Val Pro Asp Arg Phe
     50                  55                  60

Ser Gly Ser Lys Ser Gly Thr Ser Ala Ser Leu Ala Ile Thr Gly Leu
 65                  70                  75                  80

Gln Ala Glu Asp Glu Ala Asp Tyr Tyr Cys Ala Thr Val Glu Ala Gly
                 85                  90                  95

Leu Ser Gly Ser Val Phe Gly Gly Gly Thr Lys Leu Thr Val Leu Gly
            100                 105                 110

Ala

<210> SEQ ID NO 58

<400> SEQUENCE: 58

000

<210> SEQ ID NO 59

<400> SEQUENCE: 59

000

<210> SEQ ID NO 60
<211> LENGTH: 11
<212> TYPE: PRT
<213> ORGANISM: Homo sapiens
<220> FEATURE:
<223> OTHER INFORMATION: Ab6

<400> SEQUENCE: 60

Ala Thr Val Glu Ala Gly Leu Ser Gly Ser Val
                 5                  10

<210> SEQ ID NO 61
```

<211> LENGTH: 360
<212> TYPE: DNA
<213> ORGANISM: Homo sapiens
<220> FEATURE:
<223> OTHER INFORMATION: Ab7

<400> SEQUENCE: 61

```
caggtgcagc tggtgcaatc tggggctgag gtgaagaagc ctggggcctc agtgaaggtc     60
tcatgtaaaa tttccggaca cagcctcagt gaactgtcca tccactgggt gcgacagact    120
cccacaaaag gatttgagtg gatgggagga tttgatcctg aagagaatga aatagtctac    180
gcacagaggt tccagggcag agtcaccatg accgaggaca catctataga cacggcctac    240
ctgaccctga gcagcctgag atccgacgac acggccgttt attattgtgc aatagtgggg    300
tctttcagtg gccccgtgta cggcctctgg ggcaaaggga caatggtcac cgtctcgagt    360
```

<210> SEQ ID NO 62
<211> LENGTH: 120
<212> TYPE: PRT
<213> ORGANISM: Homo sapiens
<220> FEATURE:
<223> OTHER INFORMATION: Ab7

<400> SEQUENCE: 62

Gln Val Gln Leu Val Gln Ser Gly Ala Glu Val Lys Lys Pro Gly Ala
               5                  10                  15

Ser Val Lys Val Ser Cys Lys Ile Ser Gly His Ser Leu Ser Glu Leu
           20                  25                  30

Ser Ile His Trp Val Arg Gln Thr Pro Thr Lys Gly Phe Glu Trp Met
       35                  40                  45

Gly Gly Phe Asp Pro Glu Glu Asn Glu Ile Val Tyr Ala Gln Arg Phe
   50                  55                  60

Gln Gly Arg Val Thr Met Thr Glu Asp Thr Ser Ile Asp Thr Ala Tyr
65                  70                  75                  80

Leu Thr Leu Ser Ser Leu Arg Ser Asp Asp Thr Ala Val Tyr Tyr Cys
               85                  90                  95

Ala Ile Val Gly Ser Phe Ser Gly Pro Val Tyr Gly Leu Trp Gly Lys
          100                 105                 110

Gly Thr Met Val Thr Val Ser Ser
      115                 120

<210> SEQ ID NO 63

<400> SEQUENCE: 63

000

<210> SEQ ID NO 64

<400> SEQUENCE: 64

000

<210> SEQ ID NO 65
<211> LENGTH: 11
<212> TYPE: PRT
<213> ORGANISM: Homo sapiens
<220> FEATURE:
<223> OTHER INFORMATION: Ab7

<400> SEQUENCE: 65

Val Gly Ser Phe Ser Gly Pro Val Tyr Gly Leu
              5                  10

<210> SEQ ID NO 66

<400> SEQUENCE: 66

000

<210> SEQ ID NO 67

<400> SEQUENCE: 67

000

<210> SEQ ID NO 68

<400> SEQUENCE: 68

000

<210> SEQ ID NO 69

<400> SEQUENCE: 69

000

<210> SEQ ID NO 70

<400> SEQUENCE: 70

000

<210> SEQ ID NO 71
<211> LENGTH: 360
<212> TYPE: DNA
<213> ORGANISM: Homo sapiens
<220> FEATURE:
<223> OTHER INFORMATION: Ab8

<400> SEQUENCE: 71

```
caggtgcagc tggtgcaatc tggggctgag gtgaagaagc ctggggcctc agtgaaggtc      60
tcatgtaaaa tttccggaca cagcctcagt gaactgtcca tccactgggt gcgacagact     120
cccacaaaag gatttgagtg gatgggagga tttgatcctg aagagaatga aatagtctac     180
gcacagaggt tccagggcag agtcaccatg accgaggaca catctataga cacggcctac     240
ctgaccctga gcagcctgag atccgacgac acggccgttt attattgtgc aatagtgggg     300
tctttcagtc ccccggccta ccgcccctgg ggcaaaggga caatggtcac cgtctcgagt     360
```

<210> SEQ ID NO 72
<211> LENGTH: 120
<212> TYPE: PRT
<213> ORGANISM: Homo sapiens
<220> FEATURE:
<223> OTHER INFORMATION: Ab8

<400> SEQUENCE: 72

```
Gln Val Gln Leu Val Gln Ser Gly Ala Glu Val Lys Lys Pro Gly Ala
                5                  10                  15

Ser Val Lys Val Ser Cys Lys Ile Ser Gly His Ser Leu Ser Glu Leu
            20                  25                  30

Ser Ile His Trp Val Arg Gln Thr Pro Thr Lys Gly Phe Glu Trp Met
        35                  40                  45

Gly Gly Phe Asp Pro Glu Glu Asn Glu Ile Val Tyr Ala Gln Arg Phe
    50                  55                  60
```

Gln Gly Arg Val Thr Met Thr Glu Asp Thr Ser Ile Asp Thr Ala Tyr
65                  70                  75                  80

Leu Thr Leu Ser Ser Leu Arg Ser Asp Asp Thr Ala Val Tyr Tyr Cys
            85                  90                  95

Ala Ile Val Gly Ser Phe Ser Pro Pro Ala Tyr Arg Pro Trp Gly Lys
        100                 105                 110

Gly Thr Met Val Thr Val Ser Ser
        115                 120

<210> SEQ ID NO 73

<400> SEQUENCE: 73

000

<210> SEQ ID NO 74

<400> SEQUENCE: 74

000

<210> SEQ ID NO 75
<211> LENGTH: 11
<212> TYPE: PRT
<213> ORGANISM: Homo sapiens
<220> FEATURE:
<223> OTHER INFORMATION: Ab8

<400> SEQUENCE: 75

Val Gly Ser Phe Ser Pro Pro Ala Tyr Arg Pro
                5                   10

<210> SEQ ID NO 76

<400> SEQUENCE: 76

000

<210> SEQ ID NO 77

<400> SEQUENCE: 77

000

<210> SEQ ID NO 78

<400> SEQUENCE: 78

000

<210> SEQ ID NO 79

<400> SEQUENCE: 79

000

<210> SEQ ID NO 80

<400> SEQUENCE: 80

000

<210> SEQ ID NO 81
<211> LENGTH: 360
<212> TYPE: DNA
<213> ORGANISM: Homo sapiens
<220> FEATURE:

<223> OTHER INFORMATION: Ab9

<400> SEQUENCE: 81

```
caggtgcagc tggtgcaatc tgggctgag gtgaagaagc ctggggcctc agtgaaggtc       60
tcatgtaaaa tttccggaca cagcctcagt gaactgtcca tccactgggt gcgacagact     120
cccacaaaag gatttgagtg gatgggagga tttgatcctg aagagaatga aatagtctac     180
gcacagaggt tccagggcag agtcaccatg accgaggaca catctataga cacggcctac     240
ctgaccctga gcagcctgag atccgacgac acggccgttt attattgtgc aatagtgggg     300
tctttcagtc cggtcacgta cggcctctgg ggccaaggga caatggtcac cgtctcgagt     360
```

<210> SEQ ID NO 82
<211> LENGTH: 120
<212> TYPE: PRT
<213> ORGANISM: Homo sapiens
<220> FEATURE:
<223> OTHER INFORMATION: Ab9

<400> SEQUENCE: 82

```
Gln Val Gln Leu Val Gln Ser Gly Ala Glu Val Lys Lys Pro Gly Ala
                 5                  10                  15
Ser Val Lys Val Ser Cys Lys Ile Ser Gly His Ser Leu Ser Glu Leu
            20                  25                  30
Ser Ile His Trp Val Arg Gln Thr Pro Thr Lys Gly Phe Glu Trp Met
        35                  40                  45
Gly Gly Phe Asp Pro Glu Glu Asn Glu Ile Val Tyr Ala Gln Arg Phe
    50                  55                  60
Gln Gly Arg Val Thr Met Thr Glu Asp Thr Ser Ile Asp Thr Ala Tyr
65                  70                  75                  80
Leu Thr Leu Ser Ser Leu Arg Ser Asp Asp Thr Ala Val Tyr Tyr Cys
                85                  90                  95
Ala Ile Val Gly Ser Phe Ser Pro Val Thr Tyr Gly Leu Trp Gly Gln
            100                 105                 110
Gly Thr Met Val Thr Val Ser Ser
        115                 120
```

<210> SEQ ID NO 83

<400> SEQUENCE: 83

000

<210> SEQ ID NO 84

<400> SEQUENCE: 84

000

<210> SEQ ID NO 85
<211> LENGTH: 11
<212> TYPE: PRT
<213> ORGANISM: Homo sapiens
<220> FEATURE:
<223> OTHER INFORMATION: Ab9

<400> SEQUENCE: 85

```
Val Gly Ser Phe Ser Pro Val Thr Tyr Gly Leu
                 5                  10
```

<210> SEQ ID NO 86

<400> SEQUENCE: 86

000

<210> SEQ ID NO 87

<400> SEQUENCE: 87

000

<210> SEQ ID NO 88

<400> SEQUENCE: 88

000

<210> SEQ ID NO 89

<400> SEQUENCE: 89

000

<210> SEQ ID NO 90

<400> SEQUENCE: 90

000

<210> SEQ ID NO 91
<211> LENGTH: 360
<212> TYPE: DNA
<213> ORGANISM: Homo sapiens
<220> FEATURE:
<223> OTHER INFORMATION: Ab10

<400> SEQUENCE: 91

```
caggtgcagc tggtgcaatc tggggctgag gtgaagaagc ctggggcctc agtgaaggtc      60
tcatgtaaaa tttccggaca cagcctcagt gaactgtcca tccactgggt gcgacagact     120
cccacaaaag gatttgagtg gatgggagga tttgatcctg aagagaatga aatagtctac     180
gcacagaggt tccagggcag agtcaccatg accgaggaca catctataga cacggcctac     240
ctgaccctga gcagcctgag atccgacgac acggccgttt attattgtgc aatagtgggg     300
tctttcagtg gcctcgcgta caggccctgg ggcaaaggga caatggtcac catctcgagt     360
```

<210> SEQ ID NO 92
<211> LENGTH: 120
<212> TYPE: PRT
<213> ORGANISM: Homo sapiens
<220> FEATURE:
<223> OTHER INFORMATION: Ab10

<400> SEQUENCE: 92

```
Gln Val Gln Leu Val Gln Ser Gly Ala Glu Val Lys Lys Pro Gly Ala
                5                  10                  15
Ser Val Lys Val Ser Cys Lys Ile Ser Gly His Ser Leu Ser Glu Leu
            20                  25                  30
Ser Ile His Trp Val Arg Gln Thr Pro Thr Lys Gly Phe Glu Trp Met
        35                  40                  45
Gly Gly Phe Asp Pro Glu Glu Asn Glu Ile Val Tyr Ala Gln Arg Phe
    50                  55                  60
Gln Gly Arg Val Thr Met Thr Glu Asp Thr Ser Ile Asp Thr Ala Tyr
65                  70                  75                  80
Leu Thr Leu Ser Ser Leu Arg Ser Asp Asp Thr Ala Val Tyr Tyr Cys
```

```
                    85                  90                  95
Ala Ile Val Gly Ser Phe Ser Gly Leu Ala Tyr Arg Pro Trp Gly Lys
                100                 105                 110

Gly Thr Met Val Thr Ile Ser Ser
        115                 120

<210> SEQ ID NO 93

<400> SEQUENCE: 93

000

<210> SEQ ID NO 94

<400> SEQUENCE: 94

000

<210> SEQ ID NO 95
<211> LENGTH: 11
<212> TYPE: PRT
<213> ORGANISM: Homo sapiens
<220> FEATURE:
<223> OTHER INFORMATION: Ab10

<400> SEQUENCE: 95

Val Gly Ser Phe Ser Gly Leu Ala Tyr Arg Pro
                5                   10

<210> SEQ ID NO 96

<400> SEQUENCE: 96

000

<210> SEQ ID NO 97

<400> SEQUENCE: 97

000

<210> SEQ ID NO 98

<400> SEQUENCE: 98

000

<210> SEQ ID NO 99

<400> SEQUENCE: 99

000

<210> SEQ ID NO 100

<400> SEQUENCE: 100

000

<210> SEQ ID NO 101
<211> LENGTH: 360
<212> TYPE: DNA
<213> ORGANISM: Homo sapiens
<220> FEATURE:
<223> OTHER INFORMATION: Ab11

<400> SEQUENCE: 101
```

```
caggtgcagc tggtgcaatc tggcgctgag gtgaagaagc ctgaggcctc agtgaaggtc      60
tcatgtaaaa ttccgggaca cagcctcagt gaactgtcca tccactgggt gcgacagact     120
cccacaaaag gatttgagtg gatgggagga tttgatcctg aagagaatga aatagtctac     180
gcacagaggt tccagggcag agtcaccatg accgaggaca catctataga cacggcctac     240
ctgaccctga gcagcctgag atccgacgac acggccgttt attattgtgc aatagtgggg     300
tctttcagtc cgatcacgta cggcctctgg ggcaaaggga caatggtcac cgtctcgagt     360
```

<210> SEQ ID NO 102
<211> LENGTH: 120
<212> TYPE: PRT
<213> ORGANISM: Homo sapiens
<220> FEATURE:
<223> OTHER INFORMATION: Ab11

<400> SEQUENCE: 102

Gln Val Gln Leu Val Gln Ser Gly Ala Glu Val Lys Lys Pro Glu Ala
              5                  10                  15
Ser Val Lys Val Ser Cys Lys Ile Pro Gly His Ser Leu Ser Glu Leu
         20                  25                  30
Ser Ile His Trp Val Arg Gln Thr Pro Thr Lys Gly Phe Glu Trp Met
     35                  40                  45
Gly Gly Phe Asp Pro Glu Glu Asn Glu Ile Val Tyr Ala Gln Arg Phe
 50                  55                  60
Gln Gly Arg Val Thr Met Thr Glu Asp Thr Ser Ile Asp Thr Ala Tyr
65                  70                  75                  80
Leu Thr Leu Ser Ser Leu Arg Ser Asp Asp Thr Ala Val Tyr Tyr Cys
                 85                  90                  95
Ala Ile Val Gly Ser Phe Ser Pro Ile Thr Tyr Gly Leu Trp Gly Lys
            100                 105                 110
Gly Thr Met Val Thr Val Ser Ser
        115                 120

<210> SEQ ID NO 103

<400> SEQUENCE: 103

000

<210> SEQ ID NO 104

<400> SEQUENCE: 104

000

<210> SEQ ID NO 105
<211> LENGTH: 11
<212> TYPE: PRT
<213> ORGANISM: Homo sapiens
<220> FEATURE:
<223> OTHER INFORMATION: Ab11

<400> SEQUENCE: 105

Val Gly Ser Phe Ser Pro Ile Thr Tyr Gly Leu
              5                  10

<210> SEQ ID NO 106
<211> LENGTH: 339
<212> TYPE: DNA
<213> ORGANISM: Homo sapiens
<220> FEATURE:
<223> OTHER INFORMATION: Ab11

-continued

<400> SEQUENCE: 106

```
caggctgtgc tgactcagcc gtcctcagtg tctggggtcc cagggcagag ggtcaccatc    60
tcctgtactg ggagcggctc caacatcggg gcaccttatg atgtaagctg gtaccagcag   120
cttccaggaa cagcccccaa actcctcatc tatcataaca acaagcggcc ctcaggggtc   180
cctgaccgat tctctgcctc caagtctggc acctcagcct ccctggccat cactgggctc   240
caggctgacg atgaggctga ttattactgc cagtcctatg acagcagcct gagtggttcg   300
gttttcggcg gagggaccaa ggtcaccgtc ctaggtgcg                          339
```

<210> SEQ ID NO 107
<211> LENGTH: 113
<212> TYPE: PRT
<213> ORGANISM: Homo sapiens
<220> FEATURE:
<223> OTHER INFORMATION: Ab11

<400> SEQUENCE: 107

Gln Ala Val Leu Thr Gln Pro Ser Ser Val Ser Gly Val Pro Gly Gln
                 5                  10                  15
Arg Val Thr Ile Ser Cys Thr Gly Ser Gly Ser Asn Ile Gly Ala Pro
            20                  25                  30
Tyr Asp Val Ser Trp Tyr Gln Gln Leu Pro Gly Thr Ala Pro Lys Leu
        35                  40                  45
Leu Ile Tyr His Asn Asn Lys Arg Pro Ser Gly Val Pro Asp Arg Phe
    50                  55                  60
Ser Ala Ser Lys Ser Gly Thr Ser Ala Ser Leu Ala Ile Thr Gly Leu
65                  70                  75                  80
Gln Ala Asp Asp Glu Ala Asp Tyr Tyr Cys Gln Ser Tyr Asp Ser Ser
                85                  90                  95
Leu Ser Gly Ser Val Phe Gly Gly Gly Thr Lys Val Thr Val Leu Gly
            100                 105                 110
Ala

<210> SEQ ID NO 108
<400> SEQUENCE: 108
000

<210> SEQ ID NO 109
<400> SEQUENCE: 109
000

<210> SEQ ID NO 110
<400> SEQUENCE: 110
000

<210> SEQ ID NO 111
<400> SEQUENCE: 111
000

<210> SEQ ID NO 112
<400> SEQUENCE: 112

000

<210> SEQ ID NO 113

<400> SEQUENCE: 113

000

<210> SEQ ID NO 114

<400> SEQUENCE: 114

000

<210> SEQ ID NO 115
<211> LENGTH: 11
<212> TYPE: PRT
<213> ORGANISM: Homo sapiens
<220> FEATURE:
<223> OTHER INFORMATION: Ab12

<400> SEQUENCE: 115

Val Gly Ser Phe Ser Gly Trp Ala Phe Asp Tyr
                5                   10

<210> SEQ ID NO 116
<211> LENGTH: 339
<212> TYPE: DNA
<213> ORGANISM: Homo sapiens
<220> FEATURE:
<223> OTHER INFORMATION: Ab12

<400> SEQUENCE: 116

```
caggctgtgc tgactcagcc gtcctcagtg tctggggccc cagggcagag ggtcaccatc    60
tcctgtactg ggagcggctc caacatcggg gcaccttatg atgtaagctg gtaccagcag   120
cttccaggaa cagcccccaa actcctcatc tatcataaca acaagcggcc ctcagggatc   180
cctgaccgat tctctgcctc caagtctggc acctcagcct ccctggccat cactgggctc   240
caggctgacg atgaggctga ttattactgc cagtcctatg acagcgagcc gaccgagatc   300
cgcttcgggg agggaccaa gctcaccgtc ctaggtgcg                            339
```

<210> SEQ ID NO 117
<211> LENGTH: 113
<212> TYPE: PRT
<213> ORGANISM: Homo sapiens
<220> FEATURE:
<223> OTHER INFORMATION: Ab12

<400> SEQUENCE: 117

Gln Ala Val Leu Thr Gln Pro Ser Ser Val Ser Gly Ala Pro Gly Gln
                5                   10                  15

Arg Val Thr Ile Ser Cys Thr Gly Ser Gly Ser Asn Ile Gly Ala Pro
            20                  25                  30

Tyr Asp Val Ser Trp Tyr Gln Gln Leu Pro Gly Thr Ala Pro Lys Leu
        35                  40                  45

Leu Ile Tyr His Asn Asn Lys Arg Pro Ser Gly Val Pro Asp Arg Phe
    50                  55                  60

Ser Ala Ser Lys Ser Gly Thr Ser Ala Ser Leu Ala Ile Thr Gly Leu
65                  70                  75                  80

Gln Ala Asp Asp Glu Ala Asp Tyr Tyr Cys Gln Ser Tyr Asp Ser Glu
                85                  90                  95

```
Pro Thr Glu Ile Arg Phe Gly Gly Gly Thr Lys Leu Thr Val Leu Gly
            100                 105                 110
Ala

<210> SEQ ID NO 118

<400> SEQUENCE: 118

000

<210> SEQ ID NO 119

<400> SEQUENCE: 119

000

<210> SEQ ID NO 120
<211> LENGTH: 11
<212> TYPE: PRT
<213> ORGANISM: Homo sapiens
<220> FEATURE:
<223> OTHER INFORMATION: Ab12

<400> SEQUENCE: 120

Gln Ser Tyr Asp Ser Glu Pro Thr Glu Ile Arg
                5                   10

<210> SEQ ID NO 121

<400> SEQUENCE: 121

000

<210> SEQ ID NO 122

<400> SEQUENCE: 122

000

<210> SEQ ID NO 123

<400> SEQUENCE: 123

000

<210> SEQ ID NO 124

<400> SEQUENCE: 124

000

<210> SEQ ID NO 125
<211> LENGTH: 11
<212> TYPE: PRT
<213> ORGANISM: Homo sapiens
<220> FEATURE:
<223> OTHER INFORMATION: Ab13

<400> SEQUENCE: 125

Val Gly Ser Phe Ser Gly Trp Ala Phe Asp Tyr
                5                   10

<210> SEQ ID NO 126
<211> LENGTH: 339
<212> TYPE: DNA
<213> ORGANISM: Homo sapiens
<220> FEATURE:
<223> OTHER INFORMATION: Ab13
```

<400> SEQUENCE: 126

```
caggctgtgc tgactcagcc gtcctcagtg tctggggccc cagggcagag ggtcaccatc      60
tcctgtactg ggagcggctc caacatcggg gcaccttatg atgtaagctg gtaccagcag     120
cttccaggaa cagcccccaa actcctcatc tatcataaca acaagcggcc ctcagggggtc    180
cctgaccgat tctctgcctc caagtctggc acctcagcct ccctggccat cactgggctc     240
caggctgacg atgaggctga ttattactgc cagtcctatg acagcaggac gggcatcatc     300
gtcttcgggg gagggaccaa ggtcaccgtc ctaggtgcg                            339
```

<210> SEQ ID NO 127
<211> LENGTH: 113
<212> TYPE: PRT
<213> ORGANISM: Homo sapiens
<220> FEATURE:
<223> OTHER INFORMATION: Ab13

<400> SEQUENCE: 127

Gln Ala Val Leu Thr Gln Pro Ser Ser Val Ser Gly Ala Pro Gly Gln
1               5                   10                  15
Arg Val Thr Ile Ser Cys Thr Gly Ser Gly Ser Asn Ile Gly Ala Pro
            20                  25                  30
Tyr Asp Val Ser Trp Tyr Gln Gln Leu Pro Gly Thr Ala Pro Lys Leu
        35                  40                  45
Leu Ile Tyr His Asn Asn Lys Arg Pro Ser Gly Val Pro Asp Arg Phe
    50                  55                  60
Ser Ala Ser Lys Ser Gly Thr Ser Ala Ser Leu Ala Ile Thr Gly Leu
65                  70                  75                  80
Gln Ala Asp Asp Glu Ala Asp Tyr Tyr Cys Gln Ser Tyr Asp Ser Arg
                85                  90                  95
Thr Gly Ile Ile Val Phe Gly Gly Gly Thr Lys Val Thr Val Leu Gly
            100                 105                 110
Ala

<210> SEQ ID NO 128

<400> SEQUENCE: 128

000

<210> SEQ ID NO 129

<400> SEQUENCE: 129

000

<210> SEQ ID NO 130
<211> LENGTH: 11
<212> TYPE: PRT
<213> ORGANISM: Homo sapiens
<220> FEATURE:
<223> OTHER INFORMATION: Ab13

<400> SEQUENCE: 130

Gln Ser Tyr Asp Ser Arg Thr Gly Ile Ile Val
1               5                   10

<210> SEQ ID NO 131
<211> LENGTH: 360
<212> TYPE: DNA
<213> ORGANISM: Homo sapiens

```
<220> FEATURE:
<223> OTHER INFORMATION: Ab14

<400> SEQUENCE: 131
caggtgcagc tggtgcaatc tggggctgag gtgaagaagc ctggggcctc agtgaaggtc      60
tcatgtaaaa tttccggaca cagcctcagt gaactgtcca tccactgggt gcgacagact     120
cccacaaaag gatttgagtg gatgggagga tttgatcctg aagagaatga aatagtctac     180
gcacagaggt tccagggcag agtcaccatg accgaggaca catctataga cacggcctac     240
ctgaccctga gcagcctgag atccgacgac acggccgttt attattgttc aatattgggg     300
agcgtgaccg cctgggcctt tgactactgg ggcaaaggga caatggtcac cgtctcgagt     360

<210> SEQ ID NO 132
<211> LENGTH: 120
<212> TYPE: PRT
<213> ORGANISM: Homo sapiens
<220> FEATURE:
<223> OTHER INFORMATION: Ab14

<400> SEQUENCE: 132

Gln Val Gln Leu Val Gln Ser Gly Ala Glu Val Lys Lys Pro Gly Ala
                  5                  10                  15

Ser Val Lys Val Ser Cys Lys Ile Ser Gly His Ser Leu Ser Glu Leu
             20                  25                  30

Ser Ile His Trp Val Arg Gln Thr Pro Thr Lys Gly Phe Glu Trp Met
         35                  40                  45

Gly Gly Phe Asp Pro Glu Glu Asn Glu Ile Val Tyr Ala Gln Arg Phe
     50                  55                  60

Gln Gly Arg Val Thr Met Thr Glu Asp Thr Ser Ile Asp Thr Ala Tyr
 65                  70                  75                  80

Leu Thr Leu Ser Ser Leu Arg Ser Asp Asp Thr Ala Val Tyr Tyr Cys
                 85                  90                  95

Ser Ile Leu Gly Ser Val Thr Ala Trp Ala Phe Asp Tyr Trp Gly Lys
            100                 105                 110

Gly Thr Met Val Thr Val Ser Ser
        115                 120

<210> SEQ ID NO 133

<400> SEQUENCE: 133

000

<210> SEQ ID NO 134

<400> SEQUENCE: 134

000

<210> SEQ ID NO 135
<211> LENGTH: 11
<212> TYPE: PRT
<213> ORGANISM: Homo sapiens
<220> FEATURE:
<223> OTHER INFORMATION: Ab14

<400> SEQUENCE: 135

Leu Gly Ser Val Thr Ala Trp Ala Phe Asp Tyr
                  5                  10

<210> SEQ ID NO 136
```

```
<211> LENGTH: 339
<212> TYPE: DNA
<213> ORGANISM: Homo sapiens
<220> FEATURE:
<223> OTHER INFORMATION: Ab14

<400> SEQUENCE: 136
caggctgtgc tgactcagcc gtcctcagtg tctggggccc cagggcagag ggtcaccatc    60
tcctgtactg ggagcggctc caacatcggg gcaccttatg atgtaagctg gtaccagcag   120
cttccaggaa cagcccccaa actcctcatc tatcataaca acaagcggcc ctcaggggtc   180
cctgaccgat tctctgcctc caagtctggc acctcagcct ccctggccat cactgggctc   240
caggctgacg atgaggctga ttattactgc cagtcctatg acagcgagga caggatgacg   300
gagttcgggg gagggaccaa ggtcaccgtc ctaggtgcg                          339

<210> SEQ ID NO 137
<211> LENGTH: 113
<212> TYPE: PRT
<213> ORGANISM: Homo sapiens
<220> FEATURE:
<223> OTHER INFORMATION: Ab14

<400> SEQUENCE: 137

Gln Ala Val Leu Thr Gln Pro Ser Ser Val Ser Gly Ala Pro Gly Gln
                 5                  10                  15

Arg Val Thr Ile Ser Cys Thr Gly Ser Gly Ser Asn Ile Gly Ala Pro
             20                  25                  30

Tyr Asp Val Ser Trp Tyr Gln Gln Leu Pro Gly Thr Ala Pro Lys Leu
         35                  40                  45

Leu Ile Tyr His Asn Asn Lys Arg Pro Ser Gly Val Pro Asp Arg Phe
     50                  55                  60

Ser Ala Ser Lys Ser Gly Thr Ser Ala Ser Leu Ala Ile Thr Gly Leu
 65                  70                  75                  80

Gln Ala Asp Asp Glu Ala Asp Tyr Tyr Cys Gln Ser Tyr Asp Ser Glu
                 85                  90                  95

Asp Arg Met Thr Glu Phe Gly Gly Gly Thr Lys Val Thr Val Leu Gly
                100                 105                 110

Ala

<210> SEQ ID NO 138

<400> SEQUENCE: 138

000

<210> SEQ ID NO 139

<400> SEQUENCE: 139

000

<210> SEQ ID NO 140
<211> LENGTH: 11
<212> TYPE: PRT
<213> ORGANISM: Homo sapiens
<220> FEATURE:
<223> OTHER INFORMATION: Ab14

<400> SEQUENCE: 140

Gln Ser Tyr Asp Ser Glu Asp Arg Met Thr Glu
                 5                  10
```

<210> SEQ ID NO 141
<211> LENGTH: 360
<212> TYPE: DNA
<213> ORGANISM: Homo sapiens
<220> FEATURE:
<223> OTHER INFORMATION: Ab15

<400> SEQUENCE: 141

```
caggtgcagc tggtgcaatc tgggctgag gtgaagaagc ctggggcctc agtgaaggtc      60
tcatgtaaaa tttccggaca cagcctcagt gaactgtcca tccactgggt gcgacagact     120
cccacaaaag gatttgagtg gatgggagga tttgatcctg aagagaatga aatagtctac     180
gcacagaggt tccagggcag agtcaccatg accgaggaca catctataga cacggcctac     240
ctgaccctga gcagcctgag atccgacgac acggccgttt attattgttc aatagccggg     300
agcatccccg gctgggcctt tgactactgg ggcaaaggga caatggtcac cgtctcgagt     360
```

<210> SEQ ID NO 142
<211> LENGTH: 120
<212> TYPE: PRT
<213> ORGANISM: Homo sapiens
<220> FEATURE:
<223> OTHER INFORMATION: Ab15

<400> SEQUENCE: 142

Gln Val Gln Leu Val Gln Ser Gly Ala Glu Val Lys Lys Pro Gly Ala
                5                   10                  15

Ser Val Lys Val Ser Cys Lys Ile Ser Gly His Ser Leu Ser Glu Leu
            20                  25                  30

Ser Ile His Trp Val Arg Gln Thr Pro Thr Lys Gly Phe Glu Trp Met
        35                  40                  45

Gly Gly Phe Asp Pro Glu Glu Asn Glu Ile Val Tyr Ala Gln Arg Phe
    50                  55                  60

Gln Gly Arg Val Thr Met Thr Glu Asp Thr Ser Ile Asp Thr Ala Tyr
65                  70                  75                  80

Leu Thr Leu Ser Ser Leu Arg Ser Asp Asp Thr Ala Val Tyr Tyr Cys
                85                  90                  95

Ser Ile Ala Gly Ser Ile Pro Gly Trp Ala Phe Asp Tyr Trp Gly Lys
            100                 105                 110

Gly Thr Met Val Thr Val Ser Ser
        115                 120

<210> SEQ ID NO 143

<400> SEQUENCE: 143

000

<210> SEQ ID NO 144

<400> SEQUENCE: 144

000

<210> SEQ ID NO 145
<211> LENGTH: 11
<212> TYPE: PRT
<213> ORGANISM: Homo sapiens
<220> FEATURE:
<223> OTHER INFORMATION: Ab15

<400> SEQUENCE: 145

```
Ala Gly Ser Ile Pro Gly Trp Ala Phe Asp Tyr
            5                  10
```

<210> SEQ ID NO 146
<211> LENGTH: 339
<212> TYPE: DNA
<213> ORGANISM: Homo sapiens
<220> FEATURE:
<223> OTHER INFORMATION: Ab15

<400> SEQUENCE: 146

```
caggctgtgc tgactcagcc gtcctcagtg tctggggccc cagggcagag ggtcaccatc    60
tcctgtactg ggagcggctc caacatcggg gcaccttatg atgtaagctg gtaccagcag   120
cttccaggaa cagcccccaa actcctcatc tatcataaca acaagcggcc ctcaggggtc   180
cctgaccgat tctctgcctc caagtctggc acctcagcct ccctggccat cactgggctc   240
caggctgacg atgaggctga ttattactgc cagtcctatg acagccagtt gattagcgcc   300
gccttcgggg gagggaccaa ggtcaccgtc ctaggtgcg                          339
```

<210> SEQ ID NO 147
<211> LENGTH: 113
<212> TYPE: PRT
<213> ORGANISM: Homo sapiens
<220> FEATURE:
<223> OTHER INFORMATION: Ab15

<400> SEQUENCE: 147

```
Gln Ala Val Leu Thr Gln Pro Ser Ser Val Ser Gly Ala Pro Gly Gln
                5                  10                  15

Arg Val Thr Ile Ser Cys Thr Gly Ser Gly Ser Asn Ile Gly Ala Pro
            20                  25                  30

Tyr Asp Val Ser Trp Tyr Gln Gln Leu Pro Gly Thr Ala Pro Lys Leu
        35                  40                  45

Leu Ile Tyr His Asn Asn Lys Arg Pro Ser Gly Val Pro Asp Arg Phe
    50                  55                  60

Ser Ala Ser Lys Ser Gly Thr Ser Ala Ser Leu Ala Ile Thr Gly Leu
65                  70                  75                  80

Gln Ala Asp Asp Glu Ala Asp Tyr Tyr Cys Gln Ser Tyr Asp Ser Gln
                85                  90                  95

Leu Ile Ser Ala Ala Phe Gly Gly Gly Thr Lys Val Thr Val Leu Gly
            100                 105                 110

Ala
```

<210> SEQ ID NO 148

<400> SEQUENCE: 148

000

<210> SEQ ID NO 149

<400> SEQUENCE: 149

000

<210> SEQ ID NO 150
<211> LENGTH: 11
<212> TYPE: PRT
<213> ORGANISM: Homo sapiens
<220> FEATURE:
<223> OTHER INFORMATION: Ab15

-continued

<400> SEQUENCE: 150

Gln Ser Tyr Asp Ser Gln Leu Ile Ser Ala Ala
                 5                  10

<210> SEQ ID NO 151
<211> LENGTH: 360
<212> TYPE: DNA
<213> ORGANISM: Homo sapiens
<220> FEATURE:
<223> OTHER INFORMATION: Ab16

<400> SEQUENCE: 151
caggtgcagc tggtgcaatc tggggctgag gtgaagaagc ctggggcctc agtgaaggtc      60
tcatgtaaaa tttccggaca cagcctcagt gaactgtcca tccactgggt gcgacagact     120
cccacaaaag gatttgagtg gatgggagga tttgatcctg aagagaatga aatagtctac     180
gcacagaggt tccagggcag agtcaccatg accgaggaca catctataga cacggcctac     240
ctgaccctga gcagcctgag atccgacgac acggccgttt attattgttc aatagtgggg     300
tctttcagtc cgttgaccat gggcctctgg ggcaaaggga caatggtcac cgtctcgagt     360

<210> SEQ ID NO 152
<211> LENGTH: 120
<212> TYPE: PRT
<213> ORGANISM: Homo sapiens
<220> FEATURE:
<223> OTHER INFORMATION: Ab16

<400> SEQUENCE: 152

Gln Val Gln Leu Val Gln Ser Gly Ala Glu Val Lys Lys Pro Gly Ala
                 5                  10                  15

Ser Val Lys Val Ser Cys Lys Ile Ser Gly His Ser Leu Ser Glu Leu
             20                  25                  30

Ser Ile His Trp Val Arg Gln Thr Pro Thr Lys Gly Phe Glu Trp Met
         35                  40                  45

Gly Gly Phe Asp Pro Glu Glu Asn Glu Ile Val Tyr Ala Gln Arg Phe
     50                  55                  60

Gln Gly Arg Val Thr Met Thr Glu Asp Thr Ser Ile Asp Thr Ala Tyr
 65                  70                  75                  80

Leu Thr Leu Ser Ser Leu Arg Ser Asp Asp Thr Ala Val Tyr Tyr Cys
                 85                  90                  95

Ser Ile Val Gly Ser Phe Ser Pro Leu Thr Met Gly Leu Trp Gly Lys
            100                 105                 110

Gly Thr Met Val Thr Val Ser Ser
        115                 120

<210> SEQ ID NO 153

<400> SEQUENCE: 153

000

<210> SEQ ID NO 154

<400> SEQUENCE: 154

000

<210> SEQ ID NO 155
<211> LENGTH: 11
<212> TYPE: PRT
<213> ORGANISM: Homo sapiens

```
<220> FEATURE:
<223> OTHER INFORMATION: Ab16

<400> SEQUENCE: 155

Val Gly Ser Phe Ser Pro Leu Thr Met Gly Leu
                5                   10

<210> SEQ ID NO 156
<211> LENGTH: 339
<212> TYPE: DNA
<213> ORGANISM: Homo sapiens
<220> FEATURE:
<223> OTHER INFORMATION: Ab16

<400> SEQUENCE: 156
caggctgtgc tgactcagcc gtcctcagtg tctggggccc cagggcagag ggtcaccatc      60
tcctgtactg ggagcggctc caacatcggg gcaccttatg atgtaagctg gtaccagcag     120
cttccaggaa cagcccccaa actcctcatc tatcataaca acaagcggcc ctcagggggtc    180 cctgaccgat tctctgcctc caagtctggc acctcagcct ccctggccat cactgggctc     240
caggctgagg atgaggctga ttattactgc gcgacctccg acgagatcct gagtggttcg     300
gttttcgggg gagggaccaa ggtcaccgtc ctaggtgcg                            339

<210> SEQ ID NO 157
<211> LENGTH: 113
<212> TYPE: PRT
<213> ORGANISM: Homo sapiens
<220> FEATURE:
<223> OTHER INFORMATION: Ab16

<400> SEQUENCE: 157

Gln Ala Val Leu Thr Gln Pro Ser Ser Val Ser Gly Ala Pro Gly Gln
                5                   10                  15

Arg Val Thr Ile Ser Cys Thr Gly Ser Gly Ser Asn Ile Gly Ala Pro
            20                  25                  30

Tyr Asp Val Ser Trp Tyr Gln Gln Leu Pro Gly Thr Ala Pro Lys Leu
        35                  40                  45

Leu Ile Tyr His Asn Asn Lys Arg Pro Ser Gly Val Pro Asp Arg Phe
    50                  55                  60

Ser Ala Ser Lys Ser Gly Thr Ser Ala Ser Leu Ala Ile Thr Gly Leu
65                  70                  75                  80

Gln Ala Glu Asp Glu Ala Asp Tyr Tyr Cys Ala Thr Ser Asp Glu Ile
                85                  90                  95

Leu Ser Gly Ser Val Phe Gly Gly Gly Thr Lys Val Thr Val Leu Gly
            100                 105                 110

Ala

<210> SEQ ID NO 158

<400> SEQUENCE: 158

000

<210> SEQ ID NO 159

<400> SEQUENCE: 159

000

<210> SEQ ID NO 160
<211> LENGTH: 11
```

```
<212> TYPE: PRT
<213> ORGANISM: Homo sapiens
<220> FEATURE:
<223> OTHER INFORMATION: Ab16

<400> SEQUENCE: 160

Ala Thr Ser Asp Glu Ile Leu Ser Gly Ser Val
                5                   10

<210> SEQ ID NO 161
<211> LENGTH: 360
<212> TYPE: DNA
<213> ORGANISM: Homo sapiens
<220> FEATURE:
<223> OTHER INFORMATION: Ab17

<400> SEQUENCE: 161
caggtgcagc tggtgcaatc tggggctgag gtgaagaagc ctggggcctc agtgaaggtc      60
tcatgtaaaa tttccggaca cagcctcagt gaactgtcca tccactgggt gcgacagact     120
cccacaaaag gatttgagtg gatgggagga tttgatcctg aagagaatga aatagtctac     180
gcacagaggt tccagggcag agtcaccatg accgaggaca catctataga cacggcctac     240
ctgaccctga gcagcctgag atccgacgac acggccgttt attattgttc aatagtgggg     300
tctttcagtc ccctgacgat ggggttgtgg ggcaaaggga caatggtcac cgtctcgagt     360

<210> SEQ ID NO 162

<400> SEQUENCE: 162

000

<210> SEQ ID NO 163

<400> SEQUENCE: 163

000

<210> SEQ ID NO 164

<400> SEQUENCE: 164

000

<210> SEQ ID NO 165
<211> LENGTH: 11
<212> TYPE: PRT
<213> ORGANISM: Homo sapiens
<220> FEATURE:
<223> OTHER INFORMATION: Ab17

<400> SEQUENCE: 165

Val Gly Ser Phe Ser Pro Leu Thr Met Gly Leu
                5                   10

<210> SEQ ID NO 166
<211> LENGTH: 339
<212> TYPE: DNA
<213> ORGANISM: Homo sapiens
<220> FEATURE:
<223> OTHER INFORMATION: Ab17

<400> SEQUENCE: 166
caggctgtgc tgactcagcc gtcctcagtg tctggggccc cagggcagag ggtcaccatc      60
tcctgtactg ggagcggctc caacatcggg gcaccttatg atgtaagctg gtaccagcag     120
```

```
cttccaggaa cagcccccaa actcctcatc tatcataaca acaagcggcc ctcaggggtc       180
cctgaccgat tctctgcctc caagtctggc acctcagcct ccctggccat cactgggctc       240
caggctgacg atgaggctga ttattactgc gcgaccgtcg aggacggcct gagtggttcg       300
gttttcgggg gagggaccaa ggtcaccgtc ctaggtgcg                              339
```

<210> SEQ ID NO 167
<211> LENGTH: 113
<212> TYPE: PRT
<213> ORGANISM: Homo sapiens
<220> FEATURE:
<223> OTHER INFORMATION: Ab17

<400> SEQUENCE: 167

Gln Ala Val Leu Thr Gln Pro Ser Ser Val Ser Gly Ala Pro Gly Gln
                 5                  10                  15

Arg Val Thr Ile Ser Cys Thr Gly Ser Gly Ser Asn Ile Gly Ala Pro
             20                  25                  30

Tyr Asp Val Ser Trp Tyr Gln Gln Leu Pro Gly Thr Ala Pro Lys Leu
         35                  40                  45

Leu Ile Tyr His Asn Asn Lys Arg Pro Ser Gly Val Pro Asp Arg Phe
 50                  55                  60

Ser Ala Ser Lys Ser Gly Thr Ser Ala Ser Leu Ala Ile Thr Gly Leu
 65                  70                  75                  80

Gln Ala Asp Asp Glu Ala Asp Tyr Tyr Cys Ala Thr Val Glu Asp Gly
                 85                  90                  95

Leu Ser Gly Ser Val Phe Gly Gly Gly Thr Lys Val Thr Val Leu Gly
            100                 105                 110

Ala

<210> SEQ ID NO 168

<400> SEQUENCE: 168

000

<210> SEQ ID NO 169

<400> SEQUENCE: 169

000

<210> SEQ ID NO 170
<211> LENGTH: 11
<212> TYPE: PRT
<213> ORGANISM: Homo sapiens
<220> FEATURE:
<223> OTHER INFORMATION: Ab17

<400> SEQUENCE: 170

Ala Thr Val Glu Asp Gly Leu Ser Gly Ser Val
                 5                  10

<210> SEQ ID NO 171
<211> LENGTH: 360
<212> TYPE: DNA
<213> ORGANISM: Homo sapiens
<220> FEATURE:
<223> OTHER INFORMATION: Ab18

<400> SEQUENCE: 171

```
caggtgcagc tggtgcaatc tgggggctgag gtgaagaagc ctggggcctc agtgaaggtc       60
```

```
tcatgtaaaa tttccggaca cagcctcagt gaactgttca tccactgggt gcgacagact        120
cccacaaaag gatttgagtg gatgggagga tttgatcctg aagagaatga aatagtctac        180
gcacagaggt tccagggcag agtcaccatg accgaggaca catctataga cacggcctac        240
ctgaccctga gcagcctgag atccgacgac acggccgttt attattgttc aacagtgggg        300
tctttcagtg ggcccgccct tcacctctgg ggcaaaggga caatggtcac cgtctcgagt        360
```

<210> SEQ ID NO 172
<211> LENGTH: 120
<212> TYPE: PRT
<213> ORGANISM: Homo sapiens
<220> FEATURE:
<223> OTHER INFORMATION: Ab18

<400> SEQUENCE: 172

Gln Val Gln Leu Val Gln Ser Gly Ala Glu Val Lys Lys Pro Gly Ala
1               5                   10                  15

Ser Val Lys Val Ser Cys Lys Ile Ser Gly His Ser Leu Ser Glu Leu
            20                  25                  30

Phe Ile His Trp Val Arg Gln Thr Pro Thr Lys Gly Phe Glu Trp Met
        35                  40                  45

Gly Gly Phe Asp Pro Glu Glu Asn Glu Ile Val Tyr Ala Gln Arg Phe
    50                  55                  60

Gln Gly Arg Val Thr Met Thr Glu Asp Thr Ser Ile Asp Thr Ala Tyr
65                  70                  75                  80

Leu Thr Leu Ser Ser Leu Arg Ser Asp Asp Thr Ala Val Tyr Tyr Cys
                85                  90                  95

Ser Thr Val Gly Ser Phe Ser Gly Pro Ala Leu His Leu Trp Gly Lys
            100                 105                 110

Gly Thr Met Val Thr Val Ser Ser
        115                 120

<210> SEQ ID NO 173
<211> LENGTH: 5
<212> TYPE: PRT
<213> ORGANISM: Homo sapiens
<220> FEATURE:
<223> OTHER INFORMATION: Ab18

<400> SEQUENCE: 173

Glu Leu Phe Ile His
1               5

<210> SEQ ID NO 174

<400> SEQUENCE: 174

000

<210> SEQ ID NO 175
<211> LENGTH: 11
<212> TYPE: PRT
<213> ORGANISM: Homo sapiens
<220> FEATURE:
<223> OTHER INFORMATION: Ab18

<400> SEQUENCE: 175

Val Gly Ser Phe Ser Gly Pro Ala Leu His Leu
1               5                   10

<210> SEQ ID NO 176
<211> LENGTH: 339

```
<212> TYPE: DNA
<213> ORGANISM: Homo sapiens
<220> FEATURE:
<223> OTHER INFORMATION: Ab18

<400> SEQUENCE: 176
caggctgtgc tgactcagcc gtcctcagtg tctggggccc cagggcagag ggtcaccatc      60
tcctgtactg ggagcggctc caacatcggg gcaccttatg atgtaagctg gtaccagcag     120
cttccaggaa cagcccccaa actcctcatc tatcataaca acaagcggcc ctcagggdtc     180
cctgaccgat tctctgcctc caagtctggc acctcagcct ccctggccat cactgggctc     240
caggctgacg atgaggctga ttattactgc cagtcctatg acagccagtg gaaccagccc     300
ctcttcgggg gagggaccaa ggtcaccgtc ctaggtgcg                            339

<210> SEQ ID NO 177
<211> LENGTH: 113
<212> TYPE: PRT
<213> ORGANISM: Homo sapiens
<220> FEATURE:
<223> OTHER INFORMATION: Ab18

<400> SEQUENCE: 177

Gln Ala Val Leu Thr Gln Pro Ser Ser Val Ser Gly Ala Pro Gly Gln
                 5                  10                  15

Arg Val Thr Ile Ser Cys Thr Gly Ser Gly Ser Asn Ile Gly Ala Pro
             20                  25                  30

Tyr Asp Val Ser Trp Tyr Gln Gln Leu Pro Gly Thr Ala Pro Lys Leu
         35                  40                  45

Leu Ile Tyr His Asn Asn Lys Arg Pro Ser Gly Val Pro Asp Arg Phe
     50                  55                  60

Ser Ala Ser Lys Ser Gly Thr Ser Ala Ser Leu Ala Ile Thr Gly Leu
 65                  70                  75                  80

Gln Ala Asp Asp Glu Ala Asp Tyr Tyr Cys Gln Ser Tyr Asp Ser Gln
                 85                  90                  95

Trp Asn Gln Pro Leu Phe Gly Gly Gly Thr Lys Val Thr Val Leu Gly
            100                 105                 110

Ala

<210> SEQ ID NO 178

<400> SEQUENCE: 178

000

<210> SEQ ID NO 179

<400> SEQUENCE: 179

000

<210> SEQ ID NO 180
<211> LENGTH: 11
<212> TYPE: PRT
<213> ORGANISM: Homo sapiens
<220> FEATURE:
<223> OTHER INFORMATION: Ab18

<400> SEQUENCE: 180

Gln Ser Tyr Asp Ser Gln Trp Asn Gln Pro Leu
                 5                  10
```

<210> SEQ ID NO 181
<211> LENGTH: 360
<212> TYPE: DNA
<213> ORGANISM: Homo sapiens
<220> FEATURE:
<223> OTHER INFORMATION: Ab19

<400> SEQUENCE: 181

```
caggtgcagc tggtgcaatc tggggctgag gtgaagaagc ctggggcctc agtgaaggtc    60
tcatgtaaaa tttccggaca cagcctcagt gaactgtcca tccactgggt gcgacagact   120
cccacaaaag gatttgagtg gatgggagga tttgatcctg aagagaatga aatagtctac   180
gcacagaggt tccagggcag agtcaccatg accgaggaca catctataga cacggcctac   240
ctgaccctga gcagcctgag atccgacgac acggccgttt attattgtgc aatagtgggg   300
tctgtcagtc gcatcacgta cggcttctgg ggcaaaggga caatggtcac cgtctcgagt   360
```

<210> SEQ ID NO 182
<211> LENGTH: 120
<212> TYPE: PRT
<213> ORGANISM: Homo sapiens
<220> FEATURE:
<223> OTHER INFORMATION: Ab19

<400> SEQUENCE: 182

Gln Val Gln Leu Val Gln Ser Gly Ala Glu Val Lys Lys Pro Gly Ala
                5                  10                  15

Ser Val Lys Val Ser Cys Lys Ile Ser Gly His Ser Leu Ser Glu Leu
            20                  25                  30

Ser Ile His Trp Val Arg Gln Thr Pro Thr Lys Gly Phe Glu Trp Met
        35                  40                  45

Gly Gly Phe Asp Pro Glu Glu Asn Glu Ile Val Tyr Ala Gln Arg Phe
    50                  55                  60

Gln Gly Arg Val Thr Met Thr Glu Asp Thr Ser Ile Asp Thr Ala Tyr
65                  70                  75                  80

Leu Thr Leu Ser Ser Leu Arg Ser Asp Asp Thr Ala Val Tyr Tyr Cys
                85                  90                  95

Ala Ile Val Gly Ser Val Ser Arg Ile Thr Tyr Gly Phe Trp Gly Lys
            100                 105                 110

Gly Thr Met Val Thr Val Ser Ser
        115                 120

<210> SEQ ID NO 183

<400> SEQUENCE: 183

000

<210> SEQ ID NO 184

<400> SEQUENCE: 184

000

<210> SEQ ID NO 185
<211> LENGTH: 11
<212> TYPE: PRT
<213> ORGANISM: Homo sapiens
<220> FEATURE:
<223> OTHER INFORMATION: Ab19

<400> SEQUENCE: 185

Val Gly Ser Val Ser Arg Ile Thr Tyr Gly Phe

<210> SEQ ID NO 186
<211> LENGTH: 339
<212> TYPE: DNA
<213> ORGANISM: Homo sapiens
<220> FEATURE:
<223> OTHER INFORMATION: Ab19

<400> SEQUENCE: 186
caggctgtgc tgactcagcc gtcctcagtg tctggggccc cagggcagag ggtcaccatc      60
tcctgtactg ggagcggctc caacatcggg gcaccttatg atgtaagctg gtaccagcag     120
cttccaggaa cagcccccaa actcctcatc tatcataaca acaagcggcc ctcagggggtc    180 cctgaccgat tctctgcctc caagtctggc acctcagcct ccctggccat cactgggctc     240
caggctgacg atgaggctga ttattactgc cagtcctatg acagccggaa ccccacgtc      300 atcttcgggg gagggaccaa gctcaccgtc ctaagtgcg                            339

<210> SEQ ID NO 187
<211> LENGTH: 113
<212> TYPE: PRT
<213> ORGANISM: Homo sapiens
<220> FEATURE:
<223> OTHER INFORMATION: Ab19

<400> SEQUENCE: 187

Gln Ala Val Leu Thr Gln Pro Ser Ser Val Ser Gly Ala Pro Gly Gln
                5                   10                  15
Arg Val Thr Ile Ser Cys Thr Gly Ser Gly Ser Asn Ile Gly Ala Pro
            20                  25                  30
Tyr Asp Val Ser Trp Tyr Gln Gln Leu Pro Gly Thr Ala Pro Lys Leu
        35                  40                  45
Leu Ile Tyr His Asn Asn Lys Arg Pro Ser Gly Val Pro Asp Arg Phe
    50                  55                  60
Ser Ala Ser Lys Ser Gly Thr Ser Ala Ser Leu Ala Ile Thr Gly Leu
65                  70                  75                  80
Gln Ala Asp Asp Glu Ala Asp Tyr Tyr Cys Gln Ser Tyr Asp Ser Arg
                85                  90                  95
Asn Pro His Val Ile Phe Gly Gly Gly Thr Lys Leu Thr Val Leu Ser
            100                 105                 110
Ala

<210> SEQ ID NO 188

<400> SEQUENCE: 188

000

<210> SEQ ID NO 189

<400> SEQUENCE: 189

000

<210> SEQ ID NO 190
<211> LENGTH: 11
<212> TYPE: PRT
<213> ORGANISM: Homo sapiens
<220> FEATURE:
<223> OTHER INFORMATION: Ab19

<400> SEQUENCE: 190

Gln Ser Tyr Asp Ser Arg Asn Pro His Val Ile
                5                   10

<210> SEQ ID NO 191
<211> LENGTH: 360
<212> TYPE: DNA
<213> ORGANISM: Homo sapiens
<220> FEATURE:
<223> OTHER INFORMATION: Ab20

<400> SEQUENCE: 191
caggtgcagc tggtgcaatc tggggctgag gtgaagaagc ctggggcctc agtgaaggtc    60
tcatgtaaaa tttccggaca cagcctcagt gaactgtcca tccactgggt gcgacagact   120
cccacaaaag gatttgagtg gatgggagga tttgatcctg aagagaatga aatagtctac   180
gcacagaggt tccagggcag agtcaccatg accgaggaca catctataga cacggcctac   240
ctgaccctga gcagcctgag atccgacgac acggccgttt attattgttc aatagtgggg   300
tctttcagtc ccctgacgct gggcctctgg ggcaaaggga caatggtcac cgtctcgagt   360

<210> SEQ ID NO 192
<211> LENGTH: 120
<212> TYPE: PRT
<213> ORGANISM: Homo sapiens
<220> FEATURE:
<223> OTHER INFORMATION: Ab20

<400> SEQUENCE: 192

Gln Val Gln Leu Val Gln Ser Gly Ala Glu Val Lys Lys Pro Gly Ala
                5                   10                  15

Ser Val Lys Val Ser Cys Lys Ile Ser Gly His Ser Leu Ser Glu Leu
            20                  25                  30

Ser Ile His Trp Val Arg Gln Thr Pro Thr Lys Gly Phe Glu Trp Met
        35                  40                  45

Gly Gly Phe Asp Pro Glu Glu Asn Glu Ile Val Tyr Ala Gln Arg Phe
    50                  55                  60

Gln Gly Arg Val Thr Met Thr Glu Asp Thr Ser Ile Asp Thr Ala Tyr
65                  70                  75                  80

Leu Thr Leu Ser Ser Leu Arg Ser Asp Asp Thr Ala Val Tyr Tyr Cys
                85                  90                  95

Ser Ile Val Gly Ser Phe Ser Pro Leu Thr Leu Gly Leu Trp Gly Lys
            100                 105                 110

Gly Thr Met Val Thr Val Ser Ser
        115                 120

<210> SEQ ID NO 193

<400> SEQUENCE: 193

000

<210> SEQ ID NO 194

<400> SEQUENCE: 194

000

<210> SEQ ID NO 195
<211> LENGTH: 11
<212> TYPE: PRT
<213> ORGANISM: Homo sapiens
<220> FEATURE:

<223> OTHER INFORMATION: Ab20

<400> SEQUENCE: 195

Val Gly Ser Phe Ser Pro Leu Thr Leu Gly Leu
              5                   10

<210> SEQ ID NO 196
<211> LENGTH: 339
<212> TYPE: DNA
<213> ORGANISM: Homo sapiens
<220> FEATURE:
<223> OTHER INFORMATION: Ab20

<400> SEQUENCE: 196
caggctgtgc tgactcagcc gtcctcagtg tctggggccc cagggcagag ggtcaccatc     60
tcctgtactg ggagcggctc caacatcggg gcaccttatg atgtaagctg gtaccagcag    120
cttccaggaa cagcccccaa actcctcatc tatcataaca acaagcggcc ctcaggggtc    180
cctgaccgat tctctgcctc caagtctggc acctcagcct ccctggccat cactgggctc    240
caggctgacg atgaggctga ttattactgc gcgaccgtgg acgaggccct gagtggttcg    300
gttttcggcg agggaccaa ggtcaccgtc ctaagtgcg                           339

<210> SEQ ID NO 197
<211> LENGTH: 113
<212> TYPE: PRT
<213> ORGANISM: Homo sapiens
<220> FEATURE:
<223> OTHER INFORMATION: Ab20

<400> SEQUENCE: 197

Gln Ala Val Leu Thr Gln Pro Ser Ser Val Ser Gly Ala Pro Gly Gln
              5                   10                  15

Arg Val Thr Ile Ser Cys Thr Gly Ser Gly Ser Asn Ile Gly Ala Pro
         20                  25                  30

Tyr Asp Val Ser Trp Tyr Gln Gln Leu Pro Gly Thr Ala Pro Lys Leu
     35                  40                  45

Leu Ile Tyr His Asn Asn Lys Arg Pro Ser Gly Val Pro Asp Arg Phe
 50                  55                  60

Ser Ala Ser Lys Ser Gly Thr Ser Ala Ser Leu Ala Ile Thr Gly Leu
65                  70                  75                  80

Gln Ala Asp Asp Glu Ala Asp Tyr Tyr Cys Ala Thr Val Asp Glu Ala
                 85                  90                  95

Leu Ser Gly Ser Val Phe Gly Gly Gly Thr Lys Val Thr Val Leu Ser
                100                 105                 110

Ala

<210> SEQ ID NO 198

<400> SEQUENCE: 198

000

<210> SEQ ID NO 199

<400> SEQUENCE: 199

000

<210> SEQ ID NO 200
<211> LENGTH: 11
<212> TYPE: PRT

```
<213> ORGANISM: Homo sapiens
<220> FEATURE:
<223> OTHER INFORMATION: Ab20

<400> SEQUENCE: 200

Ala Thr Val Asp Glu Ala Leu Ser Gly Ser Val
                5                  10

<210> SEQ ID NO 201
<211> LENGTH: 5
<212> TYPE: PRT
<213> ORGANISM: Homo sapiens

<400> SEQUENCE: 201

Tyr Leu Asp Phe Gln
                5

<210> SEQ ID NO 202
<211> LENGTH: 385
<212> TYPE: PRT
<213> ORGANISM: Homo sapiens

<400> SEQUENCE: 202

Met Leu Leu Leu Val Thr Ser Leu Leu Leu Cys Glu Leu Pro His Pro
1               5                  10                  15

Ala Phe Leu Leu Ile Pro Glu Lys Ser Asp Leu Arg Thr Val Ala Pro
            20                  25                  30

Ala Ser Ser Leu Asn Val Arg Phe Asp Ser Arg Thr Met Asn Leu Ser
        35                  40                  45

Trp Asp Cys Gln Glu Asn Thr Thr Phe Ser Lys Cys Phe Leu Thr Asp
    50                  55                  60

Lys Lys Asn Arg Val Val Glu Pro Arg Leu Ser Asn Asn Glu Cys Ser
65                  70                  75                  80

Cys Thr Phe Arg Glu Ile Cys Leu His Glu Gly Val Thr Phe Glu Val
                85                  90                  95

His Val Asn Thr Ser Gln Arg Gly Phe Gln Gln Lys Leu Leu Tyr Pro
            100                 105                 110

Asn Ser Gly Arg Glu Gly Thr Ala Ala Gln Asn Phe Ser Cys Phe Ile
        115                 120                 125

Tyr Asn Ala Asp Leu Met Asn Cys Thr Trp Ala Arg Gly Pro Thr Ala
    130                 135                 140

Pro Arg Asp Val Gln Tyr Phe Leu Tyr Ile Arg Asn Ser Lys Arg Arg
145                 150                 155                 160

Arg Glu Ile Arg Cys Pro Tyr Tyr Ile Gln Asp Ser Gly Thr His Val
                165                 170                 175

Gly Cys His Leu Asp Asn Leu Ser Gly Leu Thr Ser Arg Asn Tyr Phe
            180                 185                 190

Leu Val Asn Gly Thr Ser Arg Glu Ile Gly Ile Gln Phe Phe Asp Ser
        195                 200                 205

Leu Leu Asp Thr Lys Lys Ile Glu Arg Phe Asn Pro Pro Ser Asn Val
    210                 215                 220

Thr Val Arg Cys Asn Thr Thr His Cys Leu Val Arg Trp Lys Gln Pro
225                 230                 235                 240

Arg Thr Tyr Gln Lys Leu Ser Tyr Leu Asp Phe Gln Tyr Gln Leu Asp
                245                 250                 255

Val His Arg Lys Asn Thr Gln Pro Gly Thr Glu Asn Leu Leu Ile Asn
            260                 265                 270

Val Ser Gly Asp Leu Glu Asn Arg Tyr Asn Phe Pro Ser Ser Glu Pro
```

-continued

```
                275                 280                 285
Arg Ala Lys His Ser Val Lys Ile Arg Ala Ala Asp Val Arg Ile Leu
290                 295                 300
Asn Trp Ser Ser Trp Ser Glu Ala Ile Glu Phe Gly Ser Asp Asp Gly
305                 310                 315                 320
Asn Leu Gly Ser Val Tyr Ile Tyr Val Leu Ile Val Gly Thr Leu
                325                 330                 335
Val Cys Gly Ile Val Leu Gly Phe Leu Phe Lys Arg Phe Leu Arg Ile
                340                 345                 350
Gln Arg Leu Phe Pro Pro Val Pro Gln Ile Lys Asp Lys Leu Asn Asp
                355                 360                 365
Asn His Glu Val Glu Asp Glu Ile Ile Trp Glu Glu Phe Thr Pro Glu
                370                 375                 380
Glu
385

<210> SEQ ID NO 203
<211> LENGTH: 316
<212> TYPE: PRT
<213> ORGANISM: Homo Sapiens
<220> FEATURE:
<223> OTHER INFORMATION: Human sequence with FLAG tag

<400> SEQUENCE: 203

Ala Ser Ile Ser Ala Arg Gln Asp Tyr Lys Asp Asp Asp Lys Thr
1               5                   10                  15
Arg Gln Glu Lys Ser Asp Leu Arg Thr Val Ala Pro Ala Ser Ser Leu
                20                  25                  30
Asn Val Arg Phe Asp Ser Arg Thr Met Asn Leu Ser Trp Asp Cys Gln
                35                  40                  45
Glu Asn Thr Thr Phe Ser Lys Cys Phe Leu Thr Asp Lys Lys Asn Arg
50                  55                  60
Val Val Glu Pro Arg Leu Ser Asn Asn Glu Cys Ser Cys Thr Phe Arg
65                  70                  75                  80
Glu Ile Cys Leu His Glu Gly Val Thr Phe Glu Val His Val Asn Thr
                85                  90                  95
Ser Gln Arg Gly Phe Gln Gln Lys Leu Leu Tyr Pro Asn Ser Gly Arg
                100                 105                 110
Glu Gly Thr Ala Ala Gln Asn Phe Ser Cys Phe Ile Tyr Asn Ala Asp
                115                 120                 125
Leu Met Asn Cys Thr Trp Ala Arg Gly Pro Thr Ala Pro Arg Asp Val
130                 135                 140
Gln Tyr Phe Leu Tyr Ile Arg Asn Ser Lys Arg Arg Arg Glu Ile Arg
145                 150                 155                 160
Cys Pro Tyr Tyr Ile Gln Asp Ser Gly Thr His Val Gly Cys His Leu
                165                 170                 175
Asp Asn Leu Ser Gly Leu Thr Ser Arg Asn Tyr Phe Leu Val Asn Gly
                180                 185                 190
Thr Ser Arg Glu Ile Gly Ile Gln Phe Phe Asp Ser Leu Leu Asp Thr
                195                 200                 205
Lys Lys Ile Glu Arg Phe Asn Pro Pro Ser Asn Val Thr Val Arg Cys
                210                 215                 220
Asn Thr Thr His Cys Leu Val Arg Trp Lys Gln Pro Arg Thr Tyr Gln
225                 230                 235                 240
Lys Leu Ser Tyr Leu Asp Phe Gln Tyr Gln Leu Asp Val His Arg Lys
                245                 250                 255
```

```
Asn Thr Gln Pro Gly Thr Glu Asn Leu Leu Ile Asn Val Ser Gly Asp
            260                 265                 270

Leu Glu Asn Arg Tyr Asn Phe Pro Ser Ser Glu Pro Arg Ala Lys His
        275                 280                 285

Ser Val Lys Ile Arg Ala Ala Asp Val Arg Ile Leu Asn Trp Ser Ser
290                 295                 300

Trp Ser Glu Ala Ile Glu Phe Gly Ser Asp Asp Gly
305                 310                 315

<210> SEQ ID NO 204
<211> LENGTH: 8
<212> TYPE: PRT
<213> ORGANISM: Artificial
<220> FEATURE:
<223> OTHER INFORMATION: Synthetic FLAG peptide

<400> SEQUENCE: 204

Asp Tyr Lys Asp Asp Asp Asp Lys
1               5

<210> SEQ ID NO 205
<211> LENGTH: 298
<212> TYPE: PRT
<213> ORGANISM: Homo sapiens

<400> SEQUENCE: 205

Glu Lys Ser Asp Leu Arg Thr Val Ala Pro Ala Ser Ser Leu Asn Val
1               5                   10                  15

Arg Phe Asp Ser Arg Thr Met Asn Leu Ser Trp Asp Cys Gln Glu Asn
            20                  25                  30

Thr Thr Phe Ser Lys Cys Phe Leu Thr Asp Lys Lys Asn Arg Val Val
        35                  40                  45

Glu Pro Arg Leu Ser Asn Asn Glu Cys Ser Cys Thr Phe Arg Glu Ile
    50                  55                  60

Cys Leu His Glu Gly Val Thr Phe Glu Val His Val Asn Thr Ser Gln
65                  70                  75                  80

Arg Gly Phe Gln Gln Lys Leu Leu Tyr Pro Asn Ser Gly Arg Glu Gly
                85                  90                  95

Thr Ala Ala Gln Asn Phe Ser Cys Phe Ile Tyr Asn Ala Asp Leu Met
            100                 105                 110

Asn Cys Thr Trp Ala Arg Gly Pro Thr Ala Pro Arg Asp Val Gln Tyr
        115                 120                 125

Phe Leu Tyr Ile Arg Asn Ser Lys Arg Arg Arg Glu Ile Arg Cys Pro
    130                 135                 140

Tyr Tyr Ile Gln Asp Ser Gly Thr His Val Gly Cys His Leu Asp Asn
145                 150                 155                 160

Leu Ser Gly Leu Thr Ser Arg Asn Tyr Phe Leu Val Asn Gly Thr Ser
                165                 170                 175

Arg Glu Ile Gly Ile Gln Phe Phe Asp Ser Leu Leu Asp Thr Lys Lys
            180                 185                 190

Ile Glu Arg Phe Asn Pro Pro Ser Asn Val Thr Val Arg Cys Asn Thr
        195                 200                 205

Thr His Cys Leu Val Arg Trp Lys Gln Pro Arg Thr Tyr Gln Lys Leu
    210                 215                 220

Ser Tyr Leu Asp Phe Gln Tyr Gln Leu Asp Val His Arg Lys Asn Thr
225                 230                 235                 240

Gln Pro Gly Thr Glu Asn Leu Leu Ile Asn Val Ser Gly Asp Leu Glu
```

-continued

```
                245                 250                 255
Asn Arg Tyr Asn Phe Pro Ser Ser Glu Pro Arg Ala Lys His Ser Val
            260                 265                 270

Lys Ile Arg Ala Ala Asp Val Arg Ile Leu Asn Trp Ser Ser Trp Ser
            275                 280                 285

Glu Ala Ile Glu Phe Gly Ser Asp Gly
            290                 295

<210> SEQ ID NO 206
<211> LENGTH: 378
<212> TYPE: PRT
<213> ORGANISM: Homo sapiens

<400> SEQUENCE: 206

Glu Lys Ser Asp Leu Arg Thr Val Ala Pro Ala Ser Ser Leu Asn Val
1               5                   10                  15

Arg Phe Asp Ser Arg Thr Met Asn Leu Ser Trp Asp Cys Gln Glu Asn
            20                  25                  30

Thr Thr Phe Ser Lys Cys Phe Leu Thr Asp Lys Lys Asn Arg Val Val
            35                  40                  45

Glu Pro Arg Leu Ser Asn Asn Glu Cys Ser Cys Thr Phe Arg Glu Ile
        50                  55                  60

Cys Leu His Glu Gly Val Thr Phe Glu Val His Val Asn Thr Ser Gln
65                  70                  75                  80

Arg Gly Phe Gln Gln Lys Leu Leu Tyr Pro Asn Ser Gly Arg Glu Gly
                85                  90                  95

Thr Ala Ala Gln Asn Phe Ser Cys Phe Ile Tyr Asn Ala Asp Leu Met
            100                 105                 110

Asn Cys Thr Trp Ala Arg Gly Pro Thr Ala Pro Arg Asp Val Gln Tyr
            115                 120                 125

Phe Leu Tyr Ile Arg Asn Ser Lys Arg Arg Glu Ile Arg Cys Pro
        130                 135                 140

Tyr Tyr Ile Gln Asp Ser Gly Thr His Val Gly Cys His Leu Asp Asn
145                 150                 155                 160

Leu Ser Gly Leu Thr Ser Arg Asn Tyr Phe Leu Val Asn Gly Thr Ser
                165                 170                 175

Arg Glu Ile Gly Ile Gln Phe Phe Asp Ser Leu Leu Asp Thr Lys Lys
            180                 185                 190

Ile Glu Arg Phe Asn Pro Pro Ser Asn Val Thr Val Arg Cys Asn Thr
            195                 200                 205

Thr His Cys Leu Val Arg Trp Lys Gln Pro Arg Thr Tyr Gln Lys Leu
        210                 215                 220

Ser Tyr Leu Asp Phe Gln Tyr Gln Leu Asp Val His Arg Lys Asn Thr
225                 230                 235                 240

Gln Pro Gly Thr Glu Asn Leu Leu Ile Asn Val Ser Gly Asp Leu Glu
                245                 250                 255

Asn Arg Tyr Asn Phe Pro Ser Ser Glu Pro Arg Ala Lys His Ser Val
            260                 265                 270

Lys Ile Arg Ala Ala Asp Val Arg Ile Leu Asn Trp Ser Ser Trp Ser
            275                 280                 285

Glu Ala Ile Glu Phe Gly Ser Asp Gly Asn Leu Gly Ser Val Tyr
            290                 295                 300

Ile Tyr Val Leu Leu Ile Val Gly Thr Leu Val Cys Gly Ile Val Leu
305                 310                 315                 320

Gly Phe Leu Phe Lys Arg Phe Leu Arg Ile Gln Arg Leu Phe Pro Pro
```

```
                    325                 330                 335
Val Pro Gln Ile Lys Asp Lys Leu Asn Asp Asn His Glu Val Glu Asp
                340                 345                 350

Glu Ile Ile Trp Glu Glu Phe Thr Pro Glu Glu Gly Lys Gly Tyr Arg
            355                 360                 365

Glu Glu Val Leu Thr Val Lys Glu Ile Thr
        370                 375

<210> SEQ ID NO 207
<211> LENGTH: 333
<212> TYPE: DNA
<213> ORGANISM: Homo sapiens
<220> FEATURE:
<223> OTHER INFORMATION: Ab1

<400> SEQUENCE: 207
cagtctgtgc tgactcagcc gccctcagtg tctggggccc cagggcagag ggtcaccatc    60
tcctgtactg ggagcggctc caacatcggg gcacccttatg atgtaagctg gtaccagcag   120
cttccaggaa cagcccccaa actcctcatc tatcataaca acaagcggcc ctcaggggtc   180
cctgaccgat tctctggctc caagtctggc acctcagcct ccctggccat cactgggctc   240
caggctgagg atgaggctga ttattactgc cagtcctatg acagcagctc gatcagcacg   300
attttcggcg gagggaccaa gctcaccgtc cta                                333

<210> SEQ ID NO 208
<211> LENGTH: 111
<212> TYPE: PRT
<213> ORGANISM: Homo sapiens
<220> FEATURE:
<223> OTHER INFORMATION: Ab1

<400> SEQUENCE: 208

Gln Ser Val Leu Thr Gln Pro Pro Ser Val Ser Gly Ala Pro Gly Gln
                5                   10                  15

Arg Val Thr Ile Ser Cys Thr Gly Ser Gly Ser Asn Ile Gly Ala Pro
            20                  25                  30

Tyr Asp Val Ser Trp Tyr Gln Gln Leu Pro Gly Thr Ala Pro Lys Leu
        35                  40                  45

Leu Ile Tyr His Asn Asn Lys Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95

Ser Ile Ser Thr Ile Phe Gly Gly Gly Thr Lys Leu Thr Val Leu
            100                 105                 110

<210> SEQ ID NO 209
<211> LENGTH: 333
<212> TYPE: DNA
<213> ORGANISM: Homo sapiens
<220> FEATURE:
<223> OTHER INFORMATION: Ab2

<400> SEQUENCE: 209
caggctgtgc tgactcagcc gtcctcagtg tctggggccc cagggcagag ggtcaccatc    60
tcctgtactg ggagcggctc caacatcggg gcacccttatg atgtaagctg gtaccagcag   120
cttccaggaa cagcccccaa actcctcatc tatcataaca acaagcggcc ctcaggggtc   180
```

```
cctgaccgat tctctgcctc caagtctggc acctcagcct ccctggccat cactgggctc    240
caggctgacg atgaggctga ttattactgc cagtcctatg acagcagcct gagtggttcg    300
gttttcggcg agggaccaa ggtcaccgtc cta                                   333
```

<210> SEQ ID NO 210
<211> LENGTH: 111
<212> TYPE: PRT
<213> ORGANISM: Homo sapiens
<220> FEATURE:
<223> OTHER INFORMATION: Ab2

<400> SEQUENCE: 210

```
Gln Ala Val Leu Thr Gln Pro Ser Ser Val Ser Gly Ala Pro Gly Gln
                5                  10                  15
Arg Val Thr Ile Ser Cys Thr Gly Ser Gly Ser Asn Ile Gly Ala Pro
            20                  25                  30
Tyr Asp Val Ser Trp Tyr Gln Gln Leu Pro Gly Thr Ala Pro Lys Leu
        35                  40                  45
Leu Ile Tyr His Asn Asn Lys Arg Pro Ser Gly Val Pro Asp Arg Phe
    50                  55                  60
Ser Ala Ser Lys Ser Gly Thr Ser Ala Ser Leu Ala Ile Thr Gly Leu
65                  70                  75                  80
Gln Ala Asp Asp Glu Ala Asp Tyr Tyr Cys Gln Ser Tyr Asp Ser Ser
                85                  90                  95
Leu Ser Gly Ser Val Phe Gly Gly Gly Thr Lys Val Thr Val Leu
            100                 105                 110
```

<210> SEQ ID NO 211
<211> LENGTH: 333
<212> TYPE: DNA
<213> ORGANISM: Homo sapiens
<220> FEATURE:
<223> OTHER INFORMATION: Ab3

<400> SEQUENCE: 211

```
caggctgtgc tgactcagcc gtcctcagtg tctggggccc cagggcagag ggtcaccatc     60
tcctgtactg ggagcggctc caacatcggg gcaccttatg atgtaagctg gtaccagcag    120
cttccaggaa cagcccccaa actcctcatc tatcataaca acaagcggcc ctcaggggtc    180
cctgaccgat tctctgcctc caagtctggc acctcagcct ccctggccat cactgggctc    240
caggctgacg atgaggctga ttattactgc cagtcctatg acagcagcct gagtggttcg    300
gttttcgggg agggaccaa ggtcaccgtc cta                                   333
```

<210> SEQ ID NO 212

<400> SEQUENCE: 212

000

<210> SEQ ID NO 213

<400> SEQUENCE: 213

000

<210> SEQ ID NO 214

<400> SEQUENCE: 214

000

<210> SEQ ID NO 215

<400> SEQUENCE: 215

000

<210> SEQ ID NO 216

<400> SEQUENCE: 216

000

<210> SEQ ID NO 217
<211> LENGTH: 333
<212> TYPE: DNA
<213> ORGANISM: Homo sapiens
<220> FEATURE:
<223> OTHER INFORMATION: Ab6

<400> SEQUENCE: 217

```
cagtctgtgc tgactcagcc gccctcagtg tctggggccc cagggcagag ggtcaccatc      60
tcctgtactg ggagcggctc aacatcggg gcaccttatg atgtaagctg gtaccagcag     120
cttccaggaa cagcccccaa actcctcatc tatcataaca acaagcggcc ctcagggggtc    180 cctgaccgat tctctggctc caagtctggc acctcagcct ccctggccat cactgggctc    240
caggctgagg atgaggctga ttattactgc gcgaccgttg aggccggcct gagtggttcg    300
gttttcggcg gagggaccaa gctgaccgtc cta                                 333
```

<210> SEQ ID NO 218
<211> LENGTH: 111
<212> TYPE: PRT
<213> ORGANISM: Homo sapiens
<220> FEATURE:
<223> OTHER INFORMATION: Ab6

<400> SEQUENCE: 218

```
Gln Ser Val Leu Thr Gln Pro Pro Ser Val Ser Gly Ala Pro Gly Gln
              5                   10                  15
Arg Val Thr Ile Ser Cys Thr Gly Ser Gly Ser Asn Ile Gly Ala Pro
         20                   25                  30
Tyr Asp Val Ser Trp Tyr Gln Gln Leu Pro Gly Thr Ala Pro Lys Leu
     35                   40                  45
Leu Ile Tyr His Asn Asn Lys Arg Pro Ser Gly Val Pro Asp Arg Phe
 50                   55                  60
Ser Gly Ser Lys Ser Gly Thr Ser Ala Ser Leu Ala Ile Thr Gly Leu
65                   70                  75                  80
Gln Ala Glu Asp Glu Ala Asp Tyr Tyr Cys Ala Thr Val Glu Ala Gly
                 85                   90                  95
Leu Ser Gly Ser Val Phe Gly Gly Gly Thr Lys Leu Thr Val Leu
            100                  105                 110
```

<210> SEQ ID NO 219

<400> SEQUENCE: 219

000

<210> SEQ ID NO 220

<400> SEQUENCE: 220

000

<210> SEQ ID NO 221

<400> SEQUENCE: 221

000

<210> SEQ ID NO 222

<400> SEQUENCE: 222

000

<210> SEQ ID NO 223

<400> SEQUENCE: 223

000

<210> SEQ ID NO 224

<400> SEQUENCE: 224

000

<210> SEQ ID NO 225

<400> SEQUENCE: 225

000

<210> SEQ ID NO 226

<400> SEQUENCE: 226

000

<210> SEQ ID NO 227
<211> LENGTH: 333
<212> TYPE: DNA
<213> ORGANISM: Homo sapiens
<220> FEATURE:
<223> OTHER INFORMATION: Ab11

<400> SEQUENCE: 227

```
caggctgtgc tgactcagcc gtcctcagtg tctggggtcc cagggcagag ggtcaccatc     60
tcctgtactg ggagcggctc caacatcggg gcaccttatg atgtaagctg gtaccagcag    120
cttccaggaa cagcccccaa actcctcatc tatcataaca acaagcggcc ctcagggtc    180
cctgaccgat tctctgcctc caagtctggc acctcagcct ccctggccat cactgggctc    240
caggctgacg atgaggctga ttattactgc cagtcctatg acagcagcct gagtggttcg    300
gttttcggcg gagggaccaa ggtcaccgtc cta                                  333
```

<210> SEQ ID NO 228
<211> LENGTH: 111
<212> TYPE: PRT
<213> ORGANISM: Homo sapiens
<220> FEATURE:
<223> OTHER INFORMATION: Ab11

<400> SEQUENCE: 228

Gln Ala Val Leu Thr Gln Pro Ser Ser Val Ser Gly Val Pro Gly Gln
                5                  10                  15
Arg Val Thr Ile Ser Cys Thr Gly Ser Gly Ser Asn Ile Gly Ala Pro
            20                  25                  30

Tyr Asp Val Ser Trp Tyr Gln Gln Leu Pro Gly Thr Ala Pro Lys Leu
                35                  40                  45

Leu Ile Tyr His Asn Asn Lys Arg Pro Ser Gly Val Pro Asp Arg Phe
 50                  55                  60

Ser Ala Ser Lys Ser Gly Thr Ser Ala Ser Leu Ala Ile Thr Gly Leu
 65                  70                  75                  80

Gln Ala Asp Asp Glu Ala Asp Tyr Tyr Cys Gln Ser Tyr Asp Ser Ser
                 85                  90                  95

Leu Ser Gly Ser Val Phe Gly Gly Gly Thr Lys Val Thr Val Leu
                100                 105                 110

<210> SEQ ID NO 229
<211> LENGTH: 333
<212> TYPE: DNA
<213> ORGANISM: Homo sapiens
<220> FEATURE:
<223> OTHER INFORMATION: Ab12

<400> SEQUENCE: 229
caggctgtgc tgactcagcc gtcctcagtg tctggggccc cagggcagag ggtcaccatc      60
tcctgtactg ggagcggctc aaacatcggg gcaccttatg atgtaagctg gtaccagcag     120
cttccaggaa cagcccccaa actcctcatc tatcataaca acaagcggcc ctcaggggtc     180
cctgaccgat tctctgcctc caagtctggc acctcagcct ccctggccat cactgggctc     240
caggctgacg atgaggctga ttattactgc cagtcctatg acagcagcc gaccgagatc      300 cgcttcgggg gagggaccaa gctcaccgtc cta                                  333

<210> SEQ ID NO 230
<211> LENGTH: 111
<212> TYPE: PRT
<213> ORGANISM: Homo sapiens
<220> FEATURE:
<223> OTHER INFORMATION: Ab12

<400> SEQUENCE: 230

Gln Ala Val Leu Thr Gln Pro Ser Ser Val Ser Gly Ala Pro Gly Gln
                 5                  10                  15

Arg Val Thr Ile Ser Cys Thr Gly Ser Gly Ser Asn Ile Gly Ala Pro
                20                  25                  30

Tyr Asp Val Ser Trp Tyr Gln Gln Leu Pro Gly Thr Ala Pro Lys Leu
                35                  40                  45

Leu Ile Tyr His Asn Asn Lys Arg Pro Ser Gly Val Pro Asp Arg Phe
 50                  55                  60

Ser Ala Ser Lys Ser Gly Thr Ser Ala Ser Leu Ala Ile Thr Gly Leu
 65                  70                  75                  80

Gln Ala Asp Asp Glu Ala Asp Tyr Tyr Cys Gln Ser Tyr Asp Ser Glu
                 85                  90                  95

Pro Thr Glu Ile Arg Phe Gly Gly Gly Thr Lys Leu Thr Val Leu
                100                 105                 110

<210> SEQ ID NO 231
<211> LENGTH: 333
<212> TYPE: DNA
<213> ORGANISM: Homo sapiens
<220> FEATURE:
<223> OTHER INFORMATION: Ab13

<400> SEQUENCE: 231
caggctgtgc tgactcagcc gtcctcagtg tctggggccc cagggcagag ggtcaccatc      60

```
tcctgtactg ggagcggctc aacatcggg gcaccttatg atgtaagctg gtaccagcag      120
cttccaggaa cagcccccaa actcctcatc tatcataaca acaagcggcc ctcaggggtc      180
cctgaccgat tctctgcctc caagtctggc acctcagcct ccctggccat cactgggctc      240
caggctgacg atgaggctga ttattactgc cagtcctatg acagcaggac gggcatcatc      300
gtcttcgggg gagggaccaa ggtcaccgtc cta                                  333
```

<210> SEQ ID NO 232
<211> LENGTH: 111
<212> TYPE: PRT
<213> ORGANISM: Homo sapiens
<220> FEATURE:
<223> OTHER INFORMATION: Ab13

<400> SEQUENCE: 232

```
Gln Ala Val Leu Thr Gln Pro Ser Ser Val Ser Gly Ala Pro Gly Gln
              5                  10                  15

Arg Val Thr Ile Ser Cys Thr Gly Ser Gly Ser Asn Ile Gly Ala Pro
         20                  25                  30

Tyr Asp Val Ser Trp Tyr Gln Gln Leu Pro Gly Thr Ala Pro Lys Leu
     35                  40                  45

Leu Ile Tyr His Asn Asn Lys Arg Pro Ser Gly Val Pro Asp Arg Phe
 50                  55                  60

Ser Ala Ser Lys Ser Gly Thr Ser Ala Ser Leu Ala Ile Thr Gly Leu
65                  70                  75                  80

Gln Ala Asp Asp Glu Ala Asp Tyr Tyr Cys Gln Ser Tyr Asp Ser Arg
                 85                  90                  95

Thr Gly Ile Ile Val Phe Gly Gly Gly Thr Lys Val Thr Val Leu
            100                 105                 110
```

<210> SEQ ID NO 233
<211> LENGTH: 333
<212> TYPE: DNA
<213> ORGANISM: Homo sapiens
<220> FEATURE:
<223> OTHER INFORMATION: Ab14

<400> SEQUENCE: 233

```
caggctgtgc tgactcagcc gtcctcagtg tctggggccc cagggcagag ggtcaccatc      60
tcctgtactg ggagcggctc aacatcggg gcaccttatg atgtaagctg gtaccagcag      120
cttccaggaa cagcccccaa actcctcatc tatcataaca acaagcggcc ctcaggggtc      180
cctgaccgat tctctgcctc caagtctggc acctcagcct ccctggccat cactgggctc      240
caggctgacg atgaggctga ttattactgc cagtcctatg acagcgagga caggatgacg      300
gagttcgggg gagggaccaa ggtcaccgtc cta                                  333
```

<210> SEQ ID NO 234
<211> LENGTH: 111
<212> TYPE: PRT
<213> ORGANISM: Homo sapiens
<220> FEATURE:
<223> OTHER INFORMATION: Ab14

<400> SEQUENCE: 234

```
Gln Ala Val Leu Thr Gln Pro Ser Ser Val Ser Gly Ala Pro Gly Gln
              5                  10                  15

Arg Val Thr Ile Ser Cys Thr Gly Ser Gly Ser Asn Ile Gly Ala Pro
         20                  25                  30
```

Tyr Asp Val Ser Trp Tyr Gln Gln Leu Pro Gly Thr Ala Pro Lys Leu
                35                  40                  45

Leu Ile Tyr His Asn Asn Lys Arg Pro Ser Gly Val Pro Asp Arg Phe
    50                  55                  60

Ser Ala Ser Lys Ser Gly Thr Ser Ala Ser Leu Ala Ile Thr Gly Leu
65                  70                  75                  80

Gln Ala Asp Asp Glu Ala Asp Tyr Tyr Cys Gln Ser Tyr Asp Ser Glu
                85                  90                  95

Asp Arg Met Thr Glu Phe Gly Gly Thr Lys Val Thr Val Leu
            100                 105                 110

<210> SEQ ID NO 235
<211> LENGTH: 333
<212> TYPE: DNA
<213> ORGANISM: Homo sapiens
<220> FEATURE:
<223> OTHER INFORMATION: Ab15

<400> SEQUENCE: 235
caggctgtgc tgactcagcc gtcctcagtg tctggggccc cagggcagag ggtcaccatc       60
tcctgtactg ggagcggctc aacatcggg gcaccttatg atgtaagctg gtaccagcag      120
cttccaggaa cagcccccaa actcctcatc tatcataaca acaagcggcc ctcaggggtc      180
cctgaccgat tctctgcctc caagtctggc acctcagcct ccctggccat cactgggctc      240
caggctgacg atgaggctga ttattactgc cagtcctatg acagccagtt gattagcgcc      300
gccttcgggg agggaccaa ggtcaccgtc cta                                    333

<210> SEQ ID NO 236
<211> LENGTH: 111
<212> TYPE: PRT
<213> ORGANISM: Homo sapiens
<220> FEATURE:
<223> OTHER INFORMATION: Ab15

<400> SEQUENCE: 236

Gln Ala Val Leu Thr Gln Pro Ser Ser Val Ser Gly Ala Pro Gly Gln
                5                   10                  15

Arg Val Thr Ile Ser Cys Thr Gly Ser Gly Ser Asn Ile Gly Ala Pro
            20                  25                  30

Tyr Asp Val Ser Trp Tyr Gln Gln Leu Pro Gly Thr Ala Pro Lys Leu
                35                  40                  45

Leu Ile Tyr His Asn Asn Lys Arg Pro Ser Gly Val Pro Asp Arg Phe
    50                  55                  60

Ser Ala Ser Lys Ser Gly Thr Ser Ala Ser Leu Ala Ile Thr Gly Leu
65                  70                  75                  80

Gln Ala Asp Asp Glu Ala Asp Tyr Tyr Cys Gln Ser Tyr Asp Ser Gln
                85                  90                  95

Leu Ile Ser Ala Ala Phe Gly Gly Gly Thr Lys Val Thr Val Leu
            100                 105                 110

<210> SEQ ID NO 237
<211> LENGTH: 333
<212> TYPE: DNA
<213> ORGANISM: Homo sapiens
<220> FEATURE:
<223> OTHER INFORMATION: Ab16

<400> SEQUENCE: 237
caggctgtgc tgactcagcc gtcctcagtg tctggggccc cagggcagag ggtcaccatc       60

```
tcctgtactg ggagcggctc caacatcggg gcaccttatg atgtaagctg gtaccagcag    120
cttccaggaa cagcccccaa actcctcatc tatcataaca acaagcggcc ctcagggggtc   180 cctgaccgat tctctgcctc caagtctggc acctcagcct ccctggccat cactgggctc    240
caggctgagg atgaggctga ttattactgc gcgacctccg acgagatcct gagtggttcg    300
gttttcgggg gagggaccaa ggtcaccgtc cta                                 333
```

<210> SEQ ID NO 238
<211> LENGTH: 111
<212> TYPE: PRT
<213> ORGANISM: Homo sapiens
<220> FEATURE:
<223> OTHER INFORMATION: Ab16

<400> SEQUENCE: 238

Gln Ala Val Leu Thr Gln Pro Ser Ser Val Ser Gly Ala Pro Gly Gln
              5                  10                  15
Arg Val Thr Ile Ser Cys Thr Gly Ser Gly Ser Asn Ile Gly Ala Pro
         20                  25                  30
Tyr Asp Val Ser Trp Tyr Gln Gln Leu Pro Gly Thr Ala Pro Lys Leu
     35                  40                  45
Leu Ile Tyr His Asn Asn Lys Arg Pro Ser Gly Val Pro Asp Arg Phe
 50                  55                  60
Ser Ala Ser Lys Ser Gly Thr Ser Ala Ser Leu Ala Ile Thr Gly Leu
65                  70                  75                  80
Gln Ala Glu Asp Glu Ala Asp Tyr Tyr Cys Ala Thr Ser Asp Glu Ile
                 85                  90                  95
Leu Ser Gly Ser Val Phe Gly Gly Gly Thr Lys Val Thr Val Leu
            100                 105                 110

<210> SEQ ID NO 239
<211> LENGTH: 333
<212> TYPE: DNA
<213> ORGANISM: Homo sapiens
<220> FEATURE:
<223> OTHER INFORMATION: Ab17

<400> SEQUENCE: 239

```
caggctgtgc tgactcagcc gtcctcagtg tctggggccc cagggcagag ggtcaccatc    60
tcctgtactg ggagcggctc caacatcggg gcaccttatg atgtaagctg gtaccagcag    120
cttccaggaa cagcccccaa actcctcatc tatcataaca acaagcggcc ctcagggggtc   180 cctgaccgat tctctgcctc caagtctggc acctcagcct ccctggccat cactgggctc    240
caggctgacg atgaggctga ttattactgc gcgaccgtcg aggacggcct gagtggttcg    300
gttttcgggg gagggaccaa ggtcaccgtc cta                                 333
```

<210> SEQ ID NO 240
<211> LENGTH: 111
<212> TYPE: PRT
<213> ORGANISM: Homo sapiens
<220> FEATURE:
<223> OTHER INFORMATION: Ab17

<400> SEQUENCE: 240

Gln Ala Val Leu Thr Gln Pro Ser Ser Val Ser Gly Ala Pro Gly Gln
              5                  10                  15
Arg Val Thr Ile Ser Cys Thr Gly Ser Gly Ser Asn Ile Gly Ala Pro
         20                  25                  30
Tyr Asp Val Ser Trp Tyr Gln Gln Leu Pro Gly Thr Ala Pro Lys Leu

```
                35                  40                  45
Leu Ile Tyr His Asn Asn Lys Arg Pro Ser Gly Val Pro Asp Arg Phe
 50                  55                  60

Ser Ala Ser Lys Ser Gly Thr Ser Ala Ser Leu Ala Ile Thr Gly Leu
 65                  70                  75                  80

Gln Ala Asp Asp Glu Ala Asp Tyr Tyr Cys Ala Thr Val Glu Asp Gly
                 85                  90                  95

Leu Ser Gly Ser Val Phe Gly Gly Gly Thr Lys Val Thr Val Leu
                100                 105                 110

<210> SEQ ID NO 241
<211> LENGTH: 333
<212> TYPE: DNA
<213> ORGANISM: Homo sapiens
<220> FEATURE:
<223> OTHER INFORMATION: Ab18

<400> SEQUENCE: 241
caggctgtgc tgactcagcc gtcctcagtg tctggggccc cagggcagag ggtcaccatc      60
tcctgtactg ggagcggctc caacatcggg gcaccttatg atgtaagctg gtaccagcag     120
cttccaggaa cagcccccaa actcctcatc tatcataaca acaagcggcc ctcaggggtc     180
cctgaccgat tctctgcctc caagtctggc acctcagcct ccctggccat cactgggctc     240
caggctgacg atgaggctga ttattactgc cagtcctatg acagccagtg gaaccagccc     300
ctcttcgggg gagggaccaa ggtcaccgtc cta                                  333

<210> SEQ ID NO 242
<211> LENGTH: 111
<212> TYPE: PRT
<213> ORGANISM: Homo sapiens
<220> FEATURE:
<223> OTHER INFORMATION: Ab18

<400> SEQUENCE: 242

Gln Ala Val Leu Thr Gln Pro Ser Ser Val Ser Gly Ala Pro Gly Gln
                 5                  10                  15

Arg Val Thr Ile Ser Cys Thr Gly Ser Gly Ser Asn Ile Gly Ala Pro
             20                  25                  30

Tyr Asp Val Ser Trp Tyr Gln Gln Leu Pro Gly Thr Ala Pro Lys Leu
         35                  40                  45

Leu Ile Tyr His Asn Asn Lys Arg Pro Ser Gly Val Pro Asp Arg Phe
 50                  55                  60

Ser Ala Ser Lys Ser Gly Thr Ser Ala Ser Leu Ala Ile Thr Gly Leu
 65                  70                  75                  80

Gln Ala Asp Asp Glu Ala Asp Tyr Tyr Cys Gln Ser Tyr Asp Ser Gln
                 85                  90                  95

Trp Asn Gln Pro Leu Phe Gly Gly Gly Thr Lys Val Thr Val Leu
                100                 105                 110

<210> SEQ ID NO 243
<211> LENGTH: 333
<212> TYPE: DNA
<213> ORGANISM: Homo sapiens
<220> FEATURE:
<223> OTHER INFORMATION: Ab19

<400> SEQUENCE: 243
caggctgtgc tgactcagcc gtcctcagtg tctggggccc cagggcagag ggtcaccatc      60
tcctgtactg ggagcggctc caacatcggg gcaccttatg atgtaagctg gtaccagcag     120
```

```
cttccaggaa cagcccccaa actcctcatc tatcataaca acaagcggcc ctcaggggtc      180
cctgaccgat tctctgcctc caagtctggc acctcagcct ccctggccat cactgggctc      240
caggctgacg atgaggctga ttattactgc cagtcctatg acagccggaa ccccacgtc       300 atcttcgggg gagggaccaa gctcaccgtc cta                                    333
```

<210> SEQ ID NO 244
<211> LENGTH: 111
<212> TYPE: PRT
<213> ORGANISM: Homo sapiens
<220> FEATURE:
<223> OTHER INFORMATION: Ab19

<400> SEQUENCE: 244

Gln Ala Val Leu Thr Gln Pro Ser Ser Val Ser Gly Ala Pro Gly Gln
                5                   10                  15

Arg Val Thr Ile Ser Cys Thr Gly Ser Gly Ser Asn Ile Gly Ala Pro
            20                  25                  30

Tyr Asp Val Ser Trp Tyr Gln Gln Leu Pro Gly Thr Ala Pro Lys Leu
        35                  40                  45

Leu Ile Tyr His Asn Asn Lys Arg Pro Ser Gly Val Pro Asp Arg Phe
    50                  55                  60

Ser Ala Ser Lys Ser Gly Thr Ser Ala Ser Leu Ala Ile Thr Gly Leu
65                  70                  75                  80

Gln Ala Asp Asp Glu Ala Asp Tyr Tyr Cys Gln Ser Tyr Asp Ser Arg
                85                  90                  95

Asn Pro His Val Ile Phe Gly Gly Gly Thr Lys Leu Thr Val Leu
            100                 105                 110

<210> SEQ ID NO 245
<211> LENGTH: 333
<212> TYPE: DNA
<213> ORGANISM: Homo sapiens
<220> FEATURE:
<223> OTHER INFORMATION: Ab20

<400> SEQUENCE: 245

```
caggctgtgc tgactcagcc gtcctcagtg tctggggccc agggcagag ggtcaccatc        60 tcctgtactg ggagcggctc caacatcggg gcaccttatg atgtaagctg gtaccagcag      120
cttccaggaa cagcccccaa actcctcatc tatcataaca acaagcggcc ctcaggggtc      180
cctgaccgat tctctgcctc caagtctggc acctcagcct ccctggccat cactgggctc      240
caggctgacg atgaggctga ttattactgc gcgaccgtgg acgaggccct gagtggttcg      300
gttttcggcg gagggaccaa ggtcaccgtc cta                                    333
```

<210> SEQ ID NO 246
<211> LENGTH: 111
<212> TYPE: PRT
<213> ORGANISM: Homo sapiens
<220> FEATURE:
<223> OTHER INFORMATION: Ab20

<400> SEQUENCE: 246

Gln Ala Val Leu Thr Gln Pro Ser Ser Val Ser Gly Ala Pro Gly Gln
                5                   10                  15

Arg Val Thr Ile Ser Cys Thr Gly Ser Gly Ser Asn Ile Gly Ala Pro
            20                  25                  30

Tyr Asp Val Ser Trp Tyr Gln Gln Leu Pro Gly Thr Ala Pro Lys Leu
        35                  40                  45

Leu Ile Tyr His Asn Asn Lys Arg Pro Ser Gly Val Pro Asp Arg Phe
    50                  55                  60

Ser Ala Ser Lys Ser Gly Thr Ser Ala Ser Leu Ala Ile Thr Gly Leu
65                  70                  75                  80

Gln Ala Asp Asp Glu Ala Asp Tyr Tyr Cys Ala Thr Val Asp Glu Ala
                85                  90                  95

Leu Ser Gly Ser Val Phe Gly Gly Gly Thr Lys Val Thr Val Leu
            100                 105                 110

<210> SEQ ID NO 247
<211> LENGTH: 360
<212> TYPE: DNA
<213> ORGANISM: Homo sapiens
<220> FEATURE:
<223> OTHER INFORMATION: Ab 6 Non Germlined

<400> SEQUENCE: 247
caggtgcagc tggtgcaatc tggggctgag gtgaagaagc ctggggcctc agtgaaggtc      60
tcatgtaaaa tttccggaca cagcctcagt gaactgtcca tccactgggt gcgacagact     120
cccacaaaag gatttgagtg gatgggagga tttgatcctg aagagaatga aatagtctac     180
gcacagaggt tccagggcag agtcaccatg accgaggaca catctataga cacggcctac     240
ctgaccctga gcagcctgag atccgacgac acggccgttt attattgttc aatagtgggg     300
tctttcagtc cgctaacgtt gggcctctgg ggcaaaggga caatggtcac cgtctcgagt     360

<210> SEQ ID NO 248
<211> LENGTH: 120
<212> TYPE: PRT
<213> ORGANISM: Homo sapiens
<220> FEATURE:
<223> OTHER INFORMATION: Ab 6 Non Germlined

<400> SEQUENCE: 248

Gln Val Gln Leu Val Gln Ser Gly Ala Glu Val Lys Lys Pro Gly Ala
                5                   10                  15

Ser Val Lys Val Ser Cys Lys Ile Ser Gly His Ser Leu Ser Glu Leu
            20                  25                  30

Ser Ile His Trp Val Arg Gln Thr Pro Thr Lys Gly Phe Glu Trp Met
        35                  40                  45

Gly Gly Phe Asp Pro Glu Glu Asn Glu Ile Val Tyr Ala Gln Arg Phe
    50                  55                  60

Gln Gly Arg Val Thr Met Thr Glu Asp Thr Ser Ile Asp Thr Ala Tyr
65                  70                  75                  80

Leu Thr Leu Ser Ser Leu Arg Ser Asp Asp Thr Ala Val Tyr Tyr Cys
                85                  90                  95

Ser Ile Val Gly Ser Phe Ser Pro Leu Thr Leu Gly Leu Trp Gly Lys
            100                 105                 110

Gly Thr Met Val Thr Val Ser Ser
        115                 120

<210> SEQ ID NO 249
<211> LENGTH: 333
<212> TYPE: DNA
<213> ORGANISM: Homo sapiens
<220> FEATURE:
<223> OTHER INFORMATION: Ab 6 Non Germlined

<400> SEQUENCE: 249
caggctgtgc tgactcagcc gtcctcagtg tctggggccc cagggcagag ggtcaccatc      60

-continued

```
tcctgtactg ggagcggctc caacatcggg gcaccttatg atgtaagctg gtaccagcag      120
cttccaggaa cagcccccaa actcctcatc tatcataaca acaagcggcc ctcaggggtc      180
cctgaccgat tctctgcctc caagtctggc acctcagcct ccctggccat cactgggctc      240
caggctgacg atgaggctga ttattactgc gcgacggtcg aggccggcct gagtggttcg      300
gttttcgggg gagggaccaa gctcaccgtc cta                                   333
```

```
<210> SEQ ID NO 250
<211> LENGTH: 111
<212> TYPE: PRT
<213> ORGANISM: Homo sapiens
<220> FEATURE:
<223> OTHER INFORMATION: Ab 6 Non Germlined

<400> SEQUENCE: 250
```

Gln Ala Val Leu Thr Gln Pro Ser Ser Val Ser Gly Ala Pro Gly Gln
                5                   10                  15

Arg Val Thr Ile Ser Cys Thr Gly Ser Gly Ser Asn Ile Gly Ala Pro
            20                  25                  30

Tyr Asp Val Ser Trp Tyr Gln Gln Leu Pro Gly Thr Ala Pro Lys Leu
        35                  40                  45

Leu Ile Tyr His Asn Asn Lys Arg Pro Ser Gly Val Pro Asp Arg Phe
    50                  55                  60

Ser Ala Ser Lys Ser Gly Thr Ser Ala Ser Leu Ala Ile Thr Gly Leu
65                  70                  75                  80

Gln Ala Asp Asp Glu Ala Asp Tyr Tyr Cys Ala Thr Val Glu Ala Gly
                85                  90                  95

Leu Ser Gly Ser Val Phe Gly Gly Gly Thr Lys Leu Thr Val Leu
            100                 105                 110

```
<210> SEQ ID NO 251
<211> LENGTH: 30
<212> TYPE: PRT
<213> ORGANISM: Homo sapiens
<220> FEATURE:
<223> OTHER INFORMATION: Ab 6

<400> SEQUENCE: 251
```

Gln Val Gln Leu Val Gln Ser Gly Ala Glu Val Lys Lys Pro Gly Ala
                5                   10                  15

Ser Val Lys Val Ser Cys Lys Val Ser Gly Tyr Thr Leu Thr
            20                  25                  30

```
<210> SEQ ID NO 252
<211> LENGTH: 14
<212> TYPE: PRT
<213> ORGANISM: Homo sapiens
<220> FEATURE:
<223> OTHER INFORMATION: Ab 6

<400> SEQUENCE: 252
```

Trp Val Arg Gln Ala Pro Gly Lys Gly Leu Glu Trp Met Gly
                5                   10

```
<210> SEQ ID NO 253
<211> LENGTH: 32
<212> TYPE: PRT
<213> ORGANISM: Homo sapiens
<220> FEATURE:
<223> OTHER INFORMATION: Ab 6

<400> SEQUENCE: 253
```

```
Arg Val Thr Met Thr Glu Asp Thr Ser Thr Asp Thr Ala Tyr Met Glu
                5                  10                  15

Leu Ser Ser Leu Arg Ser Glu Asp Thr Ala Val Tyr Tyr Cys Ala Ile
            20                  25                  30

<210> SEQ ID NO 254
<211> LENGTH: 11
<212> TYPE: PRT
<213> ORGANISM: Homo sapiens
<220> FEATURE:
<223> OTHER INFORMATION: Ab 6

<400> SEQUENCE: 254

Trp Gly Gln Gly Thr Met Val Thr Val Ser Ser
                5                  10

<210> SEQ ID NO 255
<211> LENGTH: 22
<212> TYPE: PRT
<213> ORGANISM: Homo sapiens
<220> FEATURE:
<223> OTHER INFORMATION: Ab 6

<400> SEQUENCE: 255

Gln Ser Val Leu Thr Gln Pro Pro Ser Val Ser Gly Ala Pro Gly Gln
                5                  10                  15

Arg Val Thr Ile Ser Cys
            20

<210> SEQ ID NO 256
<211> LENGTH: 15
<212> TYPE: PRT
<213> ORGANISM: Homo sapiens
<220> FEATURE:
<223> OTHER INFORMATION: Ab 6

<400> SEQUENCE: 256

Trp Tyr Gln Gln Leu Pro Gly Thr Ala Pro Lys Leu Leu Ile Tyr
                5                  10                  15

<210> SEQ ID NO 257
<211> LENGTH: 32
<212> TYPE: PRT
<213> ORGANISM: Homo sapiens
<220> FEATURE:
<223> OTHER INFORMATION: Ab 6

<400> SEQUENCE: 257

Gly Val Pro Asp Arg Phe Ser Gly Ser Lys Ser Gly Thr Ser Ala Ser
                5                  10                  15

Leu Ala Ile Thr Gly Leu Gln Ala Glu Asp Glu Ala Asp Tyr Tyr Cys
            20                  25                  30

<210> SEQ ID NO 258
<211> LENGTH: 10
<212> TYPE: PRT
<213> ORGANISM: Homo sapiens
<220> FEATURE:
<223> OTHER INFORMATION: Ab 6

<400> SEQUENCE: 258

Phe Gly Gly Gly Thr Lys Leu Thr Val Leu
                5                  10
```